(12) United States Patent
Stamm et al.

(10) Patent No.: US 11,779,931 B2
(45) Date of Patent: Oct. 10, 2023

(54) OPTICAL DENSITY INSTRUMENT AND SYSTEMS AND METHODS USING THE SAME

(71) Applicant: bioMerieux, Inc., Durham, NC (US)

(72) Inventors: Perry D. Stamm, Dardenne Prairie, MO (US); Joel Patrick Harrison, Maryville, IL (US); Gregory R Maes, Fenton, MO (US); Jeffrey Edward Price, Wildwood, MO (US); Jack R. Hoffmann, Jr., St. Louis, MO (US); John Kenneth Korte, St. Louis, MO (US); Daniel Joseph Pingel, Saint Peters, MO (US); Walter J. Clynes, O'Fallon, MO (US); Sean Gregory Furman, St. Charles, MO (US); Leonard H. Schleicher, St. Charles, MO (US); Christopher George Kocher, St. Louis, MO (US); Brian David Peterson, Wentzville, MO (US); Jacky S. Yam, St. Louis, MO (US)

(73) Assignee: bioMerieux Inc., Durham, NC (US)

( * ) Notice: Subject to any disclaimer, the term of this patent is extended or adjusted under 35 U.S.C. 154(b) by 85 days.

(21) Appl. No.: 17/470,717

(22) Filed: Sep. 9, 2021

(65) Prior Publication Data
US 2022/0097046 A1  Mar. 31, 2022

Related U.S. Application Data

(63) Continuation of application No. 16/655,315, filed on Oct. 17, 2019, now Pat. No. 11,141,733, which is a
(Continued)

(51) Int. Cl.
*B01L 3/00* (2006.01)
*G01N 21/01* (2006.01)
(Continued)

(52) U.S. Cl.
CPC ............ *B01L 3/50853* (2013.01); *G01N 1/10* (2013.01); *G01N 15/06* (2013.01); *G01N 21/01* (2013.01);
(Continued)

(58) Field of Classification Search
CPC ......... B01L 2200/14; B01L 2300/0654; B01L 2300/0803; B01L 2300/12; B01L 3/50853;
(Continued)

(56) References Cited

U.S. PATENT DOCUMENTS 2,157,438 A    5/1939  Sparks
2,436,262 A    2/1948  Miller
(Continued)

FOREIGN PATENT DOCUMENTS

CN    2356342 Y    12/1999
CN    3159492      1/2000
(Continued)

OTHER PUBLICATIONS

Office Action for Chinese Application No. 2018800328421 dated Nov. 18, 2021.
(Continued)

*Primary Examiner* — Tri T Ton
(74) *Attorney, Agent, or Firm* — Alston & Bird LLP

(57) ABSTRACT

Instruments, systems, and methods for measuring optical density of microbiological samples are provided. In particular, optical density instruments providing improved safety, efficiency, comfort, and convenience are provided. Such optical density instruments include a handheld portion and a base station. The optical density instruments may be used in systems and methods for measuring optical density of biological samples.

19 Claims, 45 Drawing Sheets

Related U.S. Application Data continuation of application No. 15/958,760, filed on Apr. 20, 2018, now Pat. No. 10,478,821.

(60) Provisional application No. 62/488,450, filed on Apr. 21, 2017, provisional application No. 62/487,807, filed on Apr. 20, 2017, provisional application No. 62/487,796, filed on Apr. 20, 2017, provisional application No. 62/487,860, filed on Apr. 20, 2017, provisional application No. 62/487,736, filed on Apr. 20, 2017.

(51) Int. Cl.
    *G01N 21/59*     (2006.01)
    *G01N 21/47*     (2006.01)
    *G01N 1/10*     (2006.01)
    *G01N 21/27*     (2006.01)
    *G01N 33/487*     (2006.01)
    *G01N 21/03*     (2006.01)
    *G01N 15/06*     (2006.01)
    *G01N 21/51*     (2006.01)
    *G01N 21/88*     (2006.01)
    *G01N 21/93*     (2006.01)

(52) U.S. Cl.
CPC ....... *G01N 21/0303* (2013.01); *G01N 21/274* (2013.01); *G01N 21/4738* (2013.01); *G01N 21/4785* (2013.01); *G01N 21/51* (2013.01); *G01N 21/5907* (2013.01); *G01N 21/8806* (2013.01); *G01N 21/93* (2013.01); *G01N 33/487* (2013.01); *G01N 33/48735* (2013.01); *B01L 2200/14* (2013.01); *B01L 2300/0654* (2013.01); *B01L 2300/0803* (2013.01); *B01L 2300/12* (2013.01); *G01N 21/474* (2013.01); *G01N 2015/0693* (2013.01); *G01N 2021/0168* (2013.01); *G01N 2021/0389* (2013.01); *G01N 2021/4769* (2013.01); *G01N 2021/598* (2013.01); *G01N 2201/126* (2013.01); *G01N 2201/12707* (2013.01)

(58) Field of Classification Search
CPC .. G01N 1/10; G01N 15/06; G01N 2015/0693; G01N 2021/0168; G01N 2021/0389; G01N 2021/4769; G01N 2021/598; G01N 21/01; G01N 21/0303; G01N 21/274; G01N 21/4738; G01N 21/474; G01N 21/4785; G01N 21/51; G01N 21/5907; G01N 21/8806; G01N 21/93; G01N 2201/126; G01N 2201/12707; G01N 33/487; G01N 33/48735; G06Q 10/06393; G06Q 50/10; G06Q 50/20; G09B 7/04
USPC .......................................... 356/432–448, 250
See application file for complete search history.

(56) References Cited

U.S. PATENT DOCUMENTS

| | | | |
|---|---|---|---|
| 2,863,354 A | 12/1958 | Diehl et al. | |
| 2,874,606 A | 2/1959 | Leiterer | |
| 3,554,648 A | 1/1971 | Boostrom et al. | |
| 3,712,144 A | 1/1973 | Kuzel et al. | |
| 3,714,445 A | 1/1973 | Blachere et al. | |
| 3,775,013 A | 11/1973 | Simms | |
| 3,783,635 A | 1/1974 | Perez | |
| 3,809,912 A | 5/1974 | Henning | |
| 3,826,574 A | 7/1974 | Brown, Jr. | |
| 3,962,041 A | 6/1976 | Muller et al. | |
| 3,977,794 A | 8/1976 | Liedholz | |
| 4,118,625 A | 10/1978 | Underwood | |
| 4,136,953 A | 1/1979 | Klein et al. | |
| 4,193,692 A | 3/1980 | Wynn | |
| 4,291,983 A | 9/1981 | Kraft et al. | |
| 4,343,552 A | 8/1982 | Blades | |
| 5,137,693 A | 8/1992 | Mawhirt | |
| 5,140,168 A | 8/1992 | King | |
| 5,331,177 A | 7/1994 | Kunisiak et al. | |
| 5,506,679 A | 4/1996 | Cooper et al. | |
| 5,604,590 A | 2/1997 | Cooper et al. | |
| 5,616,923 A | 4/1997 | Rich et al. | |
| 5,651,941 A | 7/1997 | Stark et al. | |
| 5,687,849 A | 11/1997 | Borenstein et al. | |
| 5,736,410 A | 4/1998 | Zarling et al. | |
| 5,863,754 A | 1/1999 | Bajard | |
| 5,867,266 A | 2/1999 | Craighead | |
| 5,872,361 A | 2/1999 | Paoli et al. | |
| 5,940,178 A | 8/1999 | Barber et al. | |
| D439,673 S | 3/2001 | Brophy et al. | |
| 6,198,536 B1 | 3/2001 | Baker | |
| 6,274,092 B1 | 8/2001 | Itoh | |
| D453,573 S | 2/2002 | Lafond et al. | |
| 6,359,689 B1 | 3/2002 | Stansell et al. | |
| 6,537,772 B1 | 3/2003 | Alarcon et al. | |
| 7,485,264 B2 | 2/2009 | Itoh | |
| 7,659,980 B1 | 2/2010 | Mitchell et al. | |
| D624,194 S | 9/2010 | Pack et al. | |
| 7,910,067 B2 | 3/2011 | Knight et al. | |
| 8,147,777 B2 | 4/2012 | Schacher et al. | |
| D679,412 S | 4/2013 | Khamu | |
| D687,567 S | 8/2013 | Jungheim et al. | |
| D709,625 S | 7/2014 | Baum et al. | |
| 9,612,196 B2 * | 4/2017 | Saraswat | G01N 21/5907 |
| 10,591,416 B2 | 3/2020 | Chen et al. | |
| 2003/0005928 A1 | 1/2003 | Appel et al. | |
| 2003/0058450 A1 | 3/2003 | Mosley et al. | |
| 2003/0085221 A1 | 5/2003 | Smolenski et al. | |
| 2003/0139886 A1 | 7/2003 | Bodzin et al. | |
| 2004/0147843 A1 | 7/2004 | Bambot et al. | |
| 2005/0106746 A1 | 5/2005 | Shinn et al. | |
| 2006/0001865 A1 | 1/2006 | Bellalou et al. | |
| 2007/0269853 A1 | 11/2007 | Galiano | |
| 2008/0072664 A1 | 3/2008 | Hansen et al. | |
| 2008/0079943 A1 | 4/2008 | Li | |
| 2010/0028859 A1 | 2/2010 | Moshe et al. | |
| 2010/0110220 A1 | 5/2010 | Leugers et al. | |
| 2010/0245827 A1 | 9/2010 | Palumbo et al. | |
| 2011/0151503 A1 | 6/2011 | Galiano | |
| 2011/0270128 A1 | 11/2011 | Zhao et al. | |
| 2011/0306032 A1 | 12/2011 | Galiano et al. | |
| 2011/0306087 A1 | 12/2011 | Galiano et al. | |
| 2011/0307183 A1 | 12/2011 | Galiano et al. | |
| 2012/0009558 A1 | 1/2012 | Armstrong et al. | |
| 2012/0022794 A1 | 1/2012 | Andelic et al. | |
| 2012/0063956 A1 | 3/2012 | Truex et al. | |
| 2012/0082446 A1 | 4/2012 | Kumai | |
| 2012/0140230 A1 | 6/2012 | Miller | |
| 2013/0022962 A1 | 1/2013 | Galiano | |
| 2013/0258336 A1 | 10/2013 | Ostermeyer et al. | |
| 2014/0233015 A1 | 8/2014 | Mander | |
| 2015/0031051 A1 | 1/2015 | Mohan et al. | |
| 2015/0036121 A1 | 2/2015 | Kurowski et al. | |
| 2015/0086971 A1 | 3/2015 | Botma et al. | |
| 2015/0108076 A1 | 4/2015 | Branch et al. | |
| 2015/0355208 A1 | 12/2015 | German | |
| 2016/0160260 A1 | 6/2016 | Marshall et al. | |
| 2016/0209328 A1 | 7/2016 | Berndt et al. | |
| 2016/0266028 A1 | 9/2016 | Wyatt | |
| 2016/0341945 A1 * | 11/2016 | Ou | G02B 21/086 |
| 2017/0307525 A1 | 10/2017 | Langoff et al. | |
| 2019/0129156 A1 | 5/2019 | Knebel et al. | |
| 2019/0162744 A1 | 5/2019 | Kazama et al. | |

FOREIGN PATENT DOCUMENTS

| | | |
|---|---|---|
| CN | 3383938 | 11/2003 |
| CN | 2919238 | 7/2007 |
| CN | 300905477 D | 12/2007 |
| CN | 201141824 | 10/2008 |

(56) References Cited

FOREIGN PATENT DOCUMENTS

| | | |
|---|---|---|
| CN | 301068253 | 11/2008 |
| CN | 204142554 | 2/2010 |
| CN | 101893564 A | 11/2010 |
| CN | 102128814 A | 7/2011 |
| CN | 103645162 A | 3/2014 |
| CN | 203479704 | 3/2014 |
| CN | 302968146 S | 6/2014 |
| CN | 302983583 S | 6/2014 |
| CN | 302995249 S | 6/2014 |
| CN | 103923827 | 7/2014 |
| CN | 303227067 S | 12/2014 |
| CN | 104266895 | 1/2015 |
| CN | 105277472 A | 1/2016 |
| CN | 105492890 A | 4/2016 |
| CN | 105593665 A | 5/2016 |
| CN | 205246536 U | 5/2016 |
| DE | 3516529 | 11/1986 |
| DE | 3608552 A1 | 9/1987 |
| DE | 202004020585 | 9/2005 |
| EP | 3023768 | 5/2016 |
| GB | 150 183 A | 9/1920 |
| GB | 4028381 | 1/2013 |
| GB | 4028382 | 1/2013 |
| JP | 3049676 | 6/1998 |
| JP | H10 284848 A | 10/1998 |
| JP | 3061144 | 9/1999 |
| JP | 2003/000224 | 1/2003 |
| KR | 100580312 | 5/2006 |
| KR | 20090081998 | 7/2009 |
| KR | 20090082060 | 7/2009 |
| KR | 100580313 | 5/2018 |
| TW | 201215873 A | 4/2012 |
| WO | WO 1993/009440 A1 | 5/1993 |
| WO | WO 1995/25950 A1 | 9/1995 |
| WO | WO 1998/000701 A1 | 1/1998 |
| WO | WO 1998/047999 A1 | 10/1998 |
| WO | WO 2000/065332 A1 | 11/2000 |
| WO | WO 2001/063253 A1 | 8/2001 |
| WO | WO 2004/015136 A1 | 2/2004 |
| WO | WO 2008/039442 A1 | 4/2008 |
| WO | WO 2010/090391 A2 | 8/2010 |
| WO | WO 2010/097687 A1 | 9/2010 |
| WO | WO 2010/108804 A1 | 9/2010 |
| WO | WO 2014/137333 A1 | 9/2014 |
| WO | WO 2015/026794 A1 | 2/2015 |
| WO | WO 2015/164274 A1 | 10/2015 |
| WO | WO 2016/049604 A1 | 3/2016 |
| WO | WO 2016/051267 A1 | 4/2016 |
| WO | WO 2016/191646 A1 | 12/2016 |
| WO | WO 2018/195509 A1 | 10/2018 |

OTHER PUBLICATIONS

Office Action for European Application No. 18724031.2 dated Oct. 7, 2021.
First Office Action and Search Report for Chinese Application No. 201880032807.X, 9 pgs., dated Feb. 8, 2022.
International Search Report and Written Opinion for Application No. PCT/US2018/028699 dated Jul. 16, 2018, 14 pages.
International Search Report and Written Opinion for Application No. PCT/US2018/028696 dated Sep. 7, 2018.
International Search Report and Written Opinion for Application No. PCT/US2018/028701 dated Sep. 10, 2018.
International Search Report and Written Opinion for Application No. PCT/US2018/028702 dated Sep. 10, 2018.
Office Action for European Application No. 18724032.0 dated Jan. 28, 2021.
Office Action for Australian Patent Application No. 2018254602 dated Jan. 27, 2021.
Office Action for Canadian Patent Application No. 3,061,024 dated May 27, 2021.
Office Action for Indian Patent Application No. 201917045483 dated Feb. 17, 2021.
Office Action for Canadian Patent Application No. 3,060,074 dated May 13, 2021.
Office Action for Canadian Patent Application No. 3,060,377 dated May 28, 2021.
Second Office Action and Supplementary Search Report for Chinese Application No. 201880032842.1, 26 pgs., dated Aug. 30, 2022.
Non-Final Office Action for U.S. Appl. No. 17/524,044, 15 pgs., dated Jan. 12, 2023.
Notice of Allowance for U.S. Appl. No. 17/474,544, 10 pgs., dated Jan. 30, 2023.

* cited by examiner

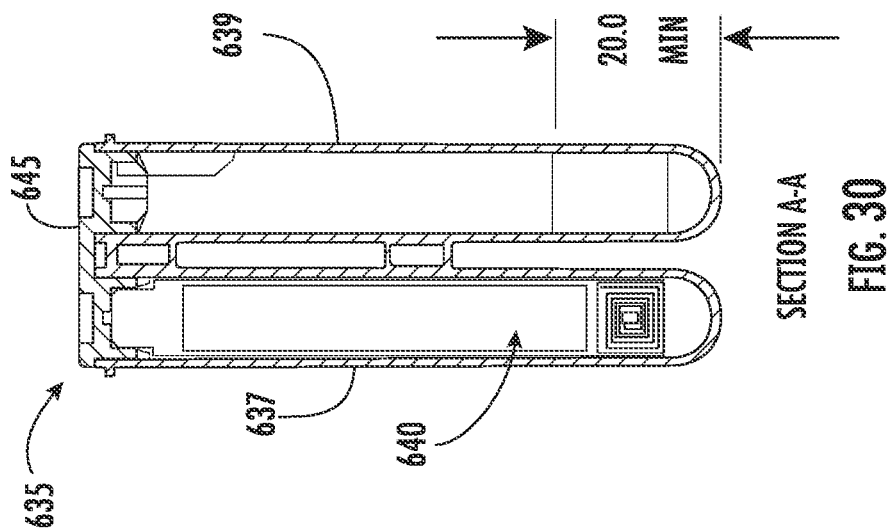
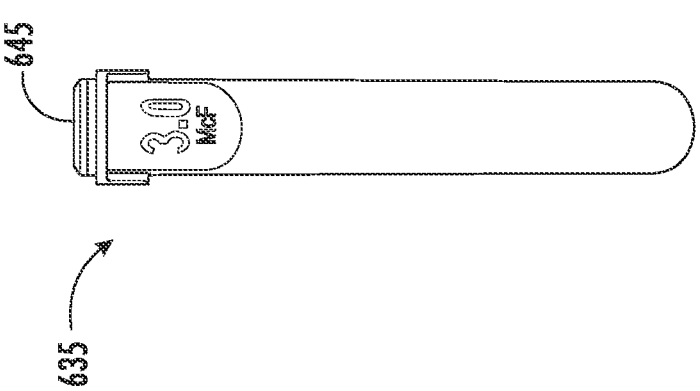
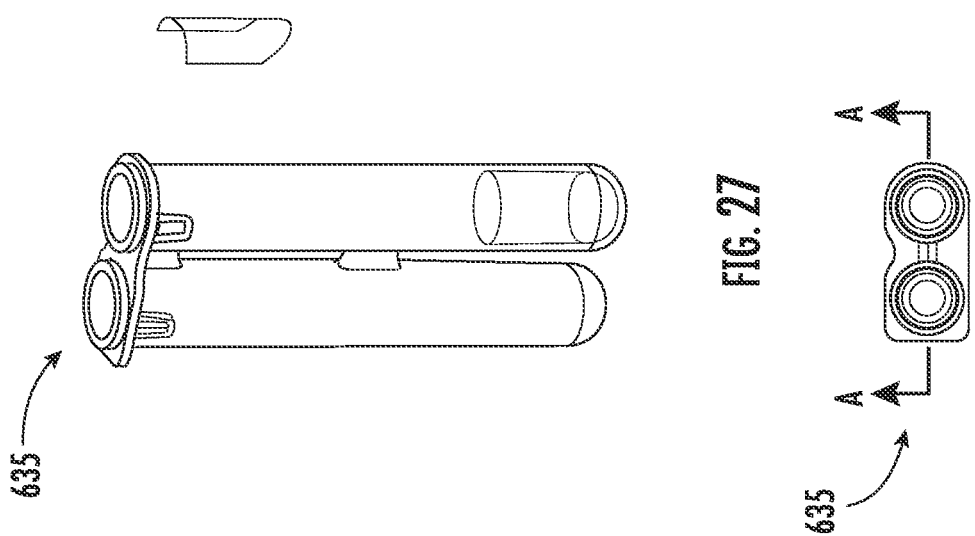

DETAIL B —650

OPTICAL DENSITY INSTRUMENT AND SYSTEMS AND METHODS USING THE SAME

CROSS-REFERENCE TO RELATED APPLICATIONS

This is a continuation application of U.S. application Ser. No. 16/655,315, filed Oct. 17, 2019, which application is a continuation of U.S. application Ser. No. 15/958,760, filed Apr. 20, 2018, which application claims the benefit of each of the following: U.S. Provisional Application No. 62/488,450, which is entitled "Optical Density Instrument And Systems And Methods Using The Same" and was filed Apr. 21, 2017; U.S. Provisional Application No. 62/487,807, which is entitled "Optical Test Platform" and was filed Apr. 20, 2017; U.S. Provisional Application No. 62/487,796, which is entitled "Optical Density Instrument And Systems And Methods Using The Same" and was filed Apr. 20, 2017; U.S. Provisional Application No. 62/487,860, which is entitled "Tip Resistant Optical Testing Instrument" and was filed Apr. 20, 2017; and U.S. Provisional Application No. 62/487,736, which is entitled "Method, Apparatus, And Computer Program Product For Controlling Components Of A Detection Device" and was filed Apr. 20, 2017. Each of the foregoing applications is hereby incorporated by reference in its entirety.

TECHNICAL FIELD

The presently-disclosed invention relates generally to devices, systems, and methods for measuring sample optical density, and more particularly to devices, systems, and methods for measuring optical density of microbiological samples.

BACKGROUND

In microbiology laboratories and other similar settings, lab technicians, scientists, and other practitioners use laboratory equipment to measure conditions of liquid suspensions. The suspensions may be observed and manipulated in clear polystyrene test tubes, glass test tubes, or other similar vials. The practitioner may utilize various devices or instruments to perform readings and measurements on the liquid in a sample tube. The practitioner may also manipulate the fluid while performing measurements, or intermittingly between measurements. In some examples, a practitioner may manipulate the fluid while monitoring a measurement or reading performed by an instrument.

One example of such a measurement performed in a microbiology lab includes measuring the turbidity and/or concentration of microorganisms in the liquid using an optical density instrument. The practitioner may use the instrument to achieve the optimal dilution of the sample by diluting the solutions with saline, or increasing the levels of microorganisms in the fluid. The optical density sensors in a device or instrument may be configured to detect light emitted in the area of the sample tube to measure characteristics of the liquid.

Existing instruments are often incapable of being used continuously during preparation of a sample because of poor visibility, interference from external and internal light sources, leaks and other electrical damage to the instrument's internal components, and high manufacturing costs. The inventors have identified numerous other deficiencies with existing technologies in the field, the remedies for which are the subject of the embodiments described herein.

BRIEF SUMMARY

One or more embodiments of the invention may address one or more of the aforementioned problems. Certain embodiments according to the invention provide devices, systems, and methods for measuring optical density of microbiological samples. In particular, embodiments of the invention are directed to various features of such instruments, systems, and methods that provide increased safety, comfort, efficiency, and convenience for users.

In accordance with certain embodiments, the optical density instrument includes a handheld unit having a top and a bottom and a base station having at least a handheld unit receiving portion such that the handheld unit is configured to operably couple to the base station both when the handheld unit engages the handheld unit receiving portion and when the handheld unit is separated from the base station. The handheld unit further includes an optical test platform having an open top and a cavity configured to receive at least a portion of a first sample tube and a bottom portion positioned within the handheld unit such that the first sample tube extends above the top of the handheld unit when inserted in the optical test platform. Moreover, the handheld unit includes an emitter positioned within the handheld unit at the bottom portion of the optical test platform such that the emitter is configured to emit light into the cavity, and the emitter is configured to emit light into the first sample tube when the first sample tube is inserted in the optical test platform. Additionally, the handheld unit includes at least one sensor positioned in optical communication with the emitter via the cavity, such that the at least one sensor is configured to receive the emitted light from the cavity, and such that the at least one sensor is configured to receive light emitted by the emitter and passing through the first sample tube when the first sample tube is inserted in the optical test platform. In addition, the handheld unit includes an illumination light positioned at the bottom portion of the optical test platform that is configured to illuminate the first sample tube when the first sample tube is inserted in the optical test platform. In some embodiments, the handheld unit may include a spring defining a first leg and a second leg, and the first leg and the second leg may be configured to apply a force on a sample tube towards a point between the first leg and the second leg.

In another aspect, certain embodiments according to the invention provide a system for measuring optical density of a sample. In accordance with certain embodiments, the system includes a handheld unit having a top and a bottom, a base station having at least a handheld unit receiving portion such that the handheld unit is configured to operably couple to the base station both when the handheld unit engages the handheld unit receiving portion and when the handheld unit is separated from the base station, and a computing device having a user interface. The handheld unit further includes an optical test platform having an open top and a cavity configured to receive at least a portion of a first sample tube and a bottom portion positioned within the handheld unit such that the first sample tube extends above the top of the handheld unit when inserted in the optical test platform. Moreover, the handheld unit includes an emitter positioned within the handheld unit at the bottom portion of the optical test platform such that the emitter is configured to emit light into the cavity, and the emitter is configured to emit light into the first sample tube when the first sample tube is inserted in the optical test platform. Additionally, the handheld unit includes at least one sensor positioned in optical communication with the emitter via the cavity, such that the at least one sensor is configured to receive the emitted light from the cavity, and such that the at least one sensor is configured to receive light emitted by the emitter and passing through the first sample tube when the first sample tube is inserted in the optical test platform. In addition, the handheld unit includes an illumination light positioned at the bottom portion of the optical test platform that is configured to illuminate the first sample tube when the first sample tube is inserted in the optical test platform.

In yet another aspect, certain embodiments according to the invention provide a method for measuring optical density of sample. In accordance with certain embodiments, the method includes receiving a first sample tube containing the sample, illuminating the sample in the first sample tube for visual inspection by a user according to a light modulation pattern, emitting a source light through the sample in the first sample tube according to the light modulation pattern, detecting a portion of the source light transmitted through or reflected by the sample to generate raw light data, and converting the raw light data into optical density data.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIGS. 27-31 show an example dual tube with a calibration capability according to some embodiments discussed herein;

DETAILED DESCRIPTION

The invention now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

The invention includes, according to certain embodiments, devices, systems, and methods for measuring optical density of microbiological samples. In particular, embodiments of the invention are directed to various features of such instruments, systems, and methods that provide increased safety, comfort, efficiency, and convenience for users. Although the term "optical density" is used throughout this disclosure, one of ordinary skill in the art would understand that this term is interchangeable with the term "turbidity" and should be interpreted as such.

I. Optical Density Instrument

Figure 1:
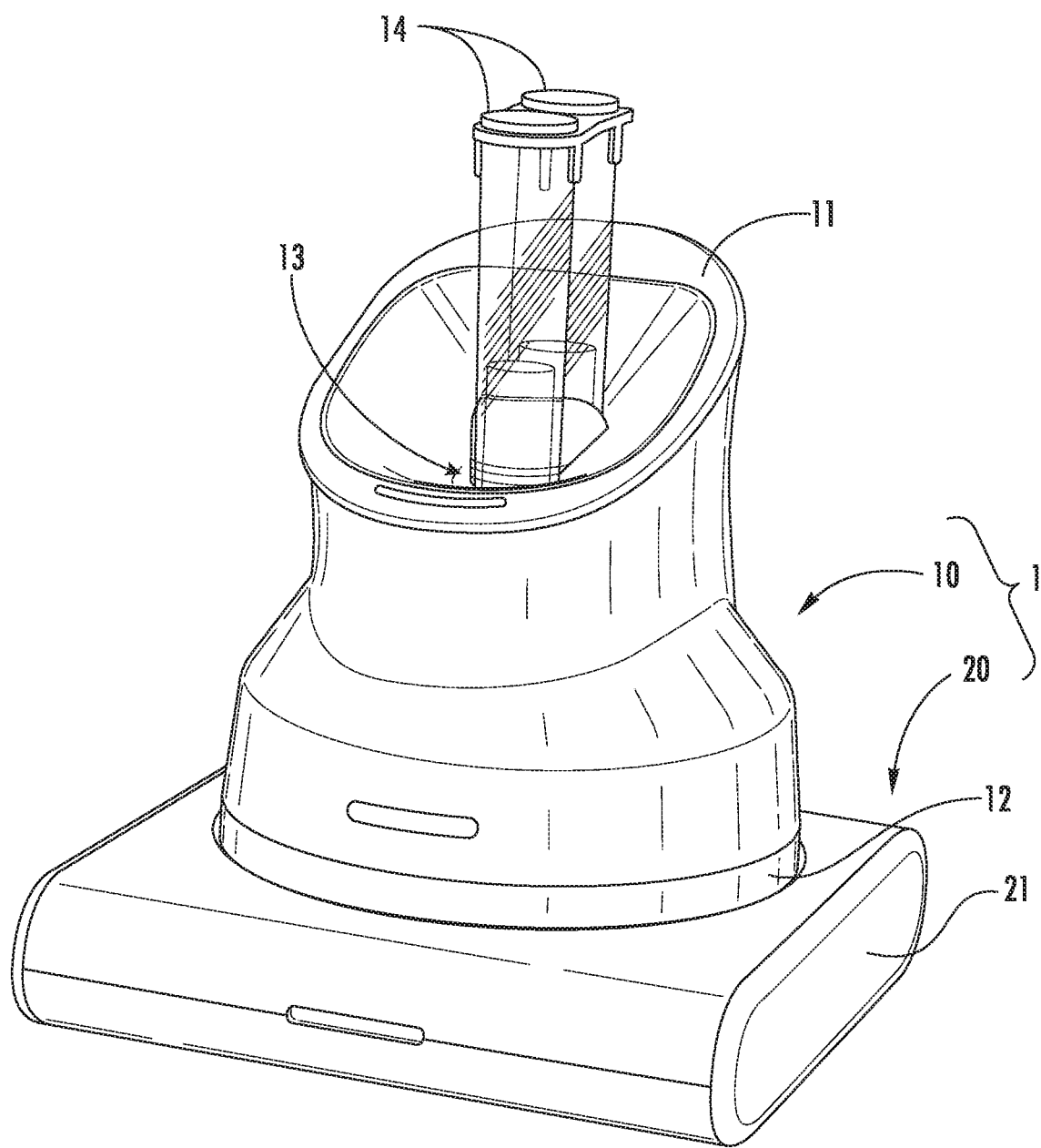
FIGS. 1 and 2 are perspective views of an optical density instrument in accordance with certain embodiments of the invention.
Figure 2:
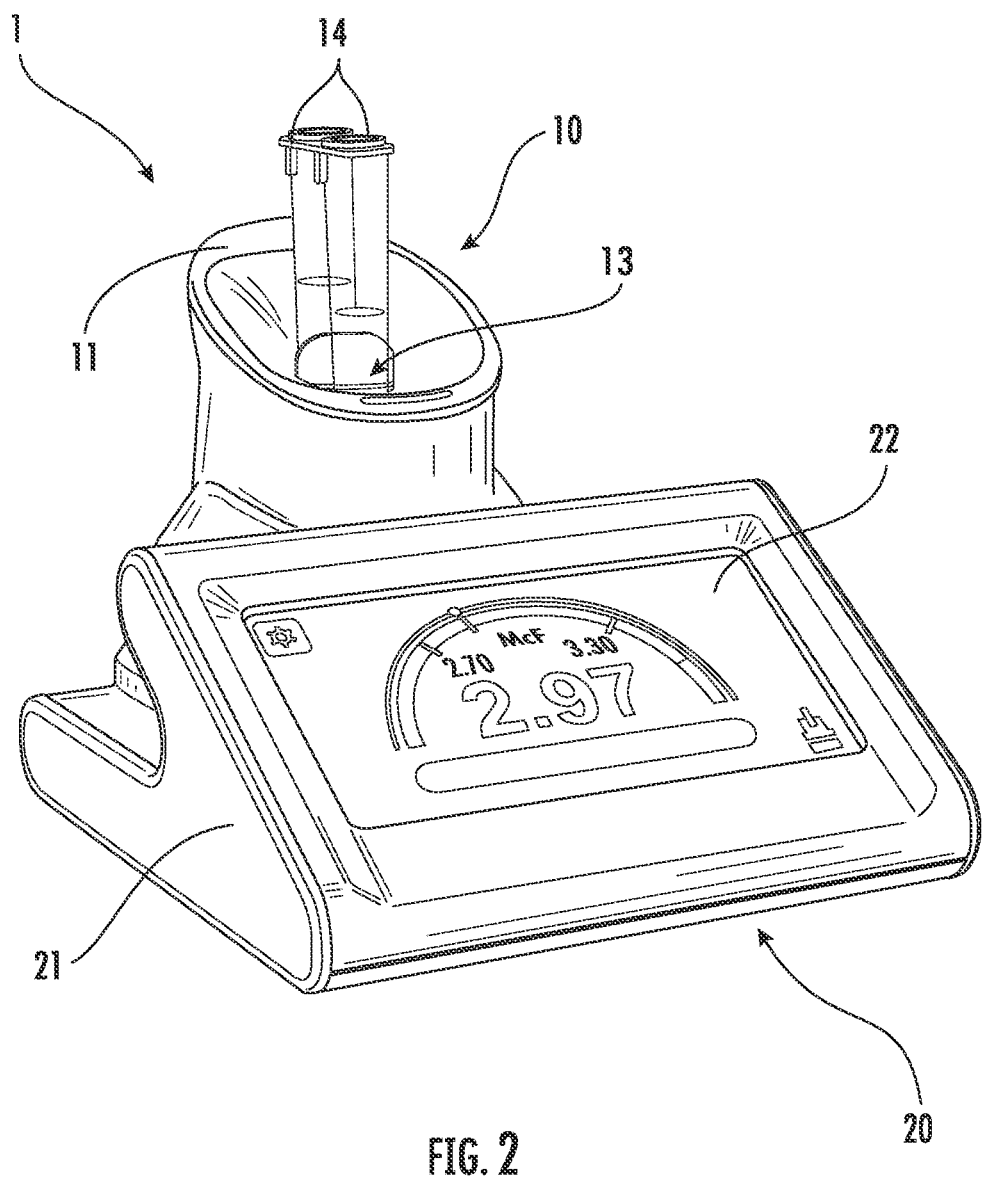

Certain embodiments according to the invention provide optical density instruments. For example, FIGS. 1 and 2 are perspective views of an optical density instrument in accordance with certain embodiments of the invention. As shown in FIGS. 1 and 2, the optical density instrument 1 may include a handheld unit 10 and a base station 20. The handheld unit 10 may be operably coupled to the base station 20 via a handheld unit connector 24 (shown in FIGS. 5, 6, and 8A-11) when positioned on a handheld unit receiving portion 23 (shown in FIGS. 5, 6, and 8A-11) on the base station 20. In some embodiments, the handheld unit 10 is battery operated for convenience and flexibility. In such embodiments, for example, the battery may charge when the handheld unit 10 is attached to the base station 20 via, for instance, the handheld unit connector 24. Handheld unit connector 24 may comprise a floating pin connector. The handheld unit 10 may transmit data to the base station 20 via Bluetooth™ or another wireless or wired protocol.

FIGS. 5-14, for instance, show various views of the base station 20 (e.g., in either a standard charging base or a charging base with screen configuration). As shown and mentioned above, the base station 20 may include a support portion 21, a handheld unit receiving portion 23, a handheld unit connector 24, and/or a user interface connector 25. As can be seen, for example, in FIG. 5, the support portion 21 provides a support for the remaining features of the base station 20. The support portion 21 may be substantially flat and supported by feet 26. The size of the support portion 21 may depend upon whether the base station 20 includes a display screen 22, as discussed in more detail below. The handheld unit receiving portion 23 may be recessed into the support portion 21 of the base station 20. Moreover, the handheld unit receiving portion 23 may have a substantially round shape. However, the handheld unit receiving portion 23 may have any shape that corresponds to the shape of the handheld unit 10. In further embodiments and as discussed in more detail below, the base station 20 may be wire or wirelessly connected to a user interface of a separate computing device (e.g., a standalone computer, or other data collection or display device) via the user interface connector 25 for receiving the optical density (i.e. turbidity) data in real time. The user interface connector 25 may be a universal serial bus (USB) connector, a serial connector, or other wired protocol. In some embodiments, the base station 20 may be wirelessly connected to the user interface of the separate computing device. In this regard, the optical density instrument 1 may continuously communicate with the user interface 130 during operation of the optical density instrument. In some other embodiments, the communication between the optical density instrument 1 and the user interface 130 may not be continuous. In further embodiments, for instance, the optical density instrument 1 may be in communication with the user interface via, for example, processing circuitry discussed in more detail below.

According to certain embodiments, the base station 20 may or may not include a display screen 22. For example, FIGS. 1 and 5-9B provide various views of a base portion 20 without a display screen. However, FIGS. 2 and 10A-14 provide various views of a base portion 20 having a display screen 22. The display screen 22 may be in communication with the handheld unit 10 via, for example, processing circuitry discussed in more detail below. In this regard, the display screen 22 may display measurement (e.g., turbidity measurements) generated by the handheld unit 10 for monitoring by a user. The display screen 22 may be in continuous or discontinuous communication with the handheld unit 10. In some embodiments, using the interference reduction and processing techniques described herein, the handheld unit 10 may send continuous, real time data to the base station 20 while also illuminating the sample tubes.

Figure 3A:
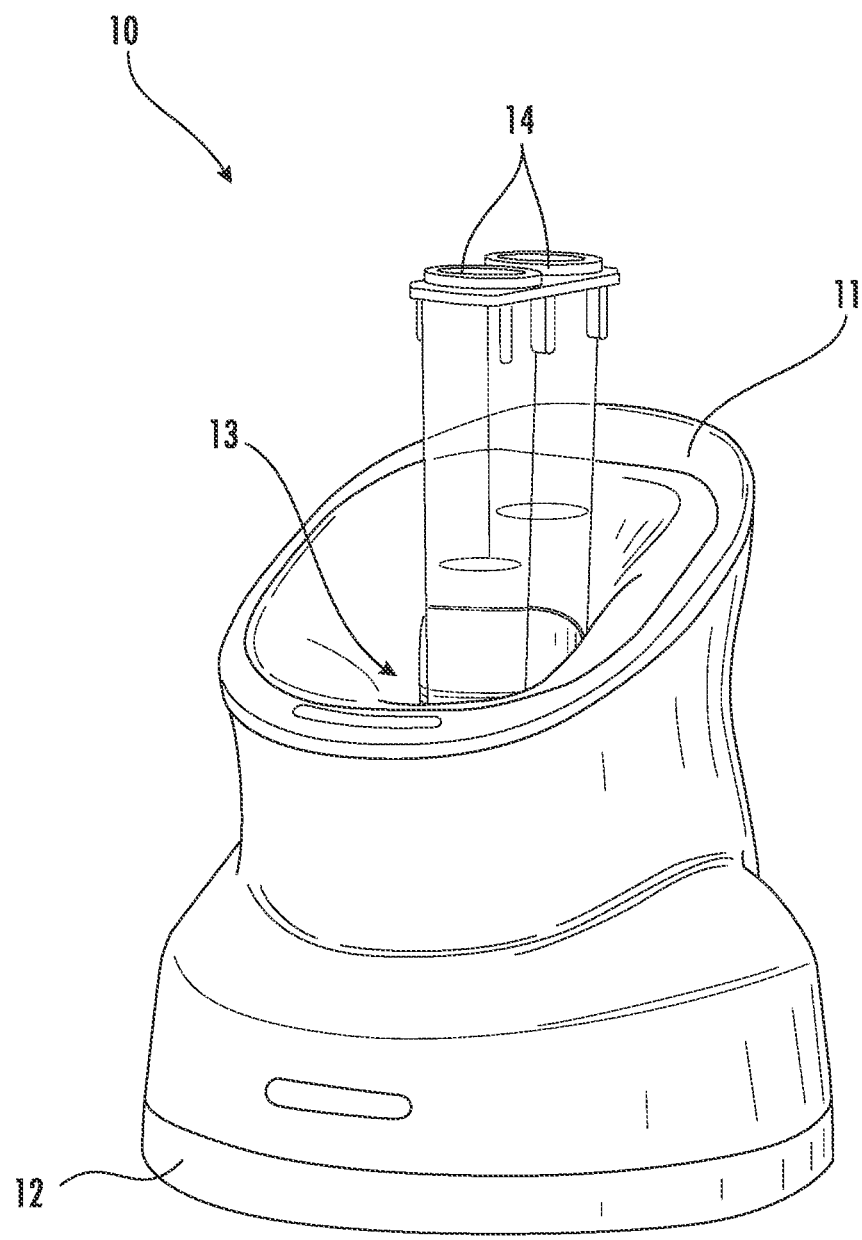
FIGS. 3A and 3B are perspective views of the front of a handheld unit in accordance with certain embodiments of the invention.
Figure 3B:
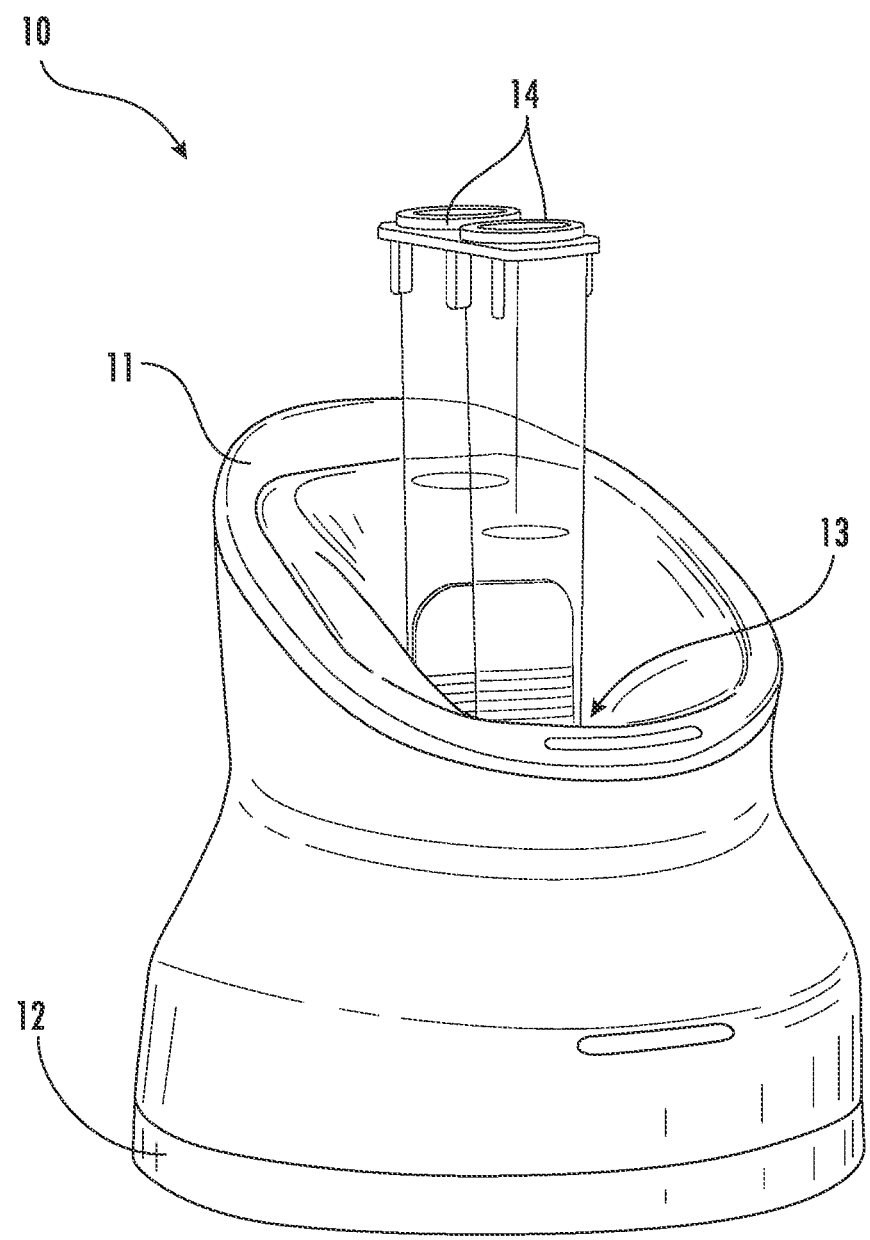
Figure 4:
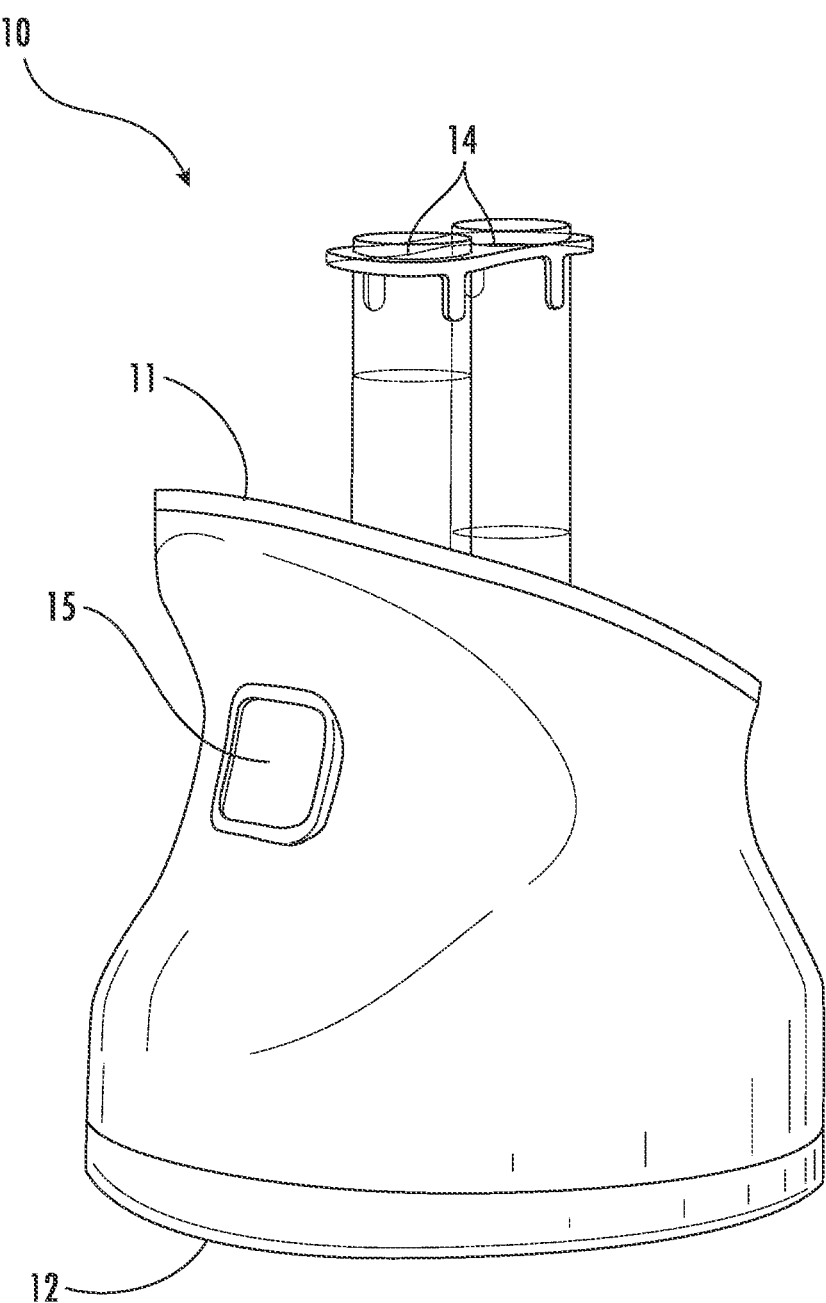
FIG. 4 is a perspective view of the back of a handheld unit in accordance with certain embodiments of the invention.
Figure 5:
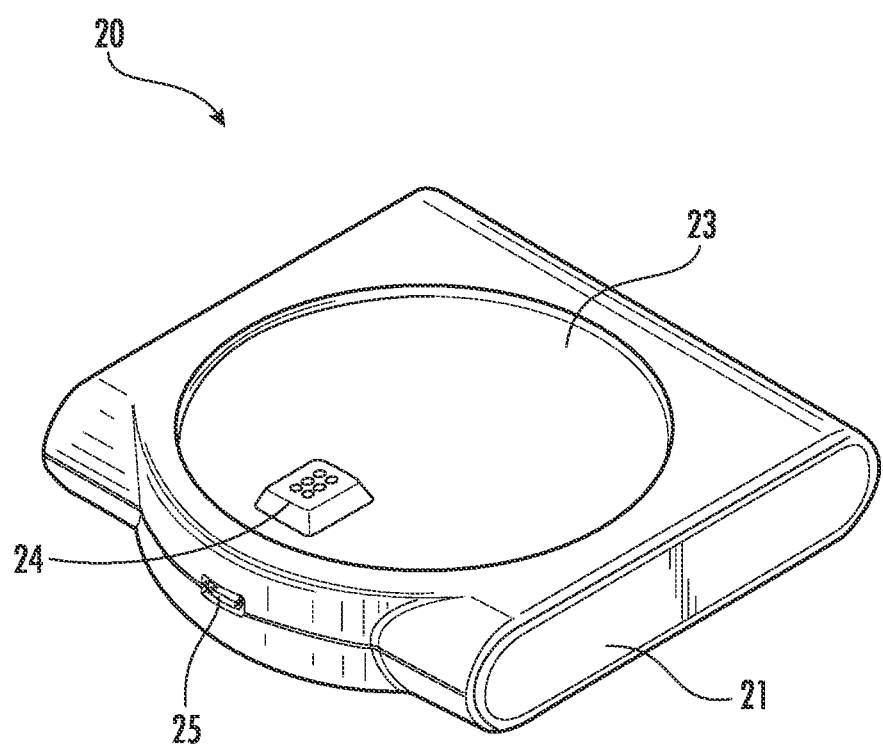
FIG. 5 is a perspective view of a base station in accordance with certain embodiments of the invention.
Figure 6:
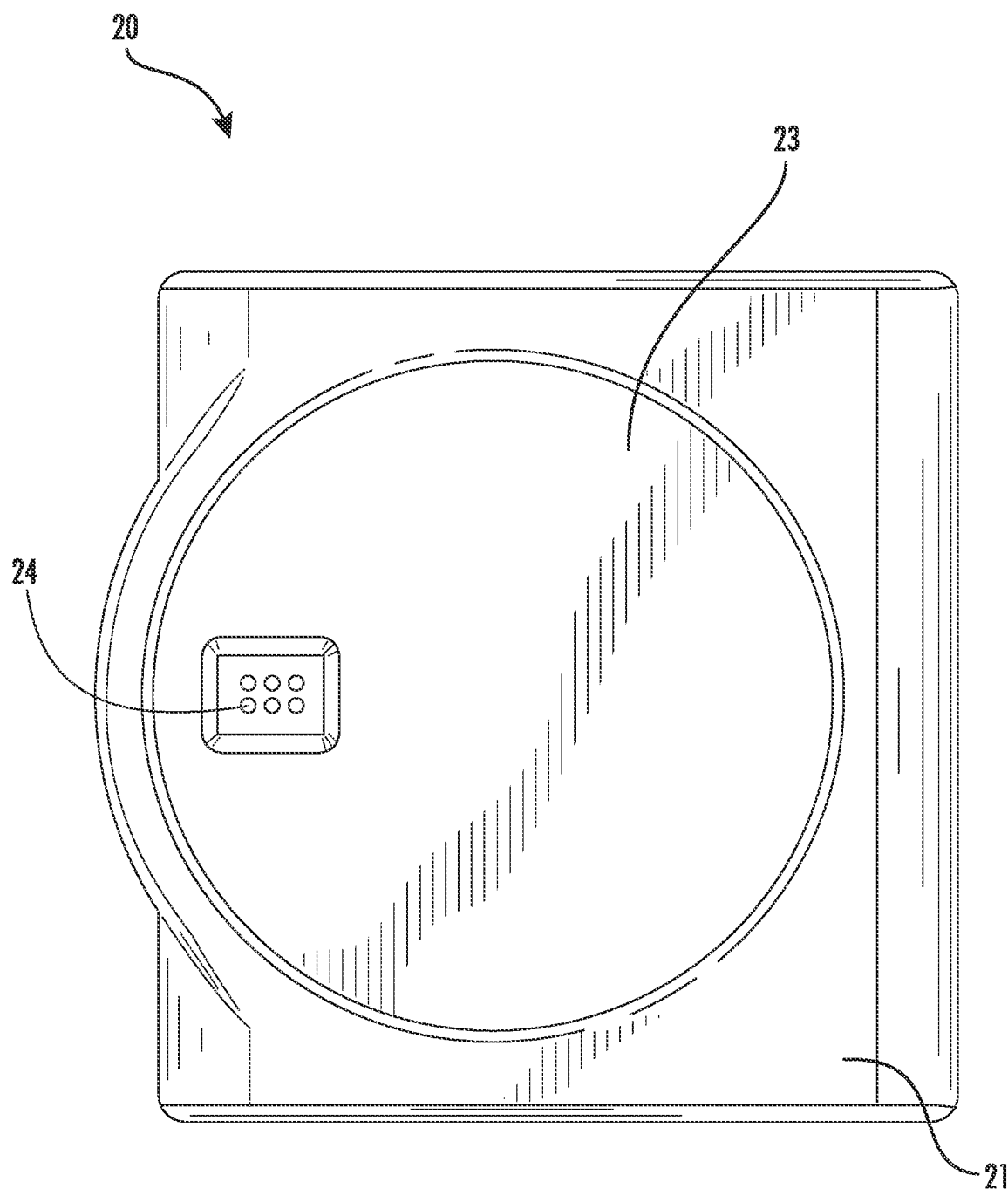
FIG. 6 is a top view of a base station in accordance with certain embodiments of the invention.
Figure 7:
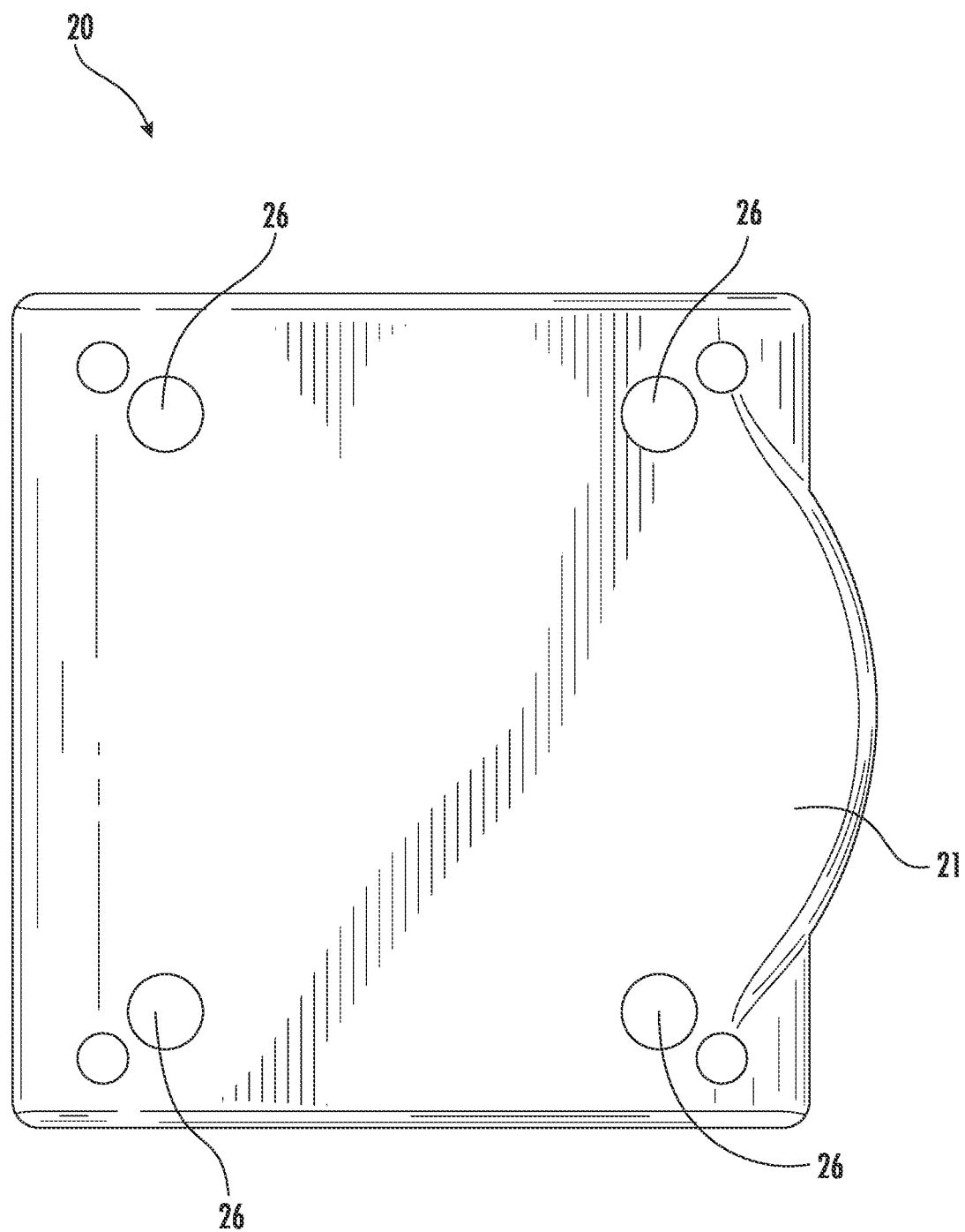
FIG. 7 is a bottom view of a base station in accordance with certain embodiments of the invention.
Figure 8A:
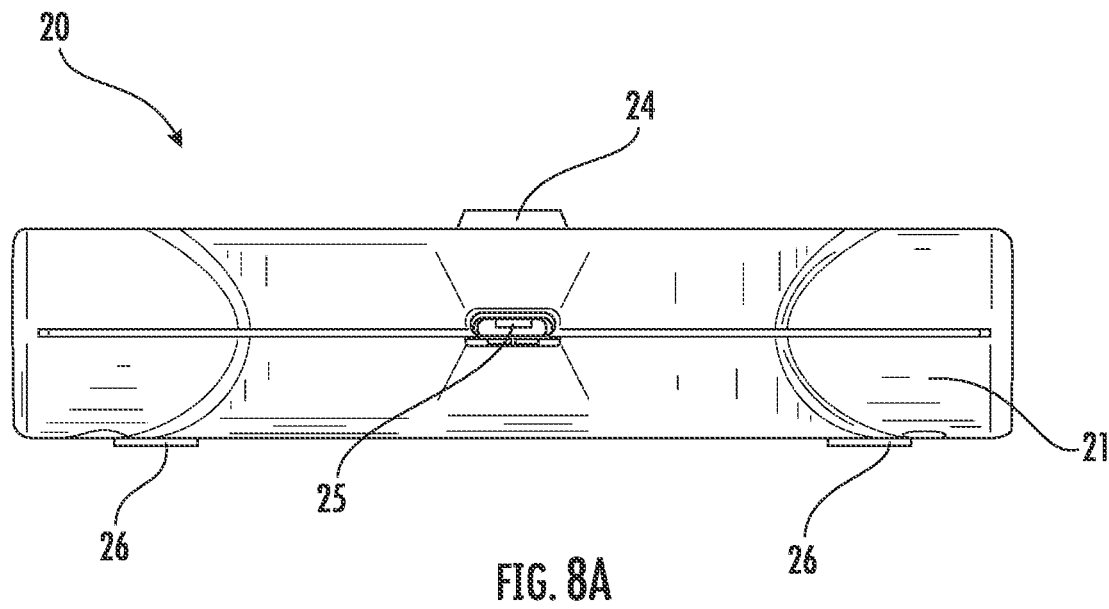
FIGS. 8A and 8B are front and back views respectively of a base station in accordance with certain embodiments of the invention.
Figure 8B:
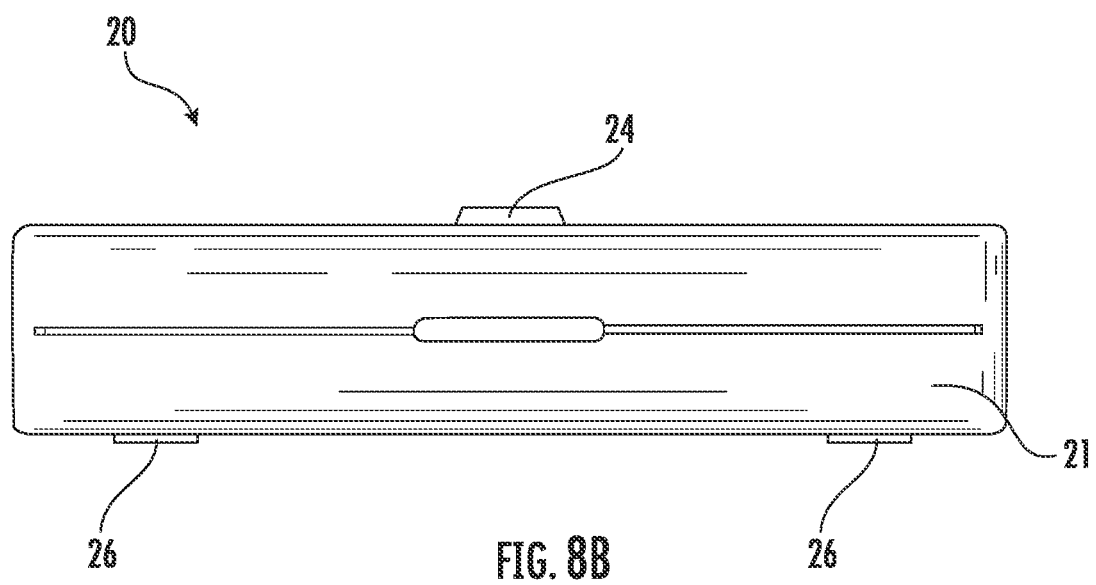
Figure 9A:
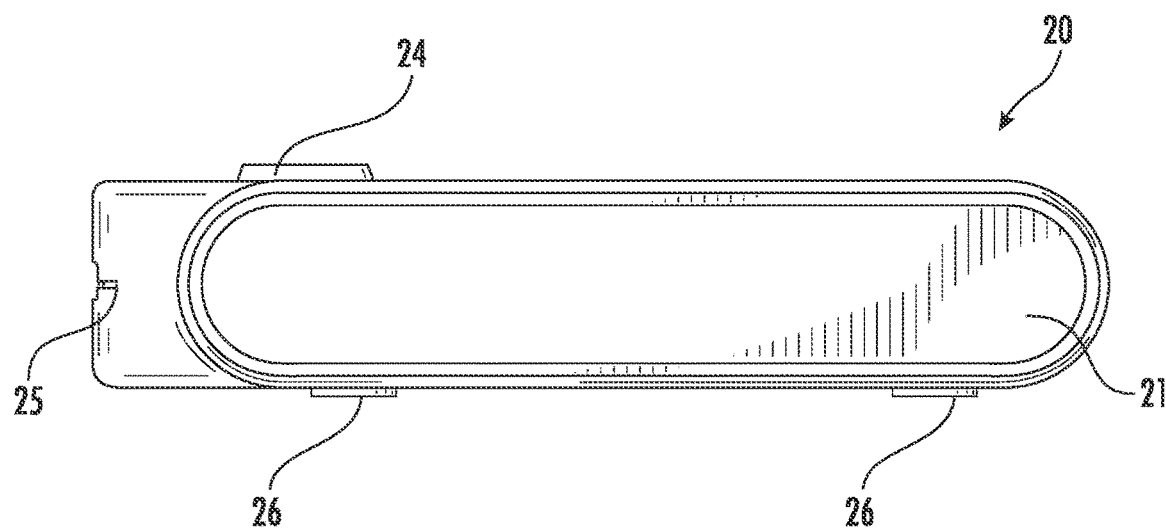
FIGS. 9A and 9B are side views of a base station in accordance with certain embodiments of the invention.
Figure 9B:
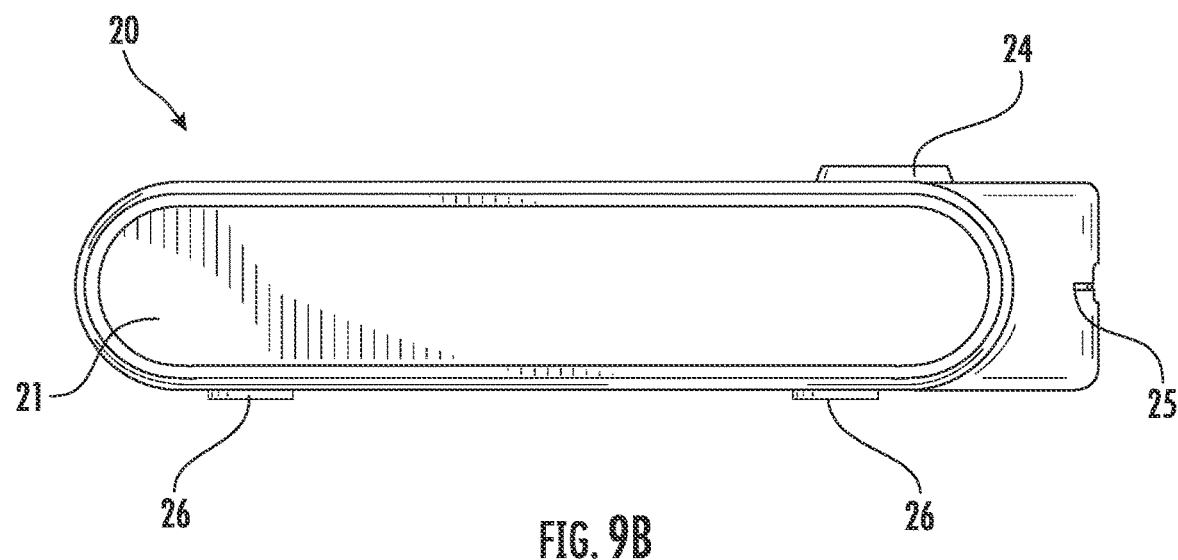
Figure 10A:
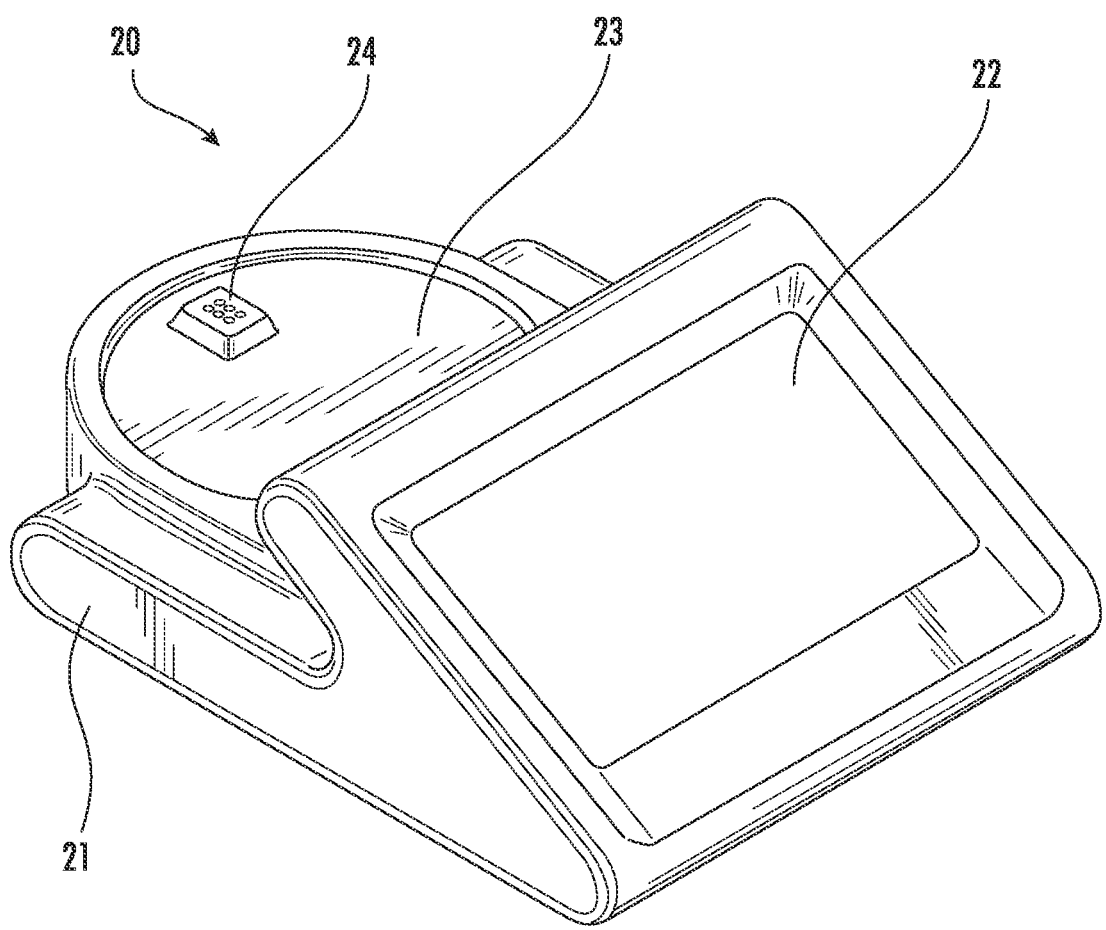
FIGS. 10A and 10B are perspective views of a base station including a display screen in accordance with certain embodiments of the invention.
Figure 10B:
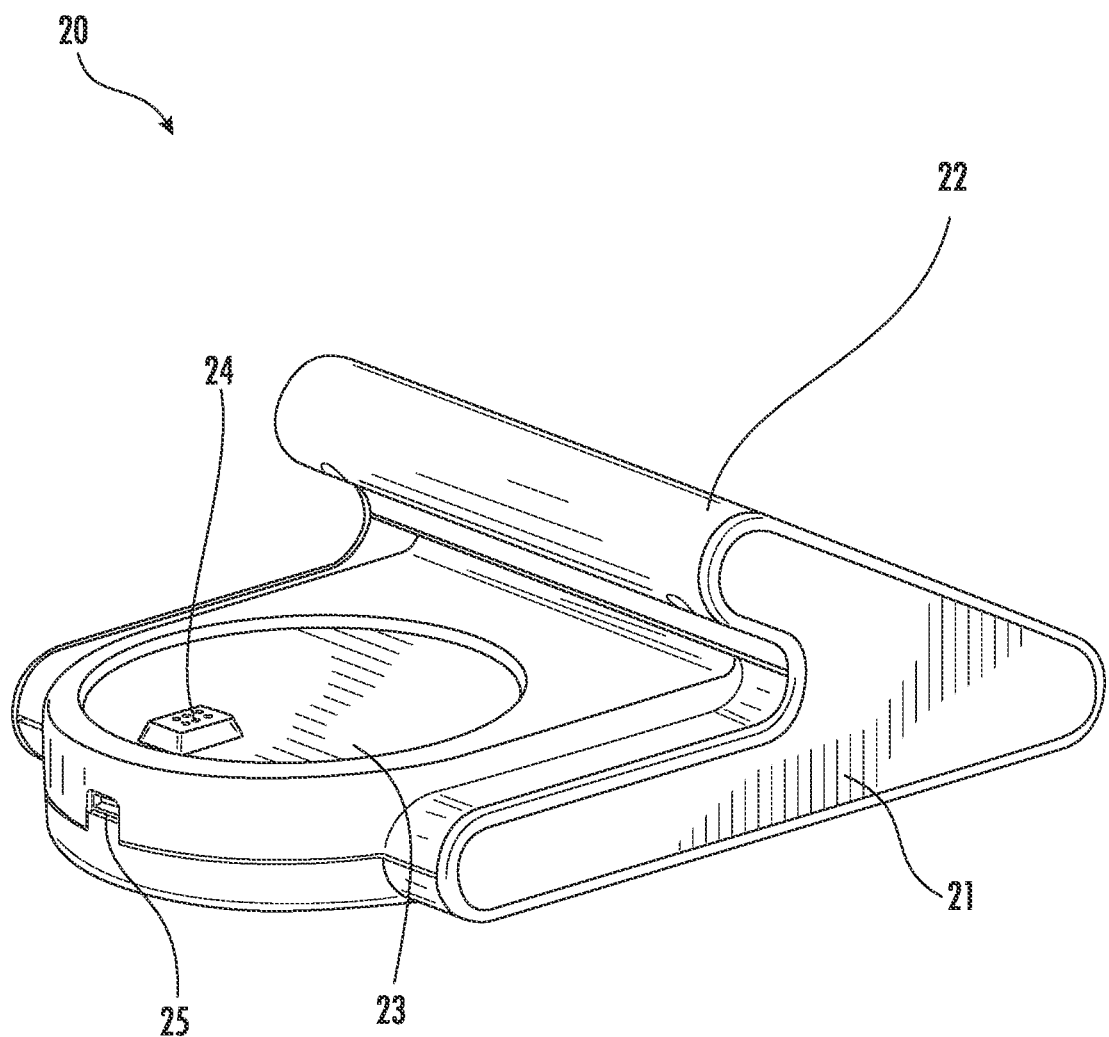
Figure 11:
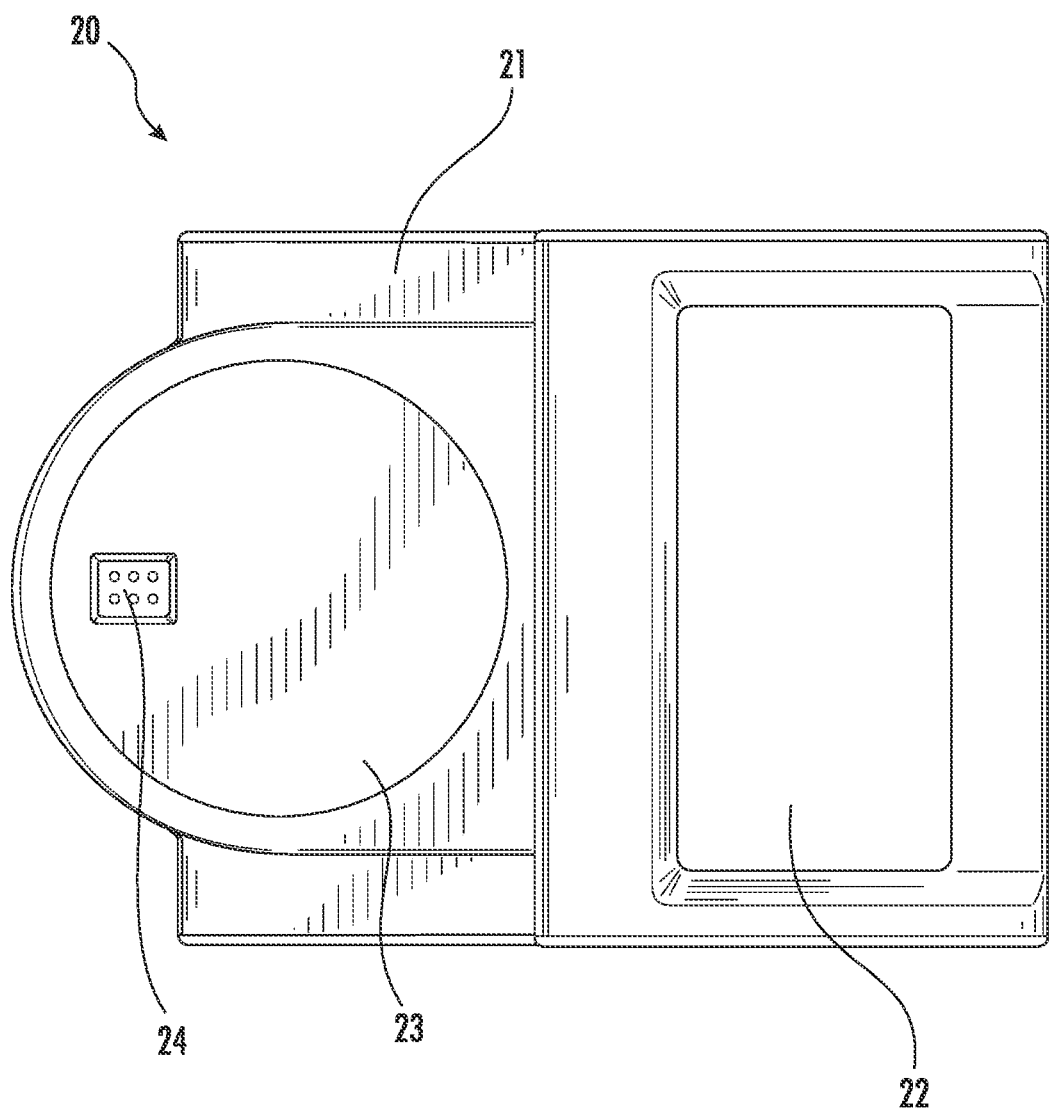
FIG. 11 is a top view of a base station including a display screen in accordance with certain embodiments of the invention.
Figure 12:
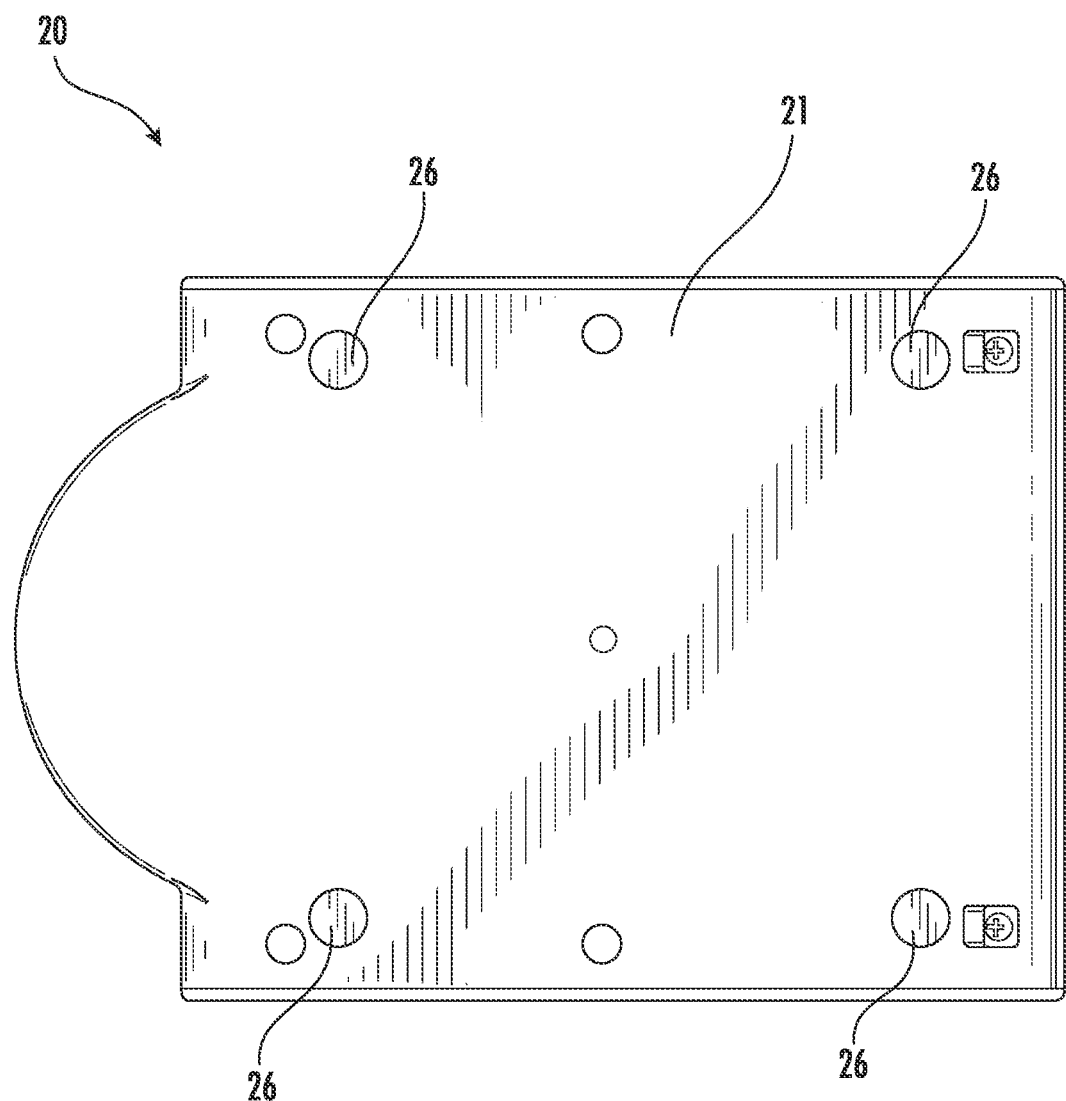
FIG. 12 is a bottom view of a base station including a display screen in accordance with certain embodiments of the invention.
Figure 13:
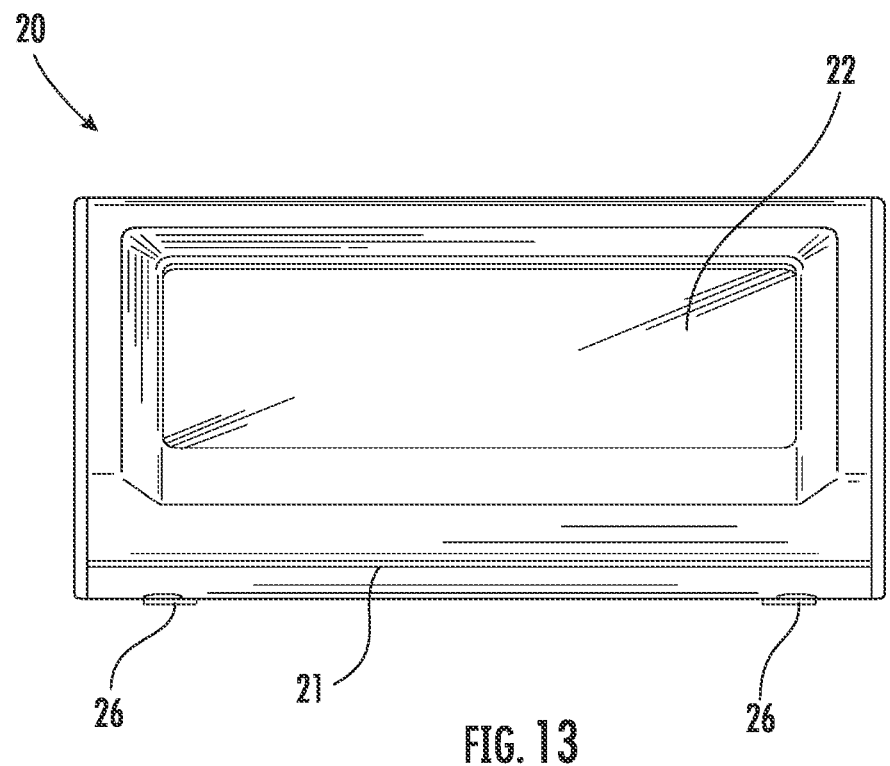
FIG. 13 is a front view of a display screen on a base station in accordance with certain embodiments of the invention.
Figure 14:
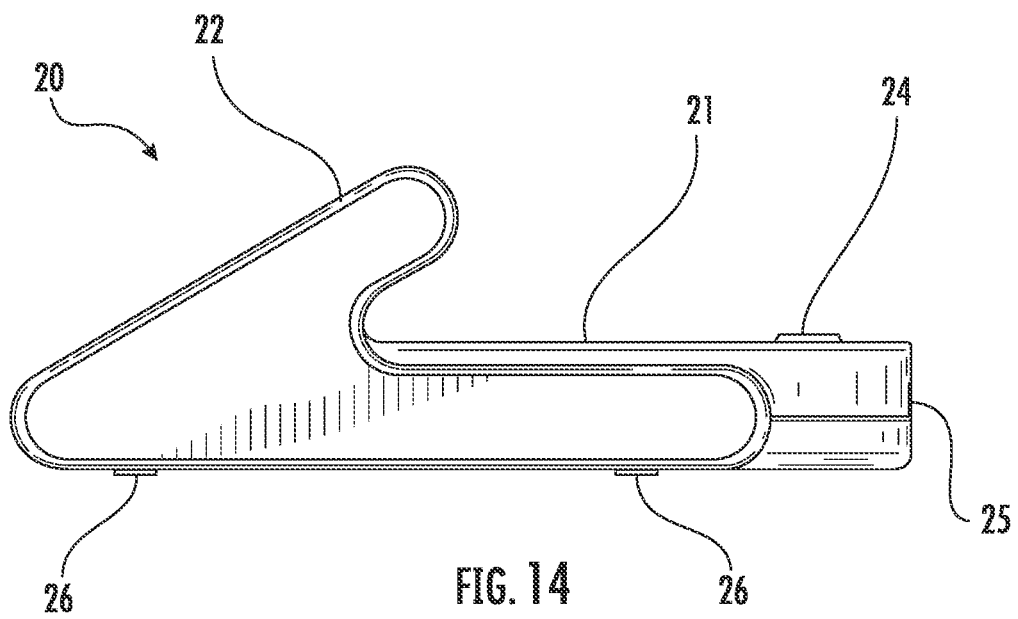
FIG. 14 is a side view of a base station including a display screen in accordance with certain embodiments of the invention.

In accordance with certain embodiments, the handheld unit 10 may have an angled top 11 and a substantially flat bottom 12. In some embodiments, for instance, the handheld unit 10 may have a substantially hourglass shape. In such embodiments, for example, the angled top 11 may be narrower than the bottom 12. For example, FIGS. 3A, 3B, and 4 are perspective views of the handheld unit 10 in accordance with certain embodiments of the invention. In this regard, the handheld unit 10 may be easily gripped by a user's hand to provide comfort and to prevent drops and spills during use. The handheld unit 10 may also include a membrane switch 15 on the back of the handheld unit 10. Membrane switch 15 may be used as a button to interact with at least the handheld portion 10 (and also possibly the base station 20 or computing device having a user interface 130, as described in more detail below) in order to for example, accept a reading or zero a reading if held down for a given amount of time (e.g., 3 seconds).

Moreover, as shown in various views in FIGS. 1-4 and 16, the handheld unit 10 may also include an optical test platform 13. The optical test platform 13 may have an open top configured to receive at least two sample tubes 14 positioned within a bottom portion (not shown) positioned within the handheld unit 10 such that the sample tubes 14 extend above the angled top 11 when inserted in the optical test platform 13. In this regard, in combination with the illumination light 33 shown in FIG. 15, the angled top 11 allows a user to visually inspect a sample contained in at least one of the sample tubes 14 and illuminated by the illumination light 33. The illumination light 33 may comprise a light emitting diode (LED) or other light source and may be configured to emit light upwardly into the sample contained in at least one of the sample tubes 14. Moreover, the illumination light 33 may emit light according to a light modulation pattern. Further details regarding the operation of the illumination light 33, and corresponding methods of using and reducing interference from the illumination light, are discussed further below and may be found in U.S. Provisional Application No. 62/487,736, entitled "Method, Apparatus, and Computer Program for Controlling Components of a Detection Device," and filed Apr. 20, 2017, which application is incorporated by reference herein in its entirety.

Figure 15:
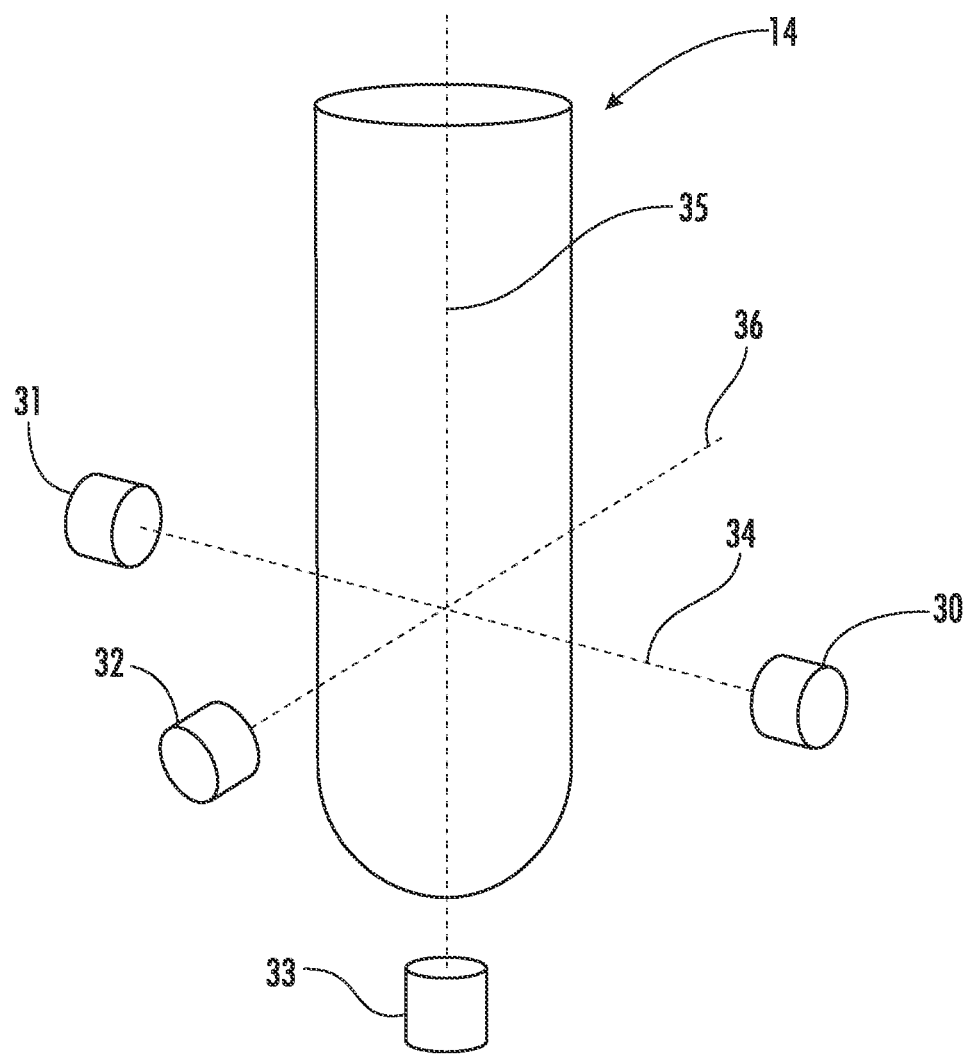
FIG. 15 illustrates a sensor network positioned around a sample tube in accordance with certain embodiments of the invention.

FIG. 15 also illustrates a sensor network 190 and various light sources 30, 33 and detectors 31, 32 positioned around a sample tube 14 in accordance with certain embodiments of the invention. As shown in FIG. 15, the emitter 30 may be positioned within the handheld unit 10 proximate a center-bottom portion of the optical test platform 13 such that the emitter 30 substantially aligns at least one of the at least two sample tubes 14 when the sample tubes 14 are inserted in the optical test platform 13 (e.g., with a vertical section of the wall of at least one of the sample tubes 14). The emitter 30 may be any type of device configured to emit a signal for detection by a sensor. The signal emitted by emitter 30 may include but is not limited to infrared (IR) wavelengths, near-infrared (NIR) wavelengths, electromagnetic radiation, and/or other types of light (including visible and/or non-visible light). For example, in some embodiments, the emitter 30 may be an LED, infrared LED and/or the like. For simplicity, the signal emitted by emitter 30 may be referred to herein as a "source light" or "emitted light," but it will be appreciated that any of the aforementioned signal types may be employed.

The emitter 30 may emit the source light according to a light modulation pattern. In the illustrated embodiment of FIG. 15, one emitter 30 and two sensors 31, 32 are used to generate an accurate turbidity measurement of the sample. In operation, the emitter 30 may transmit light into the sample and a portion of the transmitted light passes through the sample to a first sensor 31 (e.g., a density sensor) positioned opposite the emitter 30 relative to the sample tube 14, while a second portion of the transmitted light reflects off of the sample and is collected by a second sensor 32 (e.g., a nephelometric sensor) perpendicular to the transmission direction of the emitter 30. In particular, the density sensor 31 (which may be considered an optical density sensor) may be configured to measure a mass of microorganisms or other matter in a liquid suspension based on an amount of source light that passes through the sample tube and is detected by the density sensor 31, and the nephelometric sensor 32 may be configured to measure a concentration of suspended particles in the sample.

Moreover, the density sensor 31 may be oriented collinearly relative to the axis 34 of the emitter 30 and may be oriented 180 degrees offset from the emitter 30 with respect to the axis 35 of the sample tube 14, such that when a sample tube is inserted, the emitter 30 is positioned on the opposite side of the tube from the density sensor 31. The nephelometric sensor 32 may be positioned 90 degrees about the radial circumference of the sample tube 14 from both the emitter 30 and density sensor 31 on an orthogonal axis 36 to collect reflected light. The emitter 30 may be configured to transmit the source light perpendicular to the surface of the sample tube 14 through the longitudinal axis 35 of the sample tube 14. The optical density instrument 1 may then combine the signals from each sensor 31, 32 to generate an optical measurement (e.g., turbidity) of the sample.

One readout for this measurement of turbidity and/or concentration of microorganisms in the liquid that can be obtained is known as a McFarland value. This McFarland value is obtained using a series of McFarland standards, which are a series of known concentrations of solutions that are used to prepare a standard curve in order to determine the concentration of particles in an unknown sample. Density sensor 31 and nephelometric sensor 32 are provided merely as example sensors, and may be optional in some embodiments.

It will be appreciated that a variety of other types of sensors and/or receivers may be present and may be employed according to example embodiments. For example, the density sensor 31 and nephelometric sensor 32 may be any type of photodetector or other optical sensor, including, but not limited to, charge-coupled devices (CCD); active-pixel sensors (APSs) such as complementary metal-oxide-semiconductor (CMOS) sensors; reverse-biased LEDs, photodiodes, phototransistors, photoresistors, photomultipliers, or any other sensor capable of determining an intensity of incident light at the sensor.

Processing circuitry may, for instance, control operations of at least the emitter 30, the illumination light 33, and the at least one sensor to generate raw light data, convert the raw light data into optical density data, and communicate the optical density data to the display screen 22. Further details regarding the operation of the sensors, including calibration, zeroing, and data collection, are discussed below and may be found in U.S. Provisional Application No. 62/487,736, entitled "Method, Apparatus, and Computer Program for Controlling Components of a Detection Device," and filed Apr. 20, 2017, which application is incorporated by reference herein in its entirety.

Figure 16:
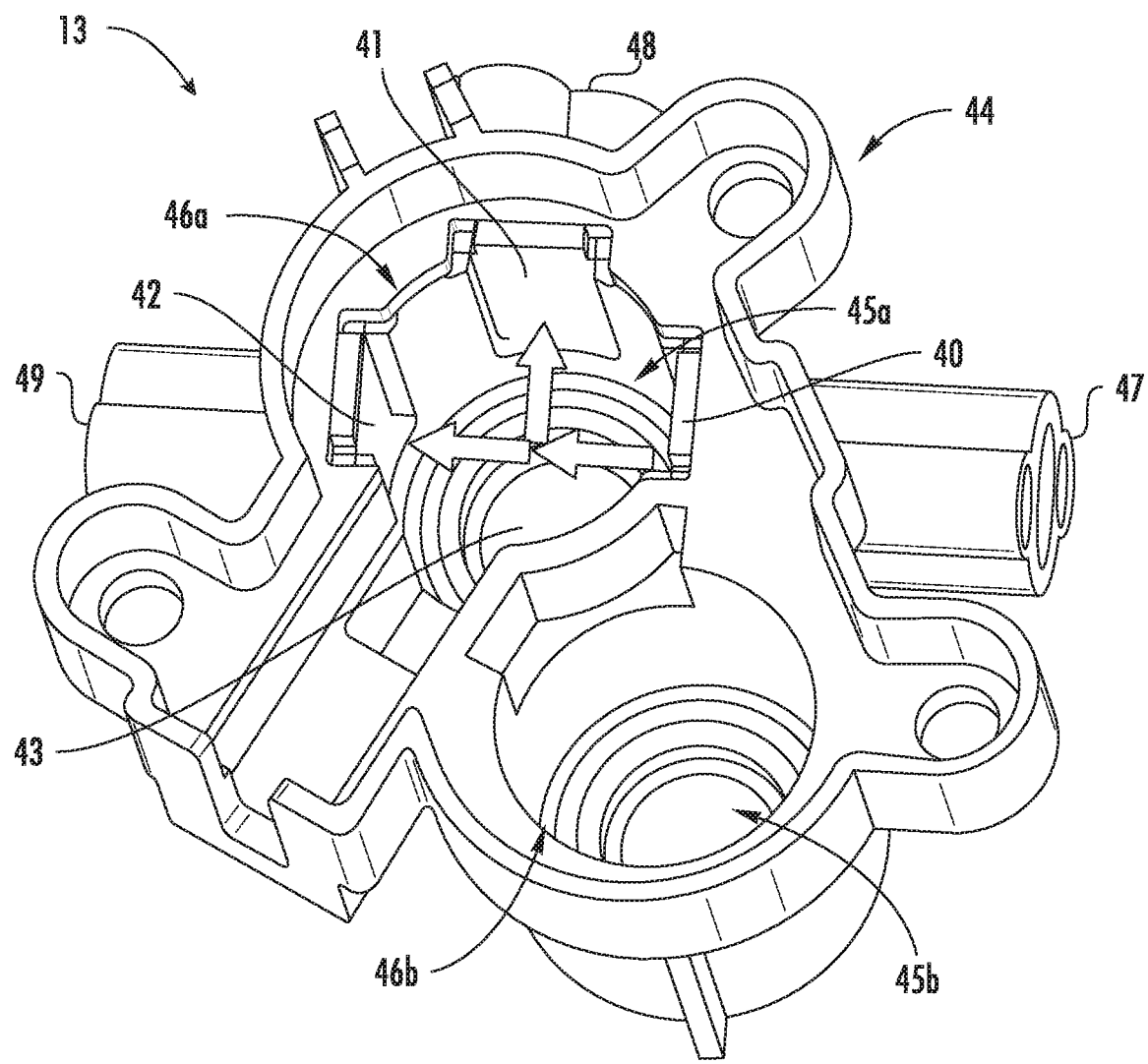
FIG. 16 is a perspective view of an optical test platform showing the optical paths of light traveling through the optical test platform in accordance with certain embodiments of the invention.
Figure 17:
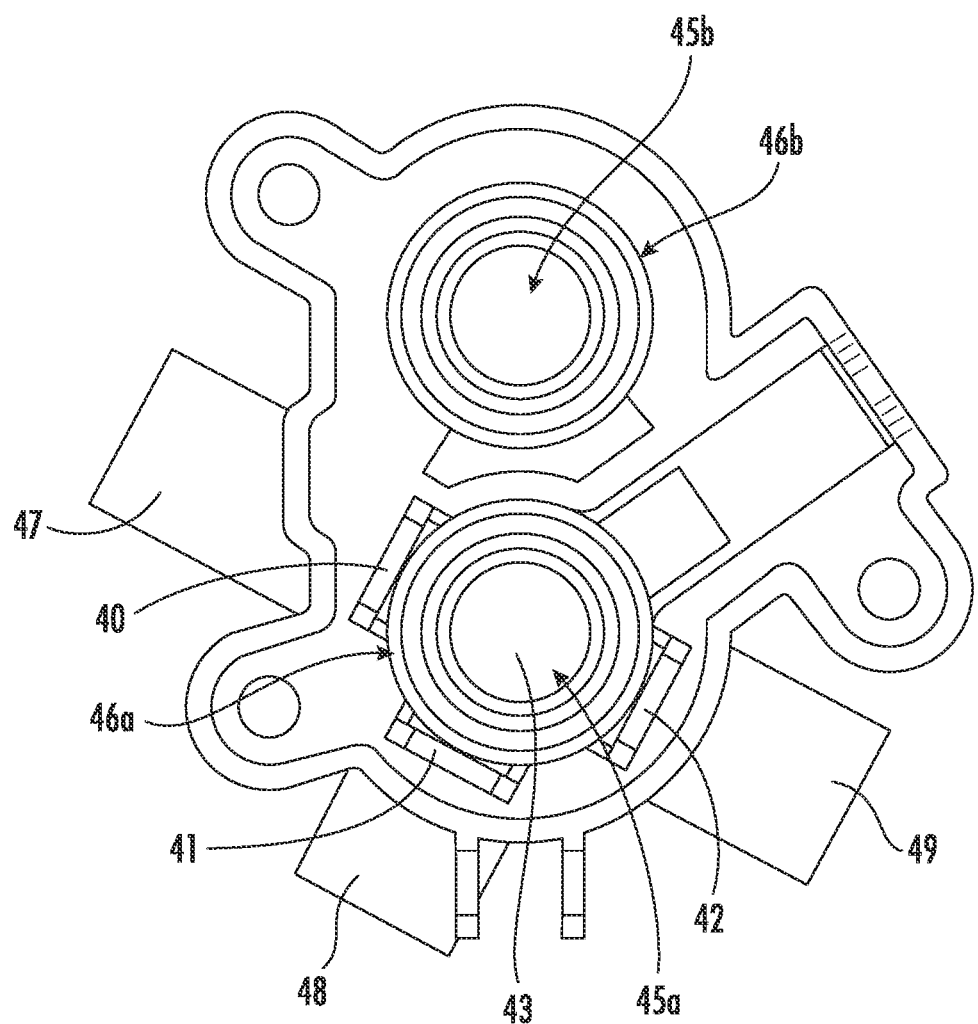
FIG. 17 is a top view of an optical test platform in accordance with certain embodiments of the invention.

FIGS. 16 and 17 show various views of the optical test platform 13. With reference to FIG. 16, a perspective view of the optical test platform 13 is shown in accordance with certain embodiments. The optical test platform 13 may include separate windows 40, 41, 42, 43 embedded into the shell 44 of the test platform 13, and the shell 44 may be molded of an opaque or semi-opaque material (e.g., a black polymer). The windows 40, 41, 42, 43 allow light travelling to and/or from the emitters, detectors, and illumination lights discussed herein to pass through the shell 44 at generally perpendicular angles to the surface of the window, with the shell material prohibiting light from propagating through the shell itself. The shell 44 may define one or more cavities 45a, 45b (collectively "45") therein, and in some embodiments, the cavities may be bounded by one or more walls. The cavities 45 may receive the sample tubes 14 (shown in FIGS. 1-5) through an upper aperture 46a, 46b (collectively "46"), and the sample tubes 14 may be supported by the shell 44.

The shell 44 may hold any of several configurations of sample tubes 14. For example, in the depicted embodiment of FIG. 16, the shell 44 includes two cavities 45a, 45b configured to receive two corresponding sample tubes 14. The depicted embodiment is configured to test one of the two sample tubes 14 (e.g., in some embodiments, the optical components may only interrogate one of the two cavities, cavity 45a), while the second cavity is left for convenience to hold a second sample tube. This dual sample tube configuration is useful for use with a dual-sample tube or other fused sample tubes, where the two sample tubes should be kept together for study but need not be independently checked with optical density sensors. Although the description herein refers to interrogating a single sample tube, these teachings may be readily applied to a second set of optical components operating on the second cavity 45b. In some alternative embodiments, the optical test platform 13 may include only a single cavity for testing a single sample tube, or in some embodiments, greater than two sample tubes may be used with one, two, or more sets of optical components for interrogating the respective sample tubes.

The optical test platform 13 may include one or more mounts 47, 48, 49 for engaging and supporting the optical components (e.g., the emitter 30, first detector 31, and second detector 32 shown in FIG. 15). In the embodiments shown in FIGS. 15-17, the first mount 47 may receive and engage the emitter 30, the second mount 48 may receive and engage the second detector 32, and the third mount 49 may receive and engage the first detector 31. One of ordinary skill in the art will also appreciate that the mounts 47, 48, 49, emitter 30, sensors 31, 32, and illumination light 33 may be reconfigured to any arrangement that satisfies the possible emitter-detector relationships discussed herein.

Figure 34:
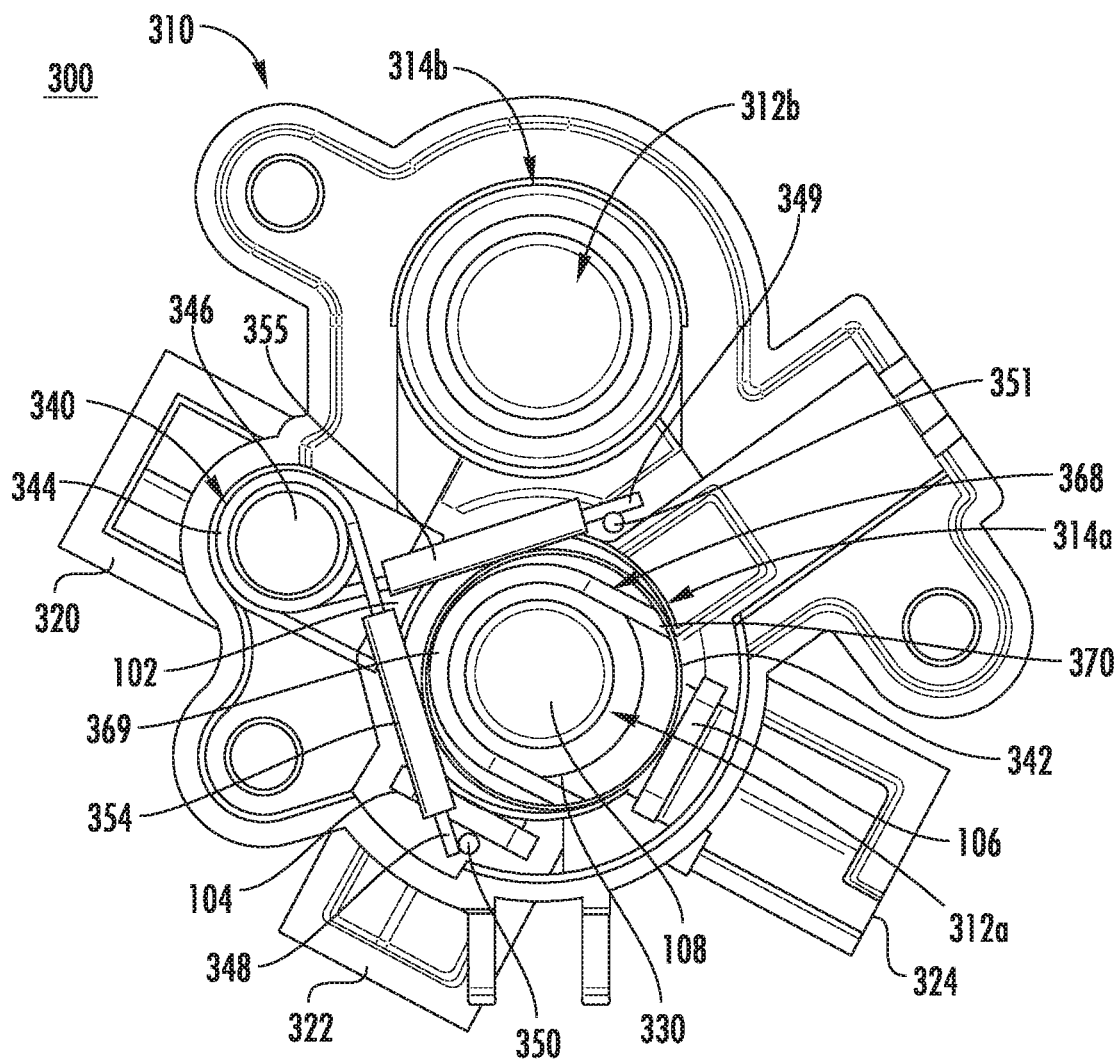
FIG. 34 is a top plan view of an optical test platform according to an example embodiment.

Turning to FIG. 34, a second embodiment of the optical test platform 300 is shown. The optical test platform 300 may include a shell 310 with one or more mounts 320, 322, 324; an aperture 330; upper apertures 314a, 314b; and cavities 312a, 312b that may each be structured and operate in substantially the same manner as the example optical test platforms 13, 800 detailed herein. Moreover, embodiments of the optical test platform 300, or portions thereof, may be incorporated into or substituted for portions of the optical test platforms 13, 800 detailed herein.

With continued reference to FIG. 34, the optical test platform 300 may include at least one spring 340 that urges a sample tube 342 to a predetermined position within one or more of the cavities 312a, 312b. In the embodiment depicted in FIG. 34, the optical test platform 300 includes a spring 340 configured to bias a sample tube 342 towards a window 106. The depicted spring 340 includes a coiled wire 344 disposed around a post 346 and two legs 348, 349 defining the respective ends of the wire.

The spring 340 may operate as a helical torsion spring, such that the helical coiled wire 344 is twisted about the axis of the coil (e.g., an axis extending perpendicular to the page of FIG. 34) by bending moments applied at the legs 348, 349. In such embodiments, the coiled wire 344 may elastically deform in response to a force on either or both legs 348, 349, and the coiled wire 344, when elastically deformed, may cause the legs 348, 349 to apply a force opposite the direction of the applied force. For example, the sample tube 342 may be inserted into the cavity 312a between the two legs 348, 349 which may cause an outward force (e.g., a force radially outward from the center of the cavity 312a) on the legs 348, 349 and a torsional torque on the coiled wire 344. The legs 348, 349 may apply an opposing inward force (e.g., a force radially inward towards the center of the cavity 312a) on the sample tube 342, caused by the torsional reaction torque of the coiled wire 344, which may push the sample tube toward the window 106.

In the depicted embodiment, the post 346 and spring 340 are disposed at the same side of the cavity 312a as the first mount 320, opposite the third window 106, to cause the spring to urge the sample tube 342 towards the third window as described herein. In some embodiments, the post 346 and spring 340 may be disposed at any other side of the cavity, including opposite the second window 104.

In some embodiments, a roller 354, 355 may be disposed on each of the respective legs 348, 349 of the spring 350, and the rollers 354, 355 may be slip fit or otherwise allowed to rotate about the legs 348, 349 to allow the sample tube 342 to move freely upwardly and downwardly (e.g., into and out of the page of FIG. 34). The legs 348, 349 may apply forces to the sample tube 342 perpendicular to the surfaces of the rollers 354, 355 (e.g., a force vector substantially intersecting a center of rotation of the rollers), while the rollers rotate when force is applied tangential to the surface of their surface. In this manner, gravity may retain the sample tube 342 vertically within the cavity 312a while still allowing the sample tube to be freely removed or inserted, and in the depicted embodiment, the spring 340 may hold at least a portion of the sample tube in position within the horizontal plane (e.g., the plane of the paper in FIG. 34). In some embodiments, the rollers 354, 355 may cause the legs 348, 349 to each apply a purely horizontal force to the sample tube 342. In some embodiments, the rollers 354, 355 may define generally hollow cylinders disposed about the legs 348, 349. In some embodiments, the rollers 354, 355 may be made from a low-friction material to prevent scratching the sample tube 342. For example, in some embodiments, the rollers 354, 355 may be made of PEEK (Polyether ether ketone), PTFE (Polytetrafluoroethylene), or Acetal (Polyoxymethylene).

Figure 35:
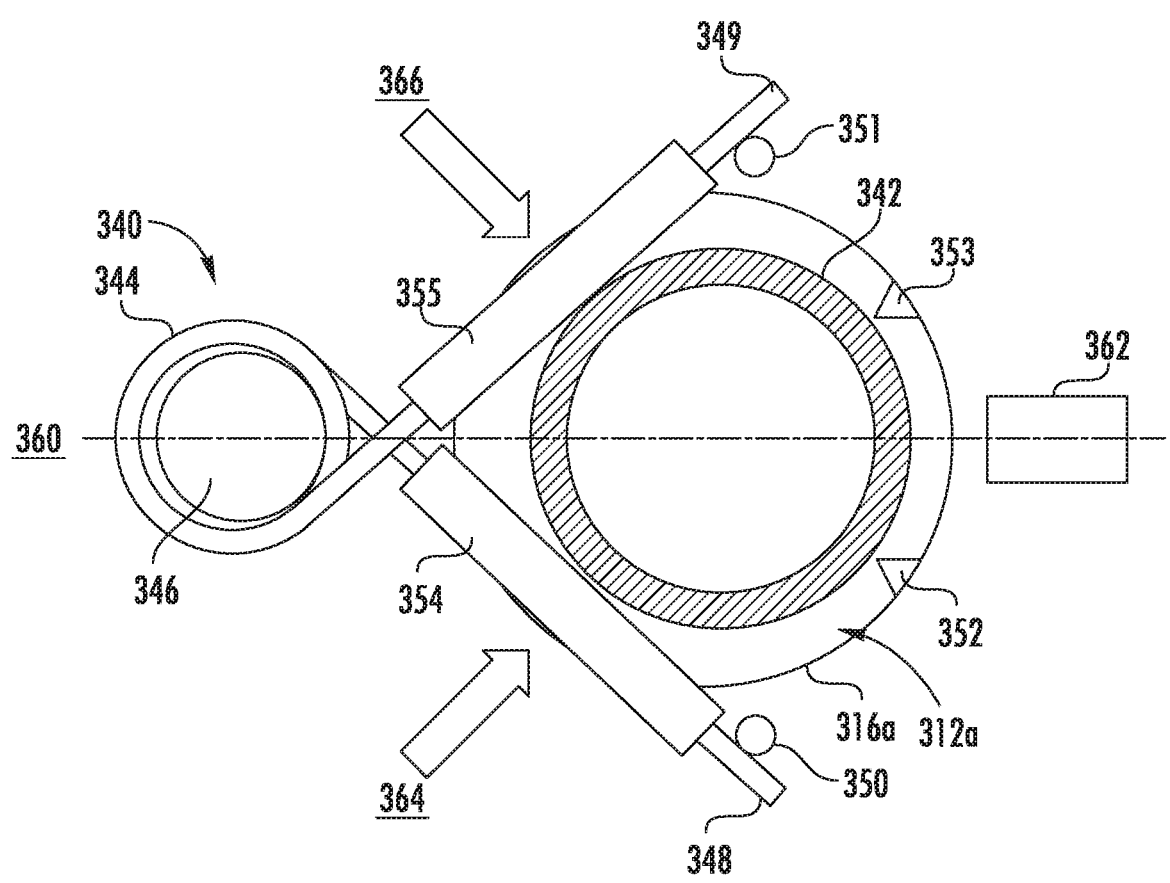
FIG. 35 is a not-to-scale simplified top plan view of an optical test platform according to an example embodiment.

With reference to FIG. 35, a simplified embodiment of the spring 340, sample tube 342, and surrounding components are shown for illustration purposes. In the depicted embodiment, the legs 348, 349 may apply forces 364, 366 on the sample tube 342 in directions that are at least partially towards a detector 362 (e.g., the first detector 31) and at least partially towards a center axis 360 bisecting the legs 348, 349. In some embodiments, the center axis 360 may extend between a diametric center of the post 346 and the detector 362. In some embodiments, the widthwise center of one or more windows (e.g., windows 40 and 42 shown in FIGS. 16-17) may be defined on the center axis 360. Although not shown in FIG. 35, a window (e.g., window 42 shown in FIGS. 16-17 and window 106 shown in FIG. 34) may be positioned between the sample tube 342 and the detector 362.

The cavity 312a may be bounded by a wall 316a of the optical test platform. In some embodiments, two or more alignment ribs 352, 353 may be disposed on the wall 316a of the cavity 312a to help position the sample tube 342 along the center axis 360. In some embodiments, the ribs 352, 353 may be molded as part of the shell 310. In the embodiment depicted in FIG. 35, the alignment ribs 352, 353 may hold the sample tube 342 in a predetermined position (e.g., the position shown in FIGS. 35-36) when the legs 348, 349 apply a force in any direction having a force component towards the detector 362. In this manner, the alignment ribs 352, 353 may provide a stable, repeatable position for the sample tube 342 without requiring a precise force vector from the legs 348, 349, and the ribs 352, 353 may guide the sample tube 342 into position, for example, to a position centered along the center axis 360. In some embodiments, the legs 348, 349 may be configured to apply a force to the sample tube 342 towards a point between the legs (e.g., an intersection point of the force vectors 364, 366), with the coiled wire 344 attempting to move the legs 348, 349 in counter-rotating directions about the axis of the helical spring.

The predetermined position of the sample tube 342 may be designed to facilitate a clear, repeatable interrogation of the sample tube using the techniques and apparatus described herein, and the predetermined position may be dependent on the diameter of the sample tube and the spacing between the ribs. In some embodiments, the ribs 352, 353 may be positioned at least at a vertical position of one of the legs 348, 349. In some embodiments, the ribs 352, 353 may be positioned below a vertical position of the legs 348, 349. In some embodiments, the ribs 352, 353 may be positioned between the vertical positions of the legs 348, 349. In some embodiments, the ribs 352, 353 may be positioned at the vertical position of both legs 348, 349. In some embodiments, the legs 348, 349 may disposed on or may apply a force in a horizontal plane, such that the line of action of the spring is on a horizontal plane relative to the optical test platform 300. In some embodiments, the ribs 352, 353 may extend substantially the height of the cavity 312a.

In operation, the sample tube 342 is inserted into the cavity 312a of the optical test platform 310 (shown in FIG. 34). As the sample tube 342 is inserted, the legs 348, 349 are pushed away from the center axis 360 as the rollers 354, 355 allow the sample tube to slide into the cavity 312a. The torque created by the elastic deformation of the coiled wire 344 of the spring 340 may cause each leg 348, 349 to apply a force 364, 366 on the sample tube 342. Each of the forces 364, 366 of the legs 348, 349 may be in a direction that is at least partially towards the center axis 360 and at least partially towards the detector 362.

In some embodiments, the components of the forces 364, 366 that are perpendicular to the center axis 360 may cancel, leaving a net force on the sample tube 342 along the center axis 360 towards the detector 362. The spring 340 may apply a reaction force on the post 346 at a point closest to the detector 362 on the center axis 360. In some embodiments, as described below, the legs 348, 349 may be vertically offset such that there is a slight torque applied to the sample tube 342, and this torque may be counteracted by the structure of the optical test platform (e.g., the ribs 352, 353 and/or guide surface 368). The sample tube 342 may be held vertically within the cavity 312a between the various contact points described herein.

In some embodiments, the spring 340 (shown in FIGS. 34-36) and alignment structures 352, 353, 368 may be configured to position the sample tube 342 (shown in FIGS. 34-35) adjacent the third window 106 such that the density signal (e.g., the portion of the source light that passes through the sample tube towards the density sensor) is incident upon the sample tube 342 and window 106 perpendicular to their respective surfaces. In such embodiments, the spring 340 may be positioned opposite the window 106 as shown in FIG. 34. In such embodiments, the emitted light may also be incident upon the sample tube perpendicular to its surface, and the emitted light and density signal may travel at least partially along the center axis 360 shown in FIG. 35 (e.g., the detector 362 may receive the density signal 154). In some embodiments, the spring 340 may position the sample tube 342 closer to the third window 106 than to the first window 102 or second window 104, such that in some embodiments the surface of the sample tube may not align with the second window 104 to transmit the nephelometric signal 152 perpendicularly through both surfaces. As detailed herein, in some embodiments, the spring 340 may be configured to position the sample tube adjacent any of the first, second, or third windows, with the alignment ribs on either side of any of the aforementioned windows and the spring opposite any of the aforementioned windows.

When no sample tube 342 is inserted in the cavity 312a, the legs 348, 349 of the spring 340 may engage respective stops 350, 351 on the optical test instrument 310 (shown in FIG. 34). In some embodiments, the stops 350, 351 may be positioned equidistant from the center axis 360 such that the legs 348, 349 remain centered relative to the axis 360 to receive the sample tube 342 therebetween. In some embodiments, the stops 350, 351 may be configured to engage the legs 348, 349 such that the spring 340 is always elastically deformed when positioned on the post 346. In such embodiments, spring 340 may apply a force to the stops 350, 351 when not otherwise obstructed or resisted by the sample tube 342, and the continuous deformation may help create a smooth motion in the spring 340 without slop or slack in the motion or application of force. In some embodiments, the legs 348, 349 may be disposed perpendicular to each other when the legs are engaged with the respective stops 350, 351. In some embodiments, the stops 350, 351 may be positioned such that the legs 348, 349 and rollers 354, 355 protrude vertically over the cavity 312a when no sample tube 342 is inserted. In some embodiments, the stops 350, 351 may be positioned such that the legs 348, 349 and rollers 354, 355 protrude less than half way over the cavity 312a when no sample tube 342 is inserted. In some embodiments, the spring 340 may be positioned between the shell 310 of the optical test platform and the outer housing of the instrument (shown in FIG. 1).

In some embodiments, the stops 350, 351 may be positioned such that, when a sample tube 342 is inserted into the cavity and is held against the ribs 352, 353, the legs 348, 349 comes into contact with the stops. In some embodiments, the sample tube 342 may prevent the legs 348, 349 from contacting the stops 350, 351 when in the predetermined position. In some embodiments, the legs 348, 349 may apply a force (e.g., forces 364, 366) to the sample tube 342 both before and while the sample tube is in the predetermined position against the ribs 352, 353.

Figure 36:
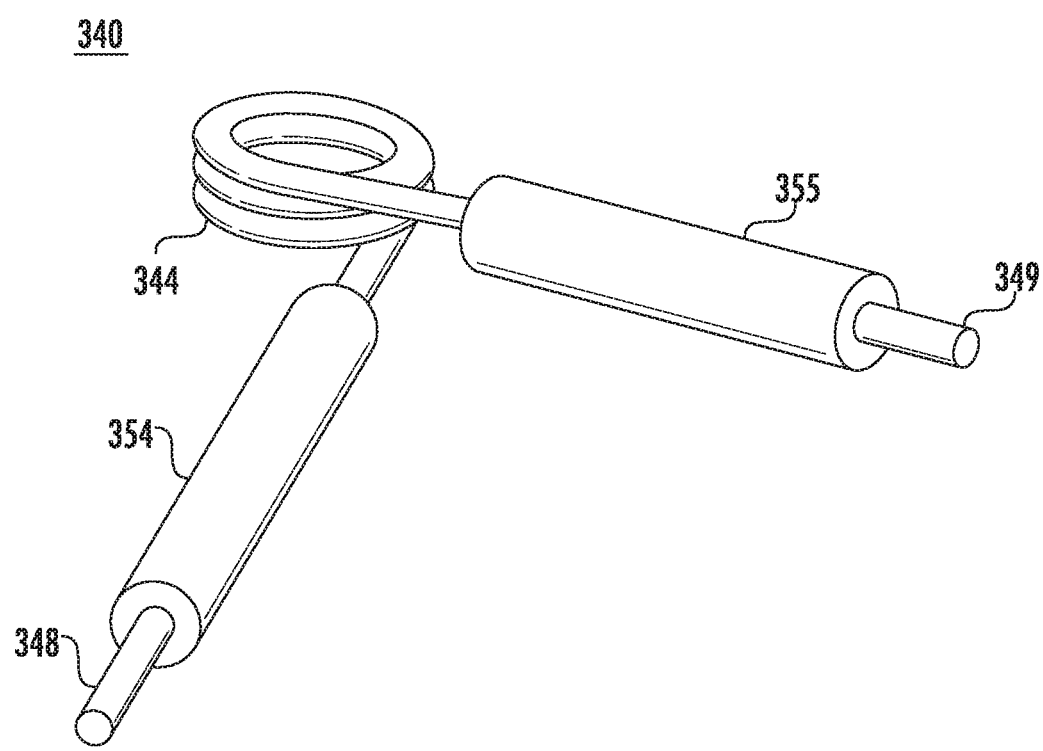
FIG. 36 is a perspective view of a spring with rollers according to an example embodiment.

Turning to FIG. 36, a perspective view of an embodiment of the spring 340 is shown. In the depicted embodiment, the legs 348, 349 cross each other near the coiled portion of the wire 344. As shown in FIG. 35, the cross over may occur along the center axis 360. Outward force on the legs 348, 349 away from the center axis 360 may cause the coiled wire 344 to torsionally tighten and compress in the depicted embodiment.

Turning back to FIG. 36, the legs 348, 349 may be vertically separated from each other due to the thickness of the spring 340 in the axis of the helical coil, which may cause one leg (e.g., the uppermost leg 349) to protrude over the cavity (e.g., cavity 312a shown in FIGS. 34-35) at a higher position than another leg (e.g., lowermost leg 348). In such embodiments, a torque may be applied to the sample tube 342 in a direction within the horizontal plane (e.g., the plane of the paper in FIGS. 34-35) attempting to move the sample tube out of vertical alignment, and the torque may be counteracted by the structures and guiding surfaces of the optical test platform described herein. In some embodiments, the legs may be bent or otherwise reoriented in another direction while still being able to apply force to the sample tube.

With reference to FIG. 34, in some embodiments, the lower end of the cavity 312a, proximate the lower window 108, may define a U-shaped guide surface 368 oriented with a curved portion 369 defining a semi-circle and a pair of straight portions 370 extending to either side of a window 106. In the depicted embodiment, the curved portion 369 of the guide surface 368 is disposed on the same side of the cavity 312a as the post 346 and majority of the spring 340 such that the force (e.g., forces 364, 366 shown in FIG. 35) of the spring 340 pushes the sample tube 342 along the U-shaped guide surface 368 towards the alignment ribs (e.g., alignment ribs 352, 353 shown in FIG. 35). The U-shaped guide surface 368 may be disposed above the lower window 108, which window may function and be structures according to the embodiments described herein.

The sample tube 342 may engage the guide surface 368 and hold the sample tube upright and vertical against the alignment ribs (e.g., alignment ribs 352, 353 shown in FIG.

35). In some embodiments, the sample tube 342 may have a curved, hemispherical bottom which may rest against a complementarily angled surface of the guide surface 348. The curved portion of the guide surface 368 may define a center of curvature that is offset from the center of the lower window 108 and the center of the cavity 312a, such that the sample tube is positioned closer to a window 106 opposite the spring 340 and post 346 than to the windows 102, 104 on the other surfaces of the wall 316a of the cavity. The guide surface 368 and alignment ribs 352, 353 may cooperate to hold the sample tube 342 substantially vertically within the cavity 312a and may cooperate to hold the sample tube parallel to the wall 316a of the cavity. The curved portion 369 and straight portions 370 may provide a counteracting force to the torque of the offset legs 348, 349 on the embodiment of the spring 340 and sample tube 342 described above.

Turning to FIGS. 37-45 another embodiment of the optical test platform 800 is shown. The optical test platform 800 may include a shell 810 with one or more mounts 820, 822, 824; an aperture 830; upper apertures 814a, 814b; and cavities 812a, 812b that may each be structured and operate in substantially the same manner as the example optical test platforms 13, 300 detailed above. Moreover, embodiments of the optical test platform 800, or portions thereof, may be incorporated into or substituted for portions of the optical test platforms 13, 300 detailed herein. In some embodiments, a first cavity 812a may be used for testing and/or operating on the fluid in a sample tube, while the second cavity 812b includes no testing windows or detectors.

With continued reference to FIG. 34, the optical test platform 800 may include at least one spring 840 that urges a sample tube 842 to a predetermined position within one or more of the cavities 812a, 812b. The spring 840 may include rollers 854, 855 that operate in substantially the same manner as the rollers 354, 355 detailed above. In the embodiment depicted in FIG. 34, the optical test platform 800 includes a spring 840 configured to bias a sample tube 842 towards a window 806. The depicted spring 840 includes a coiled wire 844 disposed around a post 846 (shown in FIG. 38) and two legs 848, 849 defining the respective ends of the wire. The spring 840 may operate as a helical torsion spring, such that the helical coiled wire 844 is twisted about the axis of the coil (e.g., an axis extending perpendicular to the page of FIG. 34) by bending moments applied at the legs 848, 849.

Figure 37:
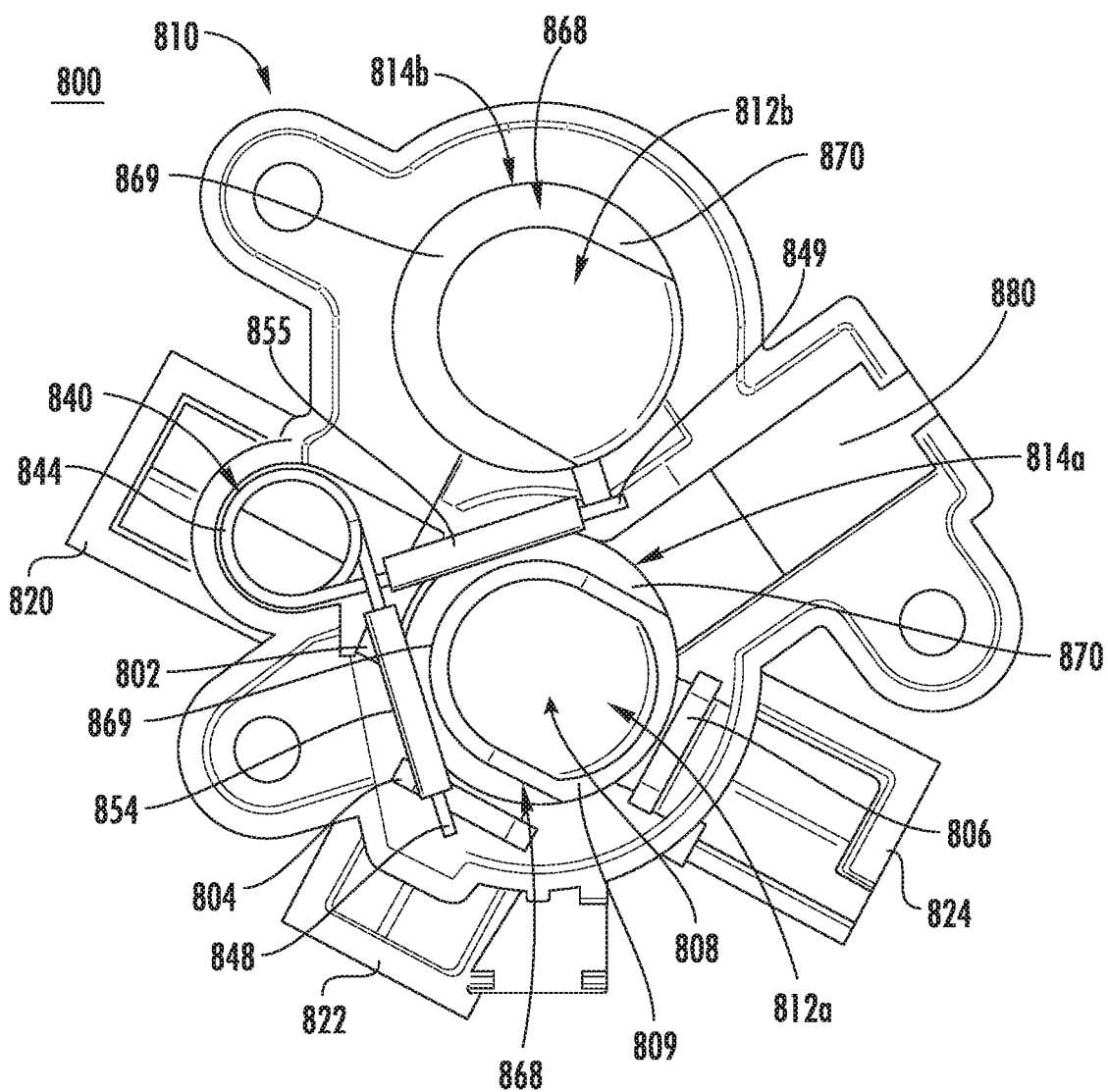
FIG. 37 is a top plan view of an optical test platform according to an example embodiment.
Figure 38:
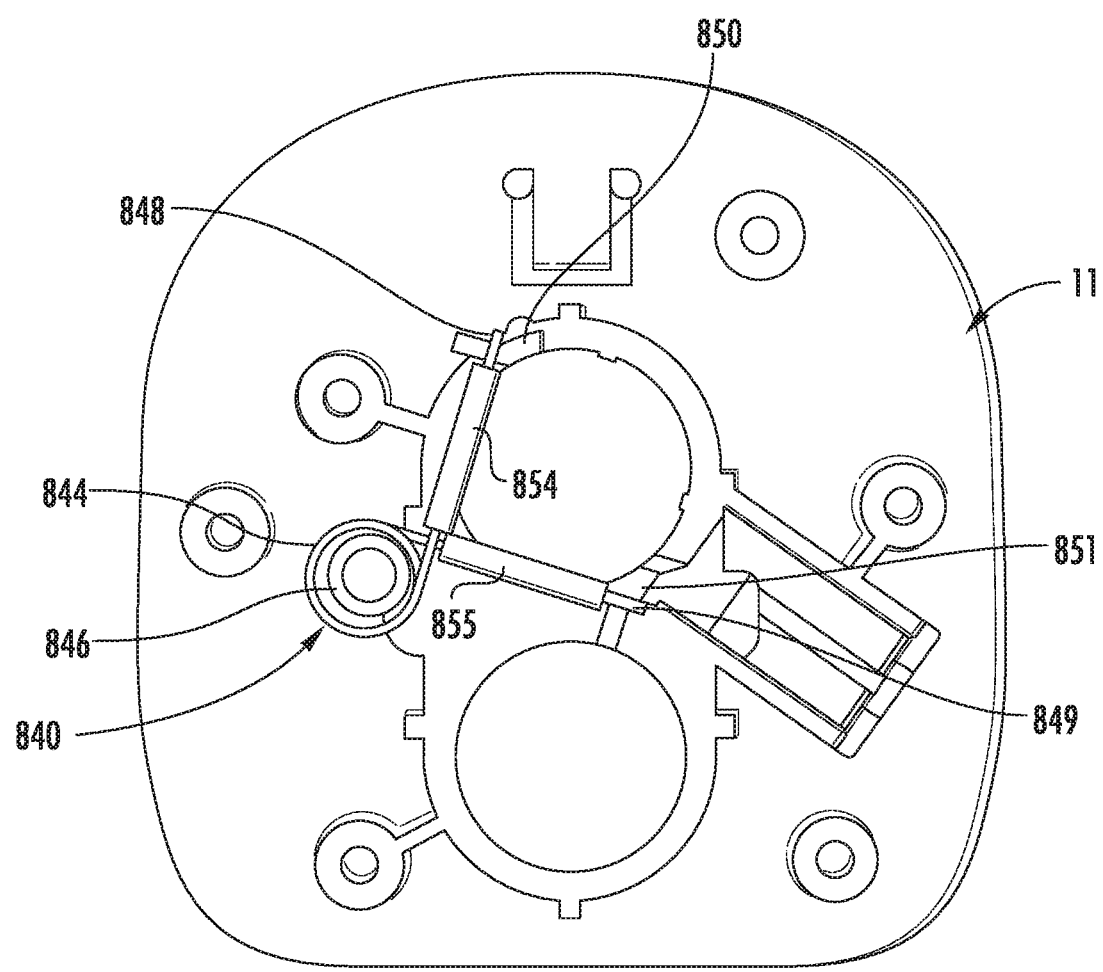
FIG. 38 is a bottom plan view of a housing for an optical density instrument according to an example embodiment.

With reference to FIG. 38, an example underside of a portion (e.g., the angled top 11) of the housing of the handheld unit of an optical test instrument (e.g., handheld unit 10 of optical test instrument 1 shown in FIG. 1) is depicted. In the depicted embodiment, the portion of the housing (e.g., the angled top 11) has a post 846 and a pair of stops 849, 850 extending downwardly therefrom towards the optical test platform (e.g., optical test platform 800 shown in FIG. 37). In some embodiments, the portion of the housing may be an insert that fits within the angled top 11 (e.g., along the part line on the angled top 11 shown circumferentially around the sample tubes 14 in FIG. 1) The post 846 and stops 849, 850 may each be structured and operate in substantially the same manner as the post 346 and stops 349, 350 detailed above, except that some or all of the post and stops may be attached to the portion 11 of the housing of the handheld unit instead of the optical test platform. The post and stops may be interchanged, such that a post 846 may be attached to the portion of the housing, while one or more of the stops 349, 350 are attached to the optical test platform, or vice versa.

Figure 39:
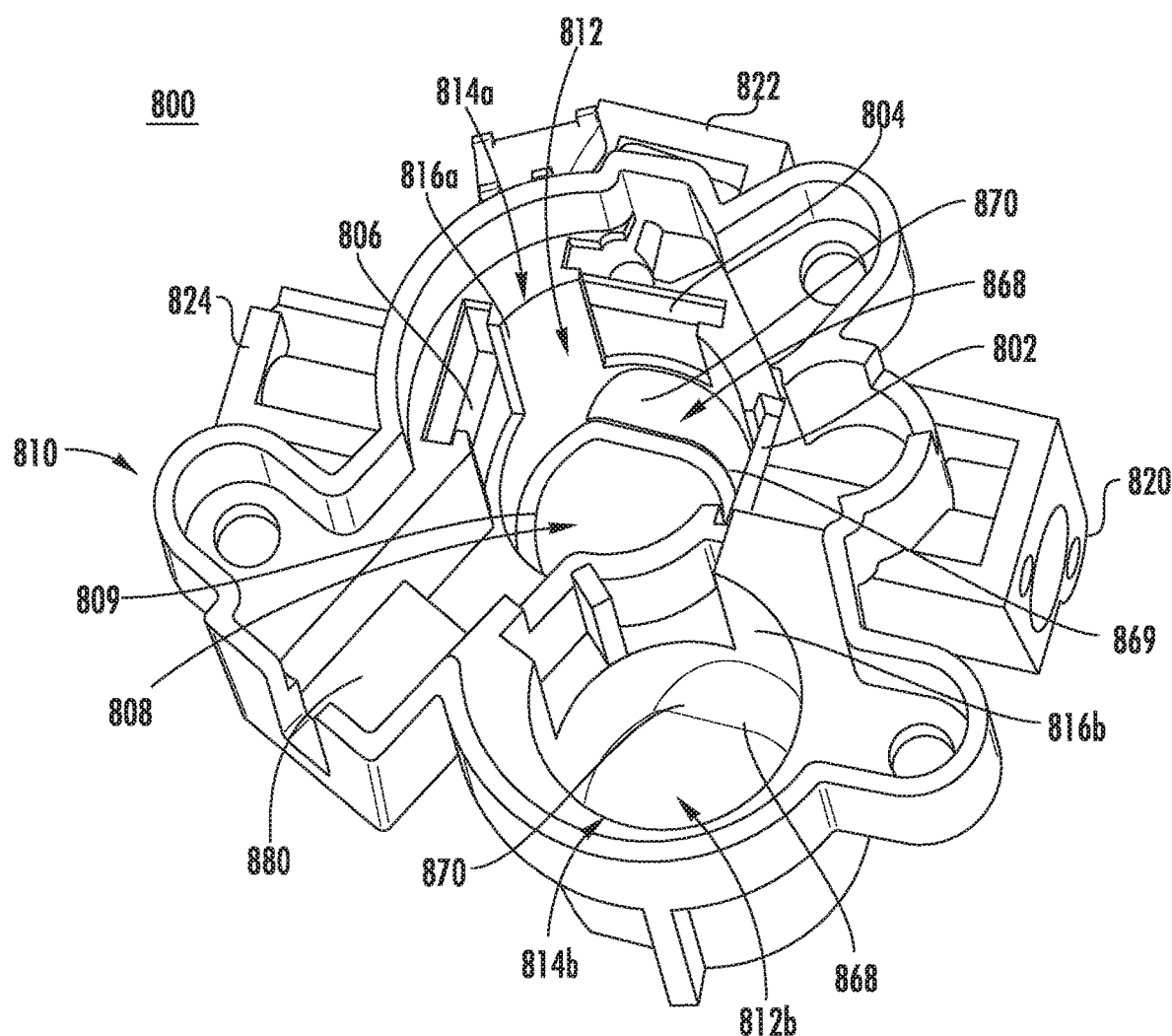
FIG. 39 is a perspective view of the optical test platform of FIG. 37.
Figure 40:
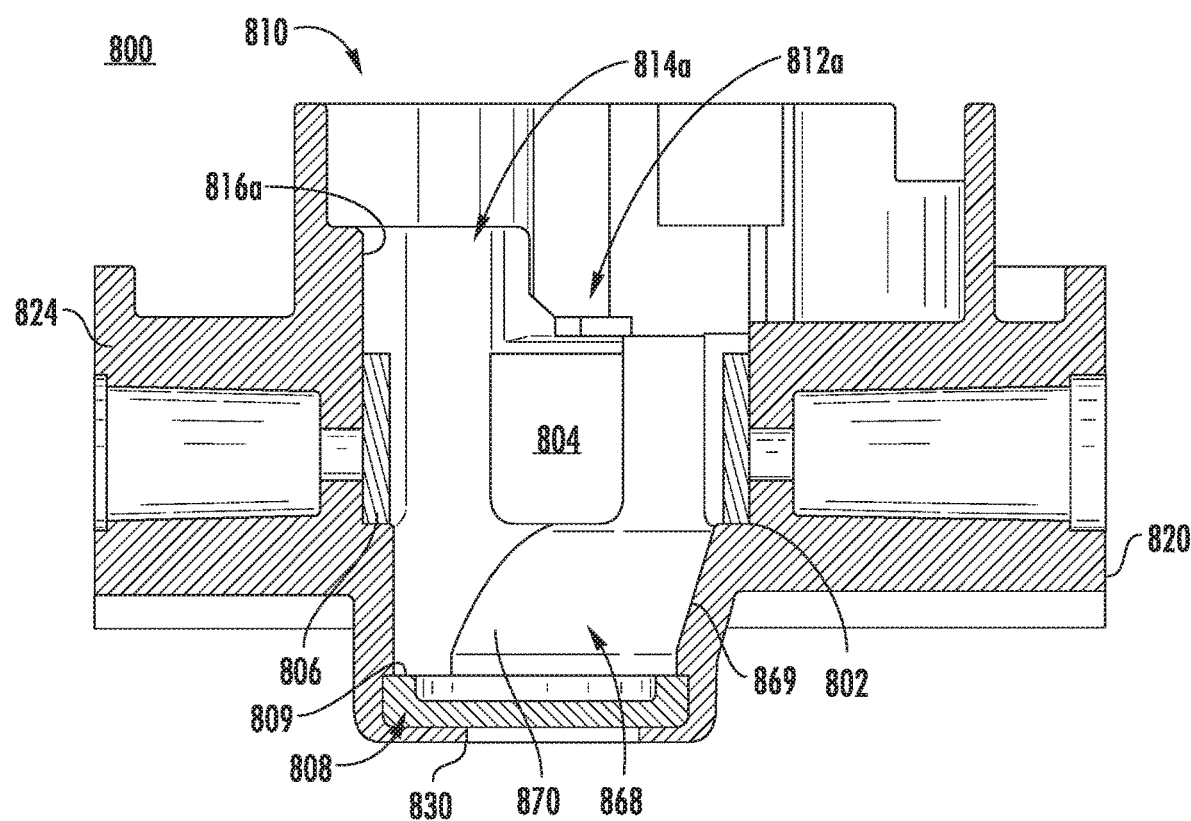
FIG. 40 is a cross section of the optical test platform of FIG. 37.

Turning to FIGS. 39 and 40, in some embodiments, the cavities 812a, 812b of the optical test platform 800 may be at least partially defined by a wall 816a, 816b of the shell 810. In some embodiments, a wall (e.g., wall 816a) may include one or more alignment ribs (e.g., alignment ribs 352, 353 shown in FIG. 35). With continued reference to FIGS. 39 and 40, in some embodiments, the wall 816a may be taller in certain positions than in others. For example, the wall 816a shown in FIGS. 39 and 40 is taller in an area adjacent to the third window 806 and third mount 824 than in an area adjacent to the first window 802 and first mount 820. With reference to FIG. 39, the wall 816a may define a first, taller height from the slot 880 (configured to receive a switch therein for detecting the sample tube, such as a mechanical switch) to second window 804, including the third window 806; and the wall 816a may define a second, shorter height from the second window 804 back around to the slot 880, including the first window 802.

In some embodiments, the portion of the wall 816a against which the sample tube (e.g., sample tube 342 shown in FIG. 35) is forced is taller than the portion of the wall adjacent the spring (e.g., spring 340 shown in FIG. 35 and/or spring 840 shown in FIG. 37).

The ribs (e.g., alignment ribs 352, 353 shown in FIG. 35) may be positioned on the first, taller portion of the wall and the spring 840 may be positioned above the second, shorter portion of the wall (e.g., as shown in FIG. 37). In such embodiments, the spring 840 may be positioned in line with the ribs on a generally horizontal plane relative to the optical test platform 800, such that the line of action of the spring is directed at the alignment ribs.

With reference to FIGS. 37 and 39-41, the shell 810 may include guide surfaces 868 having a curved portion 869 and straight portions 870 configured to align and hold the sample tubes (e.g., sample tube 342 shown in FIG. 34) within the cavities 812a, 812b. In the depicted embodiment, the guide surfaces 868 are positioned in both cavities 812a, 812b and are each shaped as U-channels. The depicted guide surface 868 in the cavity 812a with windows 802, 804, 806, 808 is oriented towards the third window 806 such that the guide surface 868 cooperates with the spring 840 and alignment ribs to hold the sample tube vertically in a repeatable, consistent position as described above. The guide surface 868 may taper downwardly and inwardly from a plane or axis on the wall 816a of the cavity 812a towards the window 808, such that the base of the sample tube is guided towards the repeatable, consistent predetermined position as it is inserted.

Figure 41:
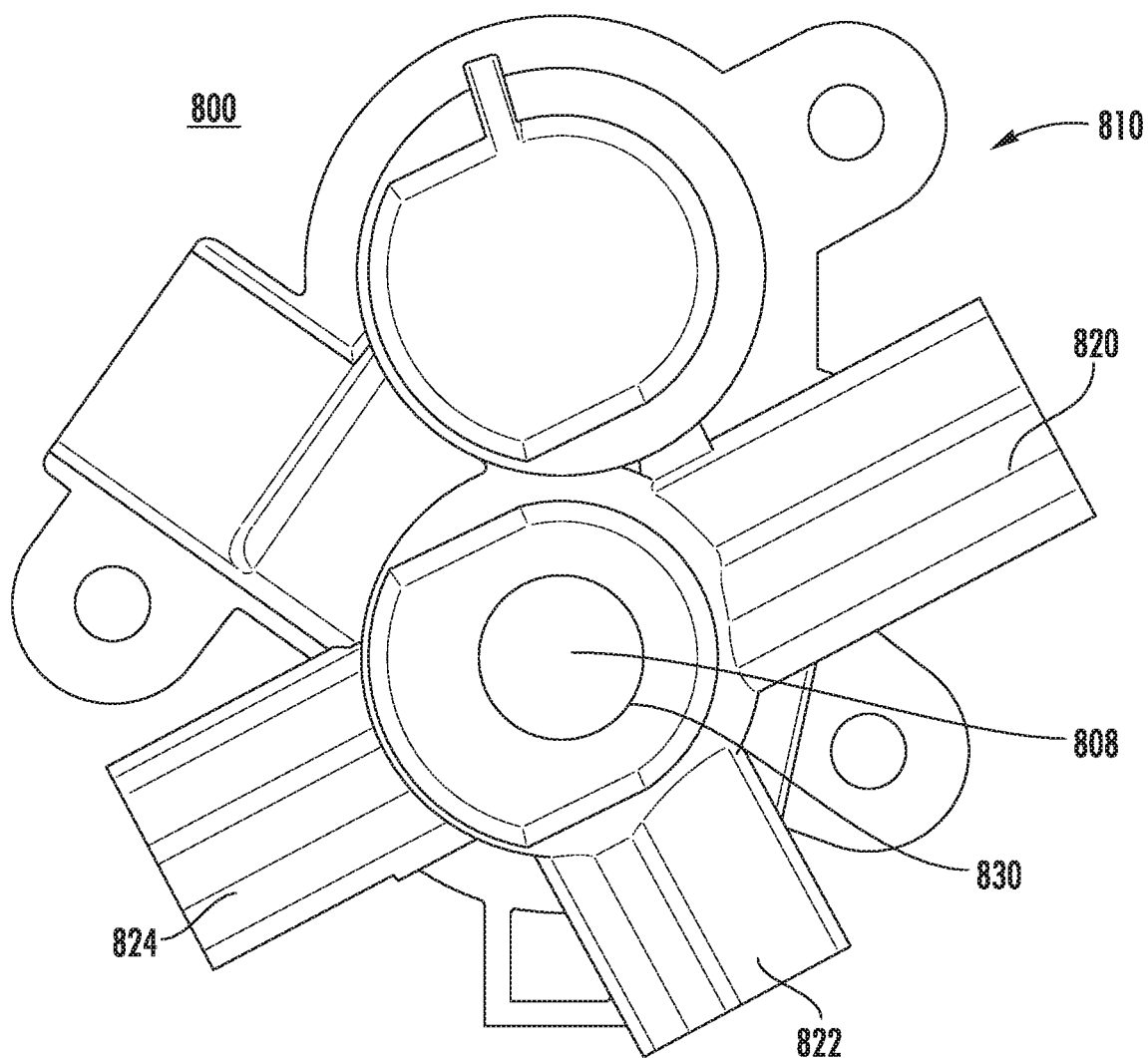
FIG. 41 is a bottom plan view of the optical test platform of FIG. 37.
Figure 42:
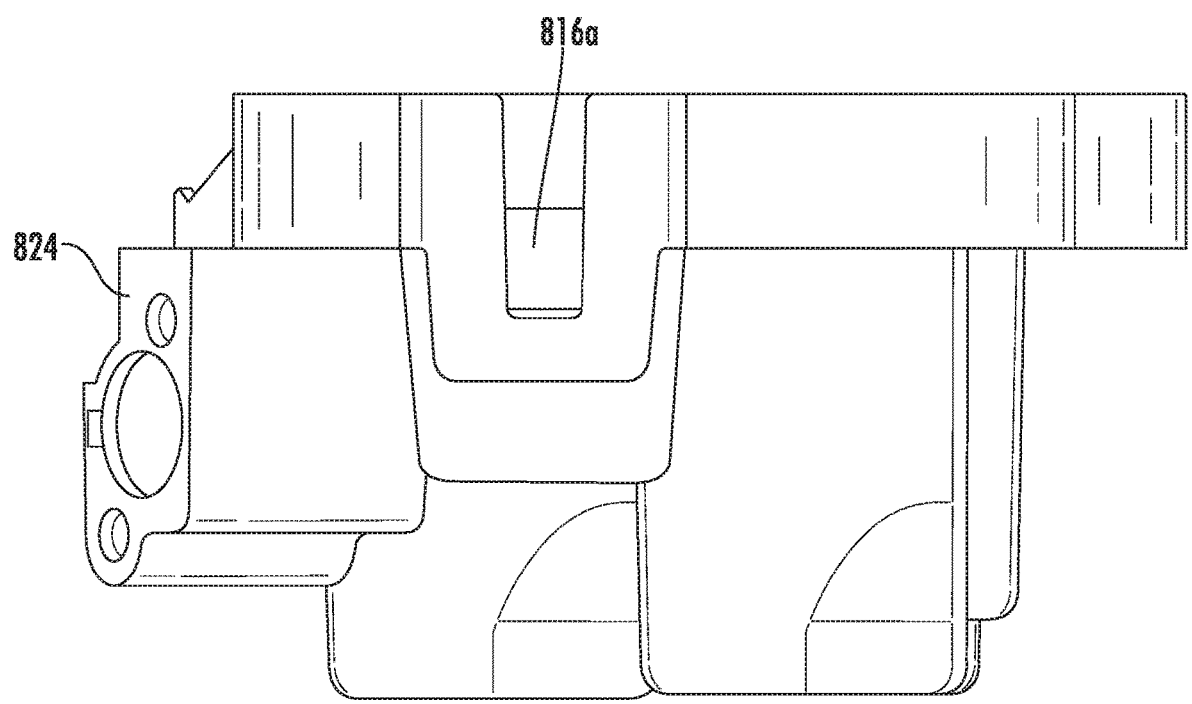
FIG. 42 is a side view of the optical test platform of FIG. 37.
Figure 43:
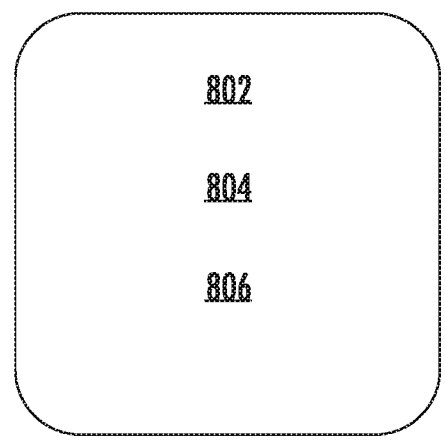
FIG. 43 is a window according to an example embodiment.
Figure 44:
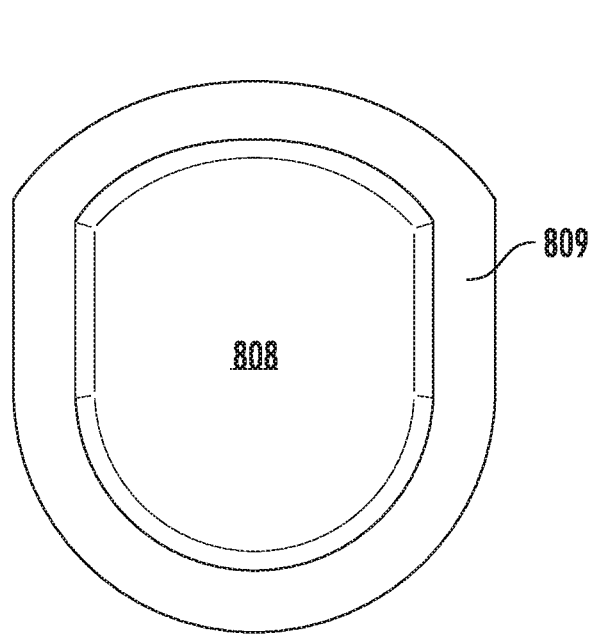
FIG. 44 is a top plan view of a lower window according to an example embodiment.
Figure 45:
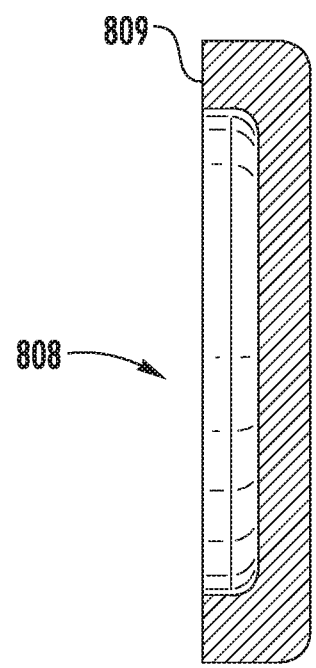
FIG. 45 is a cross section of the lower window of FIG. 44.

In some embodiments, the lower window 808 may define a complementary shape to the lower portion of the cavity 812a. With reference to FIGS. 39-41 and 44-45, the lower window 808 may be substantially "U" or "bell" shaped to match the shape of the wall 816a and guide surfaces 868 of the cavity 812a. The lower window 808 may include a raised edge 809 configured to engage the wall 816a. With reference to FIG. 40, the lower window 808 may be enclosed by and firmly fixed to the shell 810 (e.g., by overmolding) at the bottom of the cavity 812a. With reference to FIG. 41, in some embodiments, a lower aperture 830 through which the illumination light is transmitted may be substantially circular (e.g., similar to the aperture 330). The lower aperture 830 may define a radial center at substantially the horizontal center of the cavity 812a.

With reference to FIGS. 39-41 and 43, in some embodiments, the upper windows 802, 804, 806 may be substantially square and may not extend the full height of the cavity 812a or the channels in which they are seated. The windows 802, 804, 806 may be engaged with the shell 810 according to any of the embodiments disclosed herein. In some embodiments, at least a portion of the windows 802, 804, 806 may be shorter than the second, shorter height of the wall 816a discussed above, such that the spring 840 may operate over the windows. The upper windows 802, 804, 806 may be embedded in the shell 810 (e.g., via overmolding), slid into the shell (e.g., vertically downward into predefined channels), or attached via any other means.

Further details regarding the operation and layout of the optical test platform may be found in U.S. Provisional Application No. 62/487,807, entitled "Optical Test Platform," and filed Apr. 20, 2017, which application is incorporated by reference herein in its entirety.

Figure 18B:
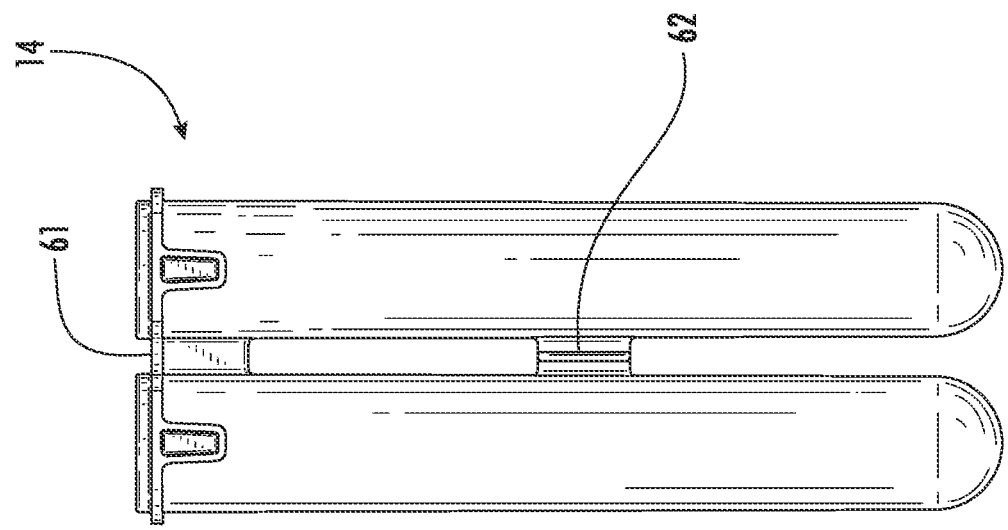
FIGS. 18A and 18B illustrate a dual sample tube structure in accordance with certain embodiments of the invention.
Figure 18A:
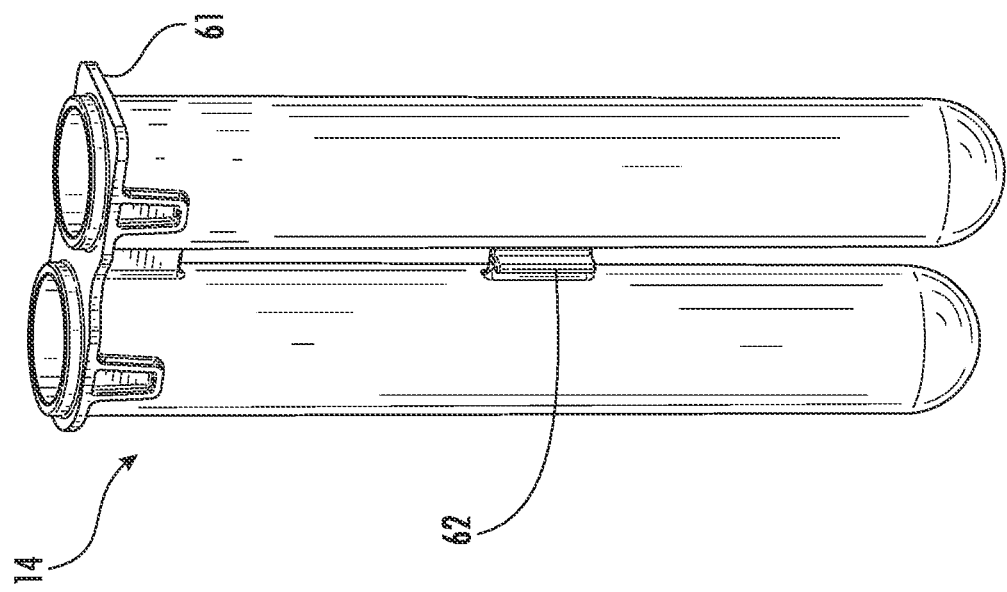

As previously discussed, a variety of sample tube configurations may be used in connection with the optical density instrument 1. For instance, the sample tubes may comprise at least one of glass, polycarbonate, polystyrene and/or the like. For example, sample tubes used for calibration reference may comprise polycarbonate, while disposable sample tubes may comprise polystyrene. Moreover, as mentioned, the sample tubes may include individual sample tubes or a dual sample tube structure. For example, FIGS. 18A and 18B illustrate a dual sample tube structure 14 in accordance with certain embodiments of the invention. As shown in FIG. 18, two sample tubes 14 are linked via a top connecting portion 61 at the tops of the sample tubes 14 and a bridge structure 62 between the sample tubes 14 at the middle of the sample tubes 14. The top connecting portion 61 and the bridge structure 62 may promote stability of the sample tubes 14 within the handheld unit 10 and the optical test platform 13 to prevent spills, leaks, and/or the like. Moreover, in some embodiments the dual sample tube structure 14 shown in FIGS. 18A and 18B may include a black and white scale (e.g., Wickham Scale) on the bridge structure 62 between the sample tubes 14 for better visualization of turbidity by a user. Referring back to FIG. 1, in some embodiments, a Wickham Scale may be disposed in a slot between the cavities that receive the sample tubes. In some embodiments, the bridge structure 62 may be keyed to a particular orientation of the sample tubes, such that they cannot be reversed accidentally. For example, the bridge structure 62 shown in FIG. 18A-18B may include a protrusion that inserts into a slot of the handheld unit 10 or into a slot on the Wickham Scale (e.g., as shown in FIG. 1).

Figure 19:
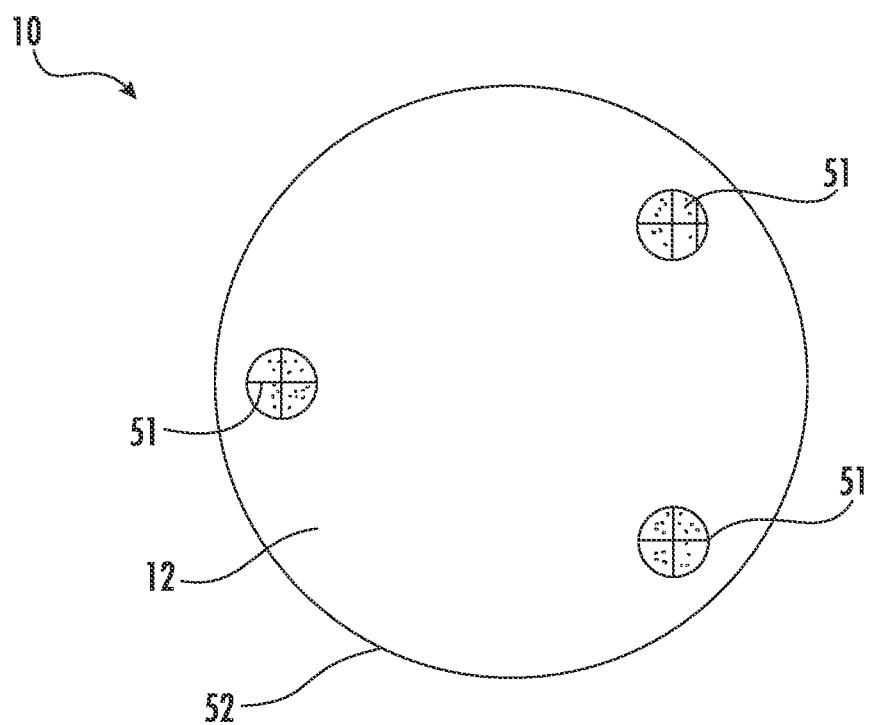
FIG. 19 is a bottom view of a handheld unit in accordance with certain embodiments of the invention.

According to certain embodiments, the bottom 12 of the handheld portion 10 may further comprise tip resistant features. For example, FIG. 19 is a bottom view of the handheld unit 10 in accordance with certain embodiments of the invention. As shown in FIG. 19, the bottom 12 of the handheld unit 10 comprises a plurality support elements 51 (e.g., non-skid feet). The plurality of support elements 51 may provide tip resistance to the handheld portion 10. If sufficient force is applied to the handheld unit 10 to cause the handheld unit 10 to raise off the support elements 51, then the handheld unit 10 will slide without tipping due to the translational surface 52 surrounding the support elements 51 on the bottom 12 of the handheld unit 10. In this regard, the handheld unit 10 may be tip resistant at any displacement angle.

In some embodiments, the support elements 51 may be positioned on the bottom shell surface 12 such that one of the support elements 51 is located along a diametric line of what may be a circular bottom shell surface 12, and a second and third support elements 51 are each located equidistance from the diametric line and the first support element. As shown in FIG. 19, this positioning of the support elements 51, along with recessing the support elements partly into the bottom shell surface 12 may be combined in an embodiment of the present disclosure. In some embodiments, the support elements may be circumferentially equidistant from each adjacent support element and each support element may be equidistant from a center of the bottom surface 12. Additionally, in some embodiments as shown in FIG. 19, the support elements 51 may be spaced a distance from the outer edge of the bottom shell surface 12. Particularly, the support elements 51 may be disposed on a concentric circle having a diameter that is less than the outer diameter of the bottom shell surface 12. As described below, in such an embodiment, the translational surface 52 may be positioned as an annular portion of the bottom shell surface extending radially outward from the support elements 51 to the outer edge of the bottom shell surface 12.

The translational surface 52 may be configured with a lower coefficient of friction to allow the optical testing instrument to slide when supported by the translational surface (e.g., when the optical testing instrument is tipped as described herein. As depicted in FIG. 19, the translational surface 52 of the bottom shell surface 12 may, in some embodiments, comprise a substantially flat surface. In an instance in which the handheld unit 10 is oriented in an operational testing position, flat on a table or other work surface, the translational surface 52 may be positioned substantially parallel to the support surface and may be held above the support surface by the support elements 51. In some embodiments, the translational surface 52 may be a section or portion of the bottom shell surface 12. In some embodiments, the translational surface 52 may be a contiguous section or portion of the bottom shell surface 12. In some embodiments, all of the bottom shell surface 12 may have the lower friction coefficient than the support elements 51, and the portion of the bottom shell surface 12 that contacts the support surface may be considered the translational surface. In some embodiments, the translational surface 52 may be defined as an annular portion of the bottom shell surface 12 extending circumferentially around an edge of the bottom shell surface 12. By a more particular example, the translational surface 52 may be defined by the bottom shell surface 12 as an annular portion of the bottom shell surface extending radially outward from the support elements 51 to an edge of the bottom shell surface 12.

Figure 46:
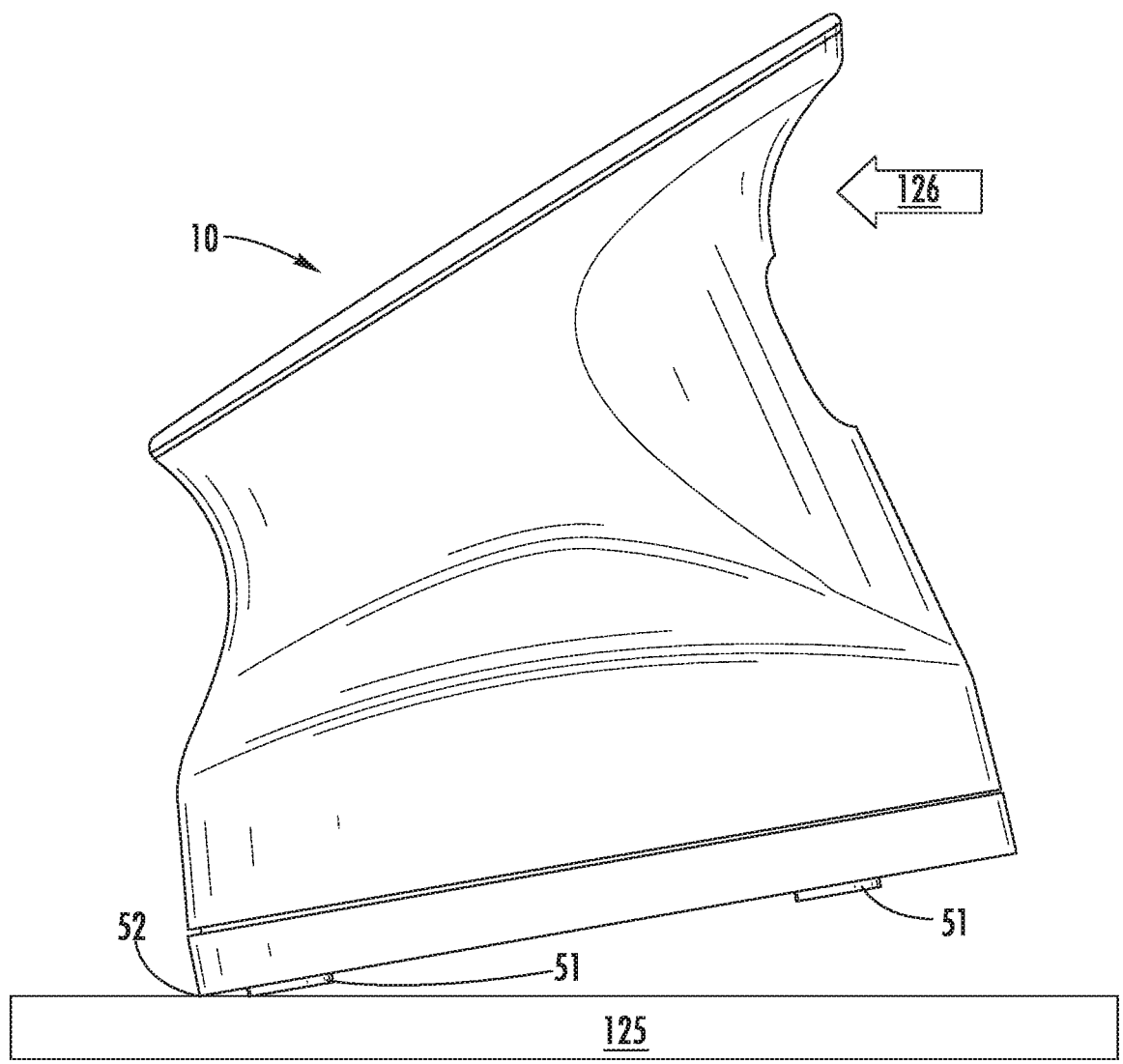
FIG. 46 is a side view of an optical testing instrument in a tipped or angled position according to an example embodiment.

One of ordinary skill in the art will appreciate, in light of this disclosure, that the support elements 51 and bottom shell surface 12 may take many shapes and forms so long as the handheld unit 10 is permitted to translate on the translational surface 52 when tipped, rather than tipping completely over. To facilitate the translation, a portion of the translational surface 52 need only be positioned opposite the direction of force from the support elements 51 that form the fulcrum of the instrument. Said differently, with reference to FIG. 46, when the handheld unit 10 is tipped about a pivot axis on one or more of the support elements 51, the translational support surface 52 is pivoted into contact with the support surface 125. In many instances, this means that portions of the translational surface 52 are positioned radially outward of the support elements 51. In some further embodiments, the translational support surface 52 engages the support surface 125 before the instrument can tip past the point that its center of gravity carries the instrument the rest of the way over.

In some embodiments, the translation of the handheld unit 10 may begin when the tipping force (e.g., force 126 shown in FIG. 46) or inertia of the instrument overcomes the static friction between the instrument (e.g., including the combination of translational surface 52 and support element 51 surfaces currently touching the support surface) and the support surface 125. For example, if the support elements 51 have a higher coefficient of friction than the translational surface 52, the greater the portion of the instrument's weight that is transferred to the translational surface 52, the more likely the instrument is to slide. In this manner, the handheld unit 10 may begin translating while both the translational surface 52 and one or more of the support elements 51 are in contact with the support surface 125. In such embodiments, as the handheld unit 10 tips, a greater and greater portion of the weight of the instrument is transferred to the translational surface 52, thus gradually lowering the frictional resistance between the instrument and the support surface 125. Once the lateral force between the handheld unit 10 and the support surface 125 overcomes the decreasing frictional resistance, the instrument begins to translate. The stability of the tool may depend upon the height of the support elements 51, the coefficients of friction of the support elements 51 and the translational element 52, the distance between the support elements 51 and the contact point of the translational element 52 (e.g., the point, proximate the edge of the bottom shell surface 12, at which the translational surface 52 contacts the support surface 125), the center of gravity of the handheld unit 10, the width of the handheld unit 10, the shape of the bottom shell surface 12, and the properties of the support surface 125.

In some embodiments, the handheld unit 10 may pivot about two or more support elements 51 about a common contact axis extending therebetween. In such embodiments, the handheld unit 10 may pivot about the two or more support elements 51 until the translational surface 52 contacts the support surface. Further details regarding the operation and layout of the tip resistant features may be found in U.S. Provisional Application No. 62/487,860, entitled "Tip Resistant Optical Testing Instrument," and filed Apr. 20, 2017, which application is incorporated by reference herein in its entirety.

In this regard, the optical density instrument provides additional convenience, comfort, and safety over existing density measurement devices.

II. System for Measuring Optical Density

Figure 20:
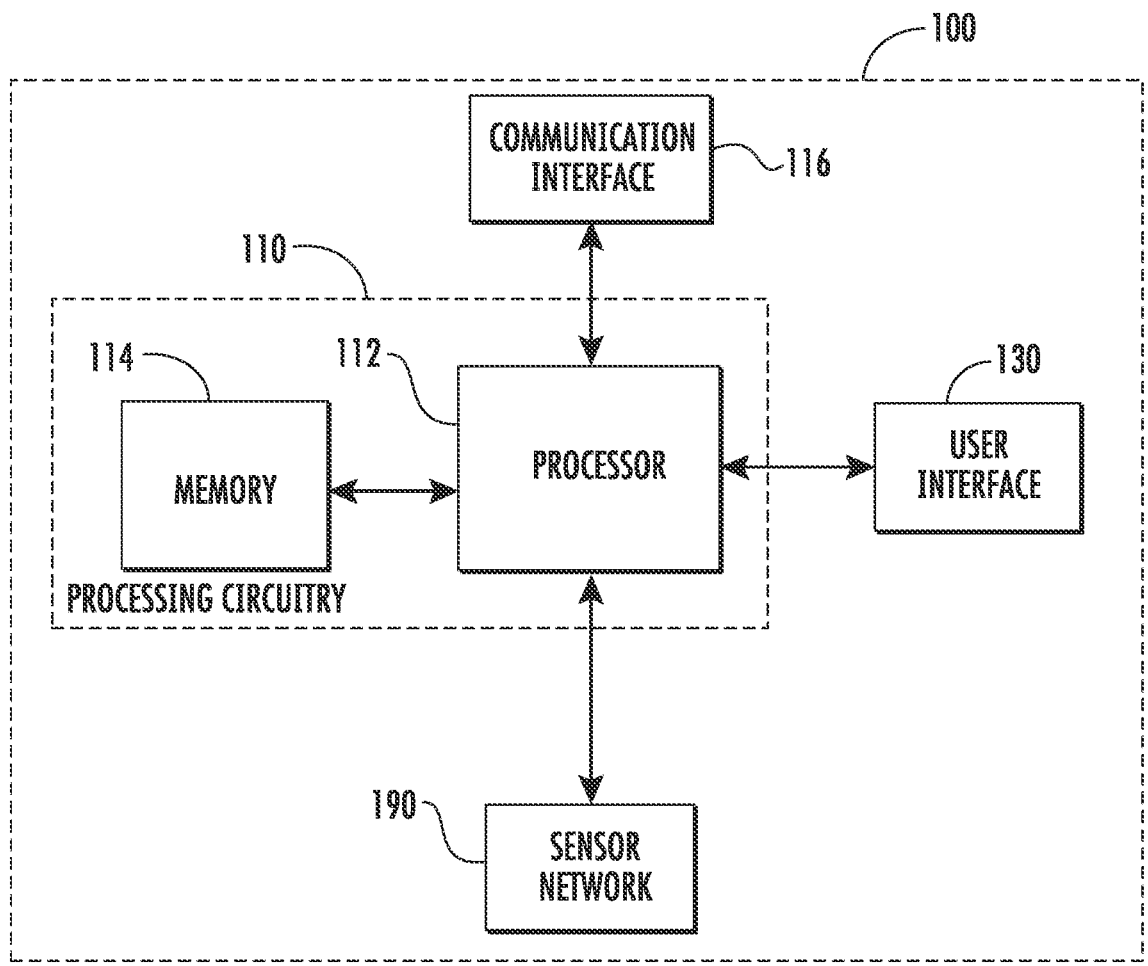
FIG. 20 is a block diagram of a system for measuring optical density of a sample in accordance with certain embodiments of the invention.

In another aspect, certain embodiments according to the invention provide systems for measuring optical density of a sample. The system includes the optical density instrument 1 discussed above and a user interface 130. For example, FIG. 20 is a block diagram of a system 100 for measuring optical density of a sample in accordance with certain embodiments of the invention. As shown in FIG. 20, the system 100 may include processing circuitry 110 that may be configured to interface with, control or otherwise coordinate the operations of various components or modules described herein in connection with measuring optical density as described herein. In some embodiments, the system 100 may further include a communication interface 116 for transmitting and receiving information from other sensors, computers, and input devices (e.g., locally or via a local or remote network).

In some embodiments, the processing circuitry 110 may be embodied as a chip or chip set. In other words, the processing circuitry 110 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The processing circuitry 110 may therefore, in some cases, be configured to implement an embodiment of the present invention on a single chip or as a single "system on a chip." As such, in some cases, a chip or chipset may constitute means for performing one or more operations for providing the functionalities described herein.

According to certain embodiments, the processing circuitry 110 may include one or more instances of a processor 112 and memory 114 that may be in communication with or otherwise control a user interface 130. As such, the processing circuitry 110 may be embodied as a circuit chip (e.g., an integrated circuit chip) configured (e.g., with hardware, software or a combination of hardware and software) to perform operations described herein.

The user interface 130 may include one or more interface mechanisms or devices for enabling communication with a user (e.g., a laptop computer). In some cases, the user interface 130 may be any means such as a device or circuitry embodied in either hardware, or a combination of hardware and software that is configured to receive and/or transmit data from/to devices or components in communication with the processing circuitry 110 via internal and/or external communication mechanisms. Accordingly, for example, the user interface 130 may further include wired and/or wireless communication equipment for at least communicating between a user and the optical density instrument 1, and/or other components or modules described herein. The user interface 130 may be in communication with the processing circuitry 110 to receive an indication of a user input at the user interface 130 and/or to provide an audible, visual, mechanical, or other output to the user. As such, the user interface 130 may include, for example, a keypad, display, a touch screen display (e.g., display 615 shown in FIG. 25) and/or other input/output mechanisms. As such, the user interface 130 may, in some example embodiments, provide means for user control of managing or processing data access operations and/or the like. In some example embodiments a user interface 130 may not be present in the detection device, but the user interface may be implemented on a remote device (e.g., smart phone, tablet, personal computer and/or the like) communicatively connected to the detection such as by Bluetooth™ communication or a local area network, for example.

The communication interface 116 may include one or more interface mechanisms for enabling communication with other devices and/or networks. In some cases, the communication interface 116 may be any means such as a device or circuitry embodied in either hardware, or a combination of hardware and software that is configured to receive and/or transmit data from/to a network and/or any other device or module in communication with the processing circuitry 110. By way of example, the communication interface 116 may be configured to enable communication amongst components of the system 100, the detection device, and/or remote computing devices. In some examples, the communication interface 116 may include a network configured to transmit information amongst various devices. Accordingly, the communication interface 116 may, for example, include supporting hardware and/or software for enabling wireless and/or wireline communications via cable, digital subscriber line (DSL), universal serial bus (USB), Ethernet, or other methods.

The network in which system 100, the detection device, and/or any of the components thereof may operate may include a local area network, the Internet, any other form of a network, or in any combination thereof, including proprietary private and semi-private networks and public networks. The network may comprise a wired network and/or a wireless network (e.g., a cellular network, wireless local area network, wireless wide area network, some combination thereof, and/or the like).

The processor 112 may be embodied in a number of different ways. For example, the processor 112 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor 112 may comprise a plurality of processors. The plurality of processors may be in operative communication with each other and may be collectively configured to perform one or more functionalities of the system 100 and/or detection device as described herein. The plurality of processors may be embodied on a single computing device or distributed across a plurality of computing devices collectively configured to function as apparatus 100. For example, some operations performed herein may be performed by components of the detection device while some operations may be performed on a remote device communicatively connected to the detection device. For example, a user device such as a smart phone, tablet, personal computer and/or the like may be configured to communicate with the detection device such as by Bluetooth™ communication or over a local area network. Additionally or alternatively, a remote server device may perform some of the operations described herein, such as processing data collected by any of the sensors, and providing or communicating resultant data to other devices accordingly.

In an example embodiment, the processor 112 may be configured to execute instructions stored in the memory 114 or otherwise accessible to the processor 112. As such, whether configured by hardware or by a combination of hardware and software, the processor 112 may represent an entity (e.g., physically embodied in circuitry—in the form of processing circuitry 110) capable of performing operations according to embodiments of the present invention while configured accordingly. Thus, for example, when the processor 112 is embodied as an ASIC, FPGA or the like, the processor 112 may be specifically configured hardware for conducting the operations described herein. Alternatively, as another example, when the processor 112 is embodied as an executor of software instructions, the instructions may specifically configure the processor 112 to perform the operations described herein in reference to execution of an example embodiment.

In some embodiments, the memory 114 may include one or more non-transitory memory devices such as, for example, volatile and/or non-volatile memory that may be either fixed or removable. The memory 114 may comprise a non-transitory computer-readable storage medium. It will be appreciated that while the memory 114 is illustrated as a single memory, the memory 114 may comprise a plurality of memories. The plurality of memories may be embodied on a single computing device or may be distributed across a plurality of computing devices. The memory 114 may be configured to store information, data, applications, instructions or the like for enabling the processing circuitry 110 to carry out various functions in accordance with exemplary embodiments of the present invention. For example, the memory 114 may be configured to buffer input data for processing by the processor 112. Additionally or alternatively, the memory 114 may be configured to store instructions for execution by the processor 112. As yet another alternative or additional capability, the memory 114 may include one or more databases that may store or buffer a variety of data sets or tables useful for operation of the modules described below and/or the processing circuitry 110. Among the contents of the memory 114, applications or instruction sets may be stored for execution by the processor 112 in order to carry out the functionality associated with each respective application or instruction set. In particular, the memory 114 may store executable instructions that enable the computational power of the processing circuitry 110 to be employed to improve the functioning of the optical density instrument 1 as described herein. For example, memory 114 may store data detected by a sensor(s) of the detection device, and/or application code for processing such data according to example embodiments. In some cases, the memory 114 may be in communication with one or more of the processor 112, communication interface 116, user interface 130, illumination light 33, density sensor 31, nephelometric sensor 32, emitter 30, and/or other components of the system 100. As such, the improved operation of the computational components of the optical density instrument 1 transforms the optical density instrument 1 into a more capable tool for measuring optical density of a sample as described herein.

Figure 21:
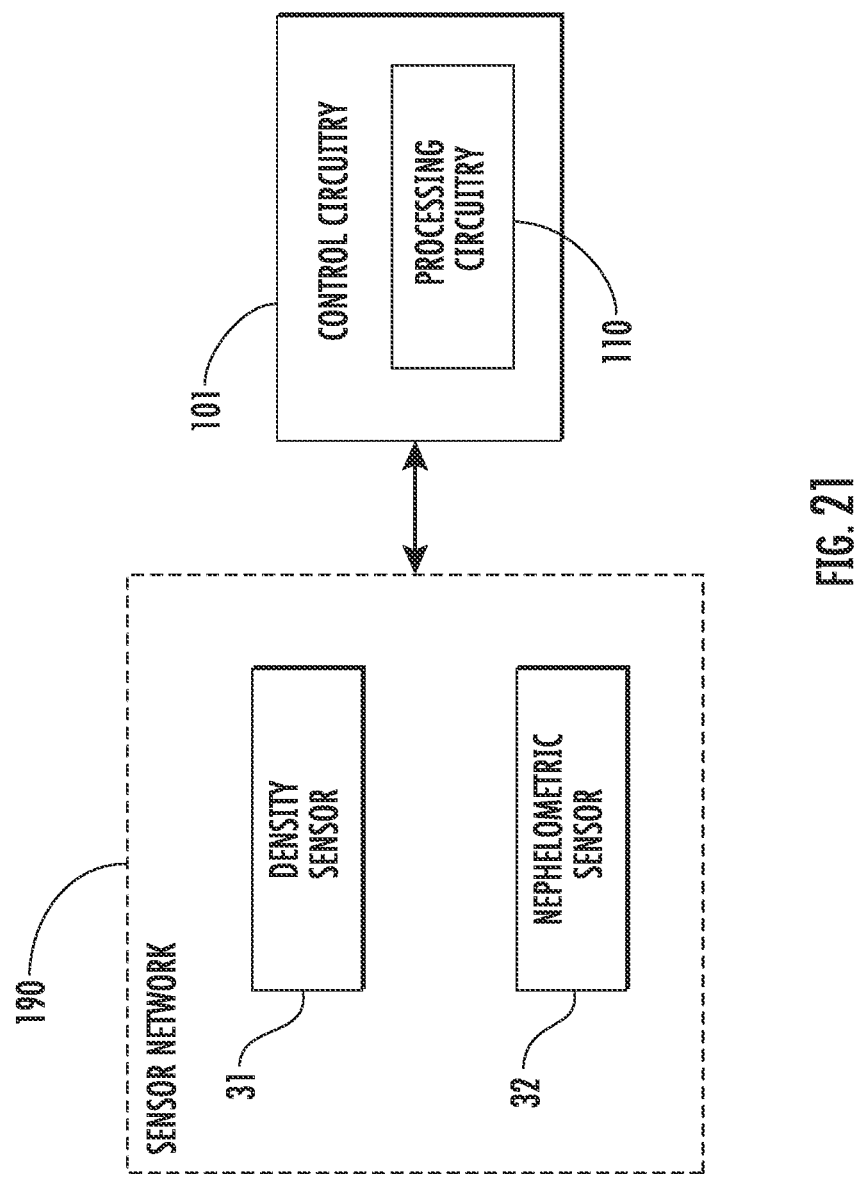
FIG. 21 is a block diagram of a sensor network in a system for measuring optical density of a sample in accordance with certain embodiments of the invention.

FIG. 21 is a block diagram of the sensor network 190 in the system 100 for measuring optical density of a sample in accordance with certain embodiments of the invention. In some embodiments, the sensor network 190 may provide data to the components described above to facilitate execution of the functions described above, and/or any other functions that the components may be configurable to perform. In some cases, the sensor network 190 may include (perhaps among other things) any or all of a density sensor 31 or a nephelometric sensor 32, as shown in FIG. 21. In this regard, FIG. 21 illustrates a block diagram of some components that may be employed as part of the sensor network 190 in accordance with an example embodiment.

In some embodiments, the system 100, which may be embodied as a single apparatus or system of components, may be implemented as or at least partially as a distributed system or cloud based system and may therefore include any number of remote user devices and/or server devices. Accordingly, example embodiments may not necessarily be limited to use in a laboratory settings, but may be implemented, for example in a manufacturing setting or other environment such that remote processing and/or monitoring of data collected by the detection device may be performed on servers and/or other like computing devices. Regardless of implementation, system 100 may be configured to perform and/or control performance of the various components and functionalities of the detection device as described herein.

In this regard, the system provides the additional convenience, comfort, and safety of the optical density instrument 1 over existing density measurement devices while also being continuously connected to a user interface.

III. Methods for Measuring Optical Density

Figure 22:
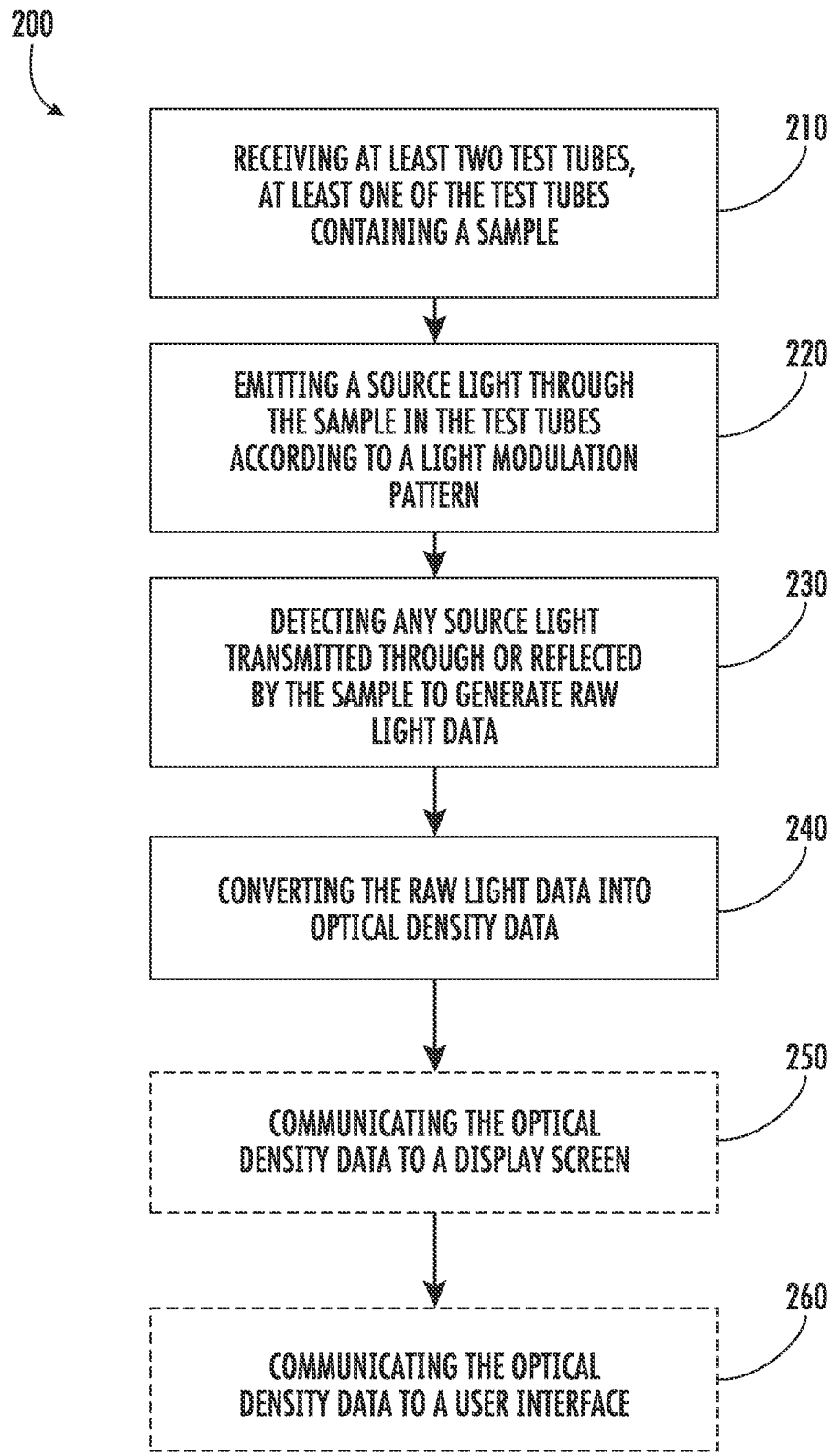
FIG. 22 is a block diagram of a method for measuring optical density of a sample in accordance with certain embodiments of the invention.

In yet another aspect, certain embodiments according to the invention provide methods for measuring optical density of a sample. FIG. 22 is a block diagram of a method 200 for measuring optical density of a sample in accordance with certain embodiments of the invention. As shown in FIG. 22, the method 200 may include receiving at least two sample tubes, at least one of the sample tubes containing a sample at operation 210, emitting a source light through the sample in the sample tubes according to a light modulation pattern at operation 220, detecting any source light transmitted through or reflected by the sample to generate raw light data at operation 230, and converting the raw light data into optical density data at operation 240, and the optional steps of communicating the optical density data to a display screen at operation 250, and communicating the optical density data to a user interface of a separate computing device at operation 260. In some embodiments, illuminating the sample occurs concurrently with at least emitting the source light or detecting the source light. In further embodiments, communicating the optical density data to a user interface of a separate computing device occurs continuously.

In some embodiments, the light from the illumination light 33 may cause interference with detection of a signal by a sensor of the optical density instrument. If the ambient light or supplemental light is too bright, the light may "flood out" or interfere with sensor readings. However, as previously discussed, the illumination light may be needed to enable a user to see the sample tube and sample tube contents. For example, the density sensor 31 configured to detect source light through the sample tube 14 and/or the nephelometric sensor 32 configured to detect reflected or scattered source light from particles in the sample tube may be impacted by the illumination light such that the readings become inaccurate. Example embodiments may therefore modulate the illumination light such that sensor readings may be performed when the illumination light is off.

Figure 47:
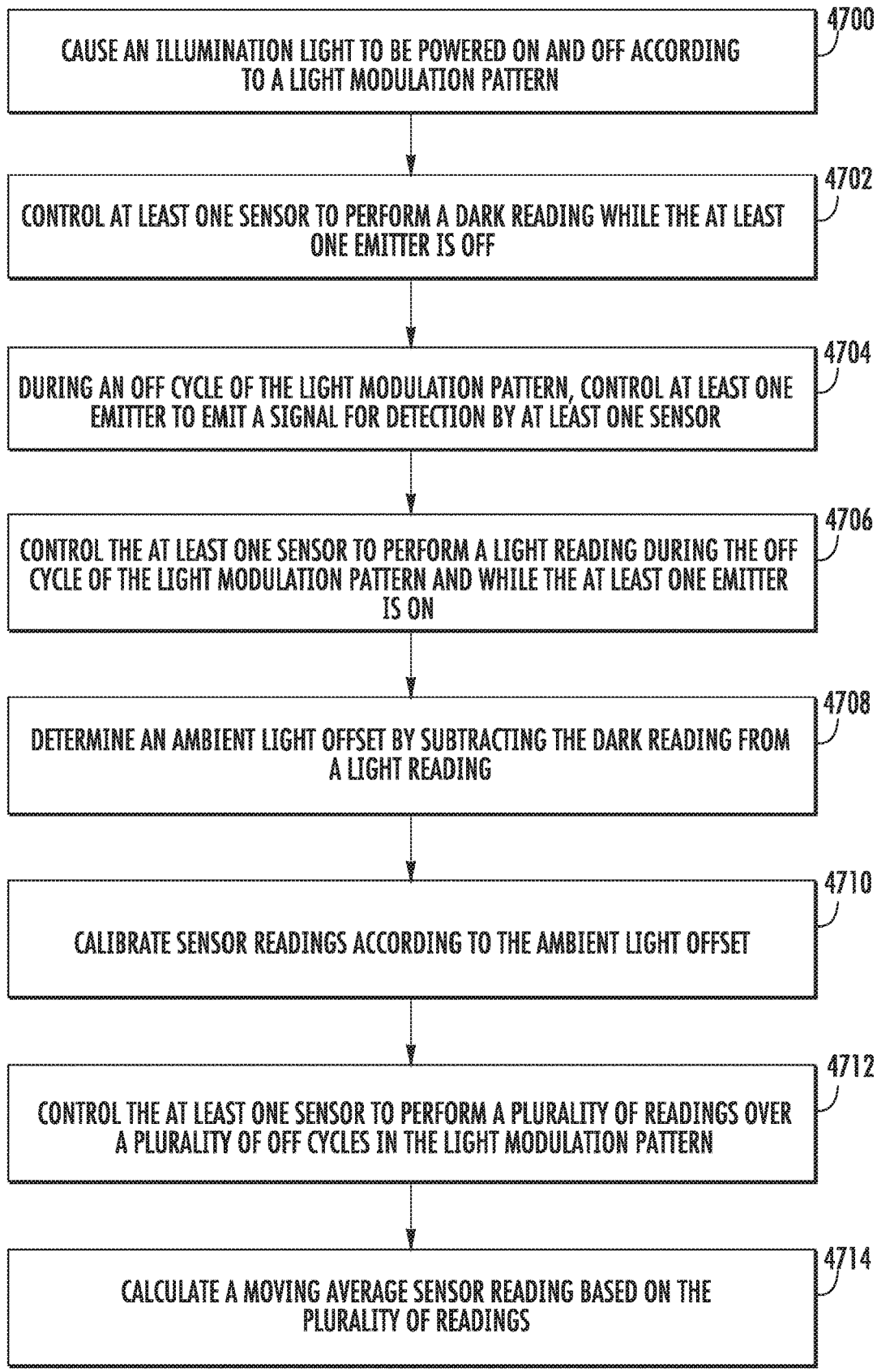
FIG. 47 is a flowchart illustrating operations according to an example embodiment.

FIG. 47 is a flowchart illustrating example operations of system 100 according to some example embodiments. As shown by operation 4700 of FIG. 47, system may include means, such as processing circuitry 110, processor 112, memory 114, communication interface 116, illumination light 33 (shown in FIG. 15), and/or the like, for causing an illumination light (e.g., illumination light 33) to be powered on and off according to a light modulation pattern having on cycles and off cycles for the illumination light.

Figure 23:
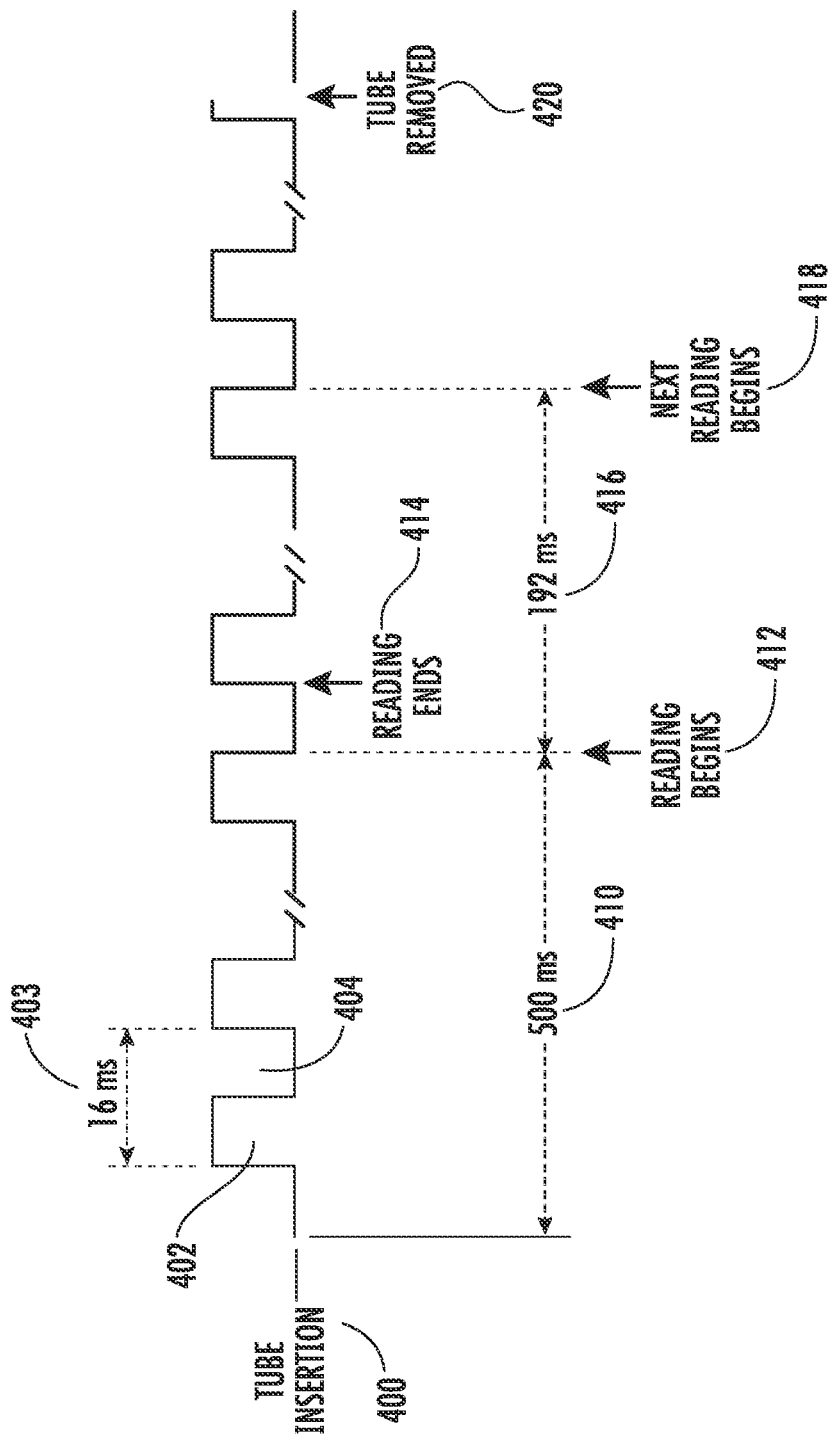
FIGS. 23 and 24 are example timing diagrams in accordance with certain embodiments of the invention.
Figure 24:
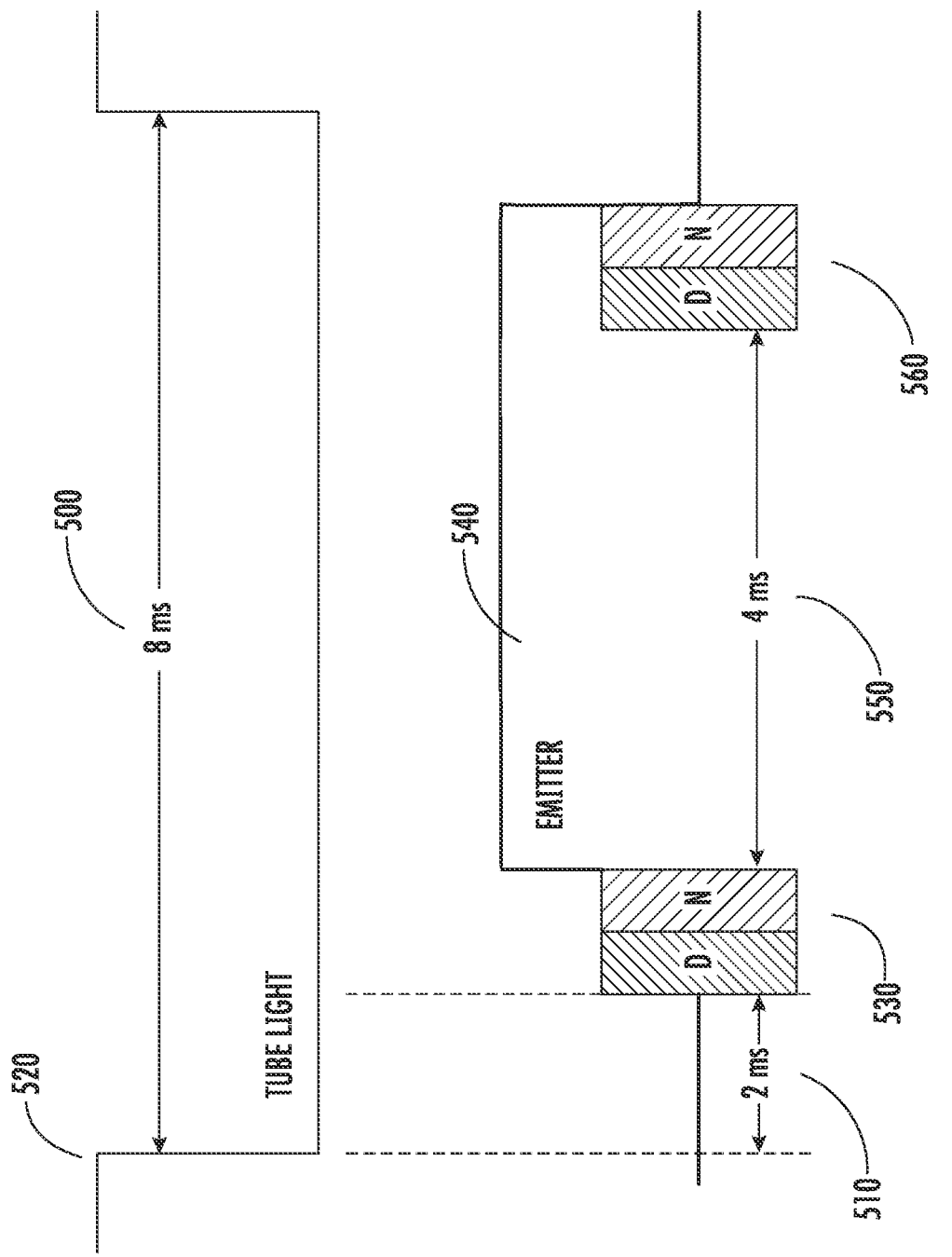

For example, FIGS. 23 and 24 are example timing diagrams in accordance with certain embodiments of the invention. As shown in FIG. 23, after sample tube insertion (400), the illumination light may be powered on (402) and off (404) for a predetermined interval of time. In some embodiments, the light modulation pattern may be configured to begin in response to an indication of a sample tube insertion. The indication may be provided in response to triggering of a physical switch in the detection device and/or user input to user interface 130, for example. The time intervals of the on and off cycles may be any predetermined or dynamically determined period of time. The time interval of an on cycle may be the same or different as that of an off cycle, and in some example, the intervals may change or vary. The example light modulation pattern of FIG. 23 indicates an 8 millisecond (ms) on cycle followed by an 8 ms off cycle, repeated. In this regard, the illumination light is modulated with a 16 ms period and 50% duty cycle (403).

The light modulation pattern may be determined such that the illumination light is powered on for durations adequate for enabling supplemental light to be provided for the practitioner or user to view the suspension in the sample tube, but powered off for durations such that the supplemental illumination appears constant to the user. In this regard, no flickering or an insignificant amount of flickering may be apparent to the user such that the illumination light appears constant. The time intervals of the on and/or off cycle may therefore be determined based on a variety of factors including but not limited to the type, size, and/or luminosity of illumination light. Other timing intervals than those illustrated may therefore be used. For example, in some embodiments, the illumination light may cycle on and off for intervals of 10 ms. In some embodiments, the light modulation pattern may comprise time-division multiplexing the illumination light and the emitter.

In some embodiments, the longest off cycle may be defined by the period a human can tolerate the illumination light being off. For example, in some embodiments, the off cycle may be 16.66 ms or less (e.g., 30 Hz cycle or greater). In some embodiments, the shortest off cycle may be defined by the time required to process a sensor reading. For example, in some embodiments and for some sensors, a sensor may require 6 ms to process a reading. In such embodiments, the off cycle may be 6 ms or greater (e.g., 84 Hz cycle or less). In some embodiments and for some sensors, a sensor may require 8 ms to process a reading. In such embodiments, the off cycle may be 8 ms or greater (e.g., 65 Hz cycle or less).

Thus, in some embodiments, the off cycle of the light modulation pattern may be from 6 ms to 16.66 ms. In some embodiments, the off cycle of the light modulation pattern may be from 5 ms to 16.66 ms. In some embodiments, the off cycle of the light modulation pattern may be from 4 ms to 16.66 ms. In some embodiments, the off cycle of the light modulation pattern may be from 3 ms to 16.66 ms. In some embodiments, the off cycle of the light modulation pattern may be from 2 ms to 16.66 ms. In some embodiments, the off cycle of the light modulation pattern may be from 6 ms to 16 ms. In some embodiments, the off cycle of the light modulation pattern may be from 5 ms to 16 ms. In some embodiments, the off cycle of the light modulation pattern may be from 4 ms to 16 ms. In some embodiments, the off cycle of the light modulation pattern may be from 3 ms to 16 ms. In some embodiments, the off cycle of the light modulation pattern may be from 2 ms to 16 ms. In some embodiments, the off cycle of the light modulation pattern may be from 6 ms to 17 ms. In some embodiments, the off cycle of the light modulation pattern may be from 5 ms to 17 ms. In some embodiments, the off cycle of the light modulation pattern may be from 4 ms to 17 ms. In some embodiments, the off cycle of the light modulation pattern may be from 3 ms to 17 ms. In some embodiments, the off cycle of the light modulation pattern may be from 2 ms to 17 ms. In some embodiments, the off cycle of the light modulation pattern may be from 2 ms to 20 ms. In some embodiments, the off cycle of the light modulation pattern may be from 2 ms to 19 ms. In some embodiments, the off cycle of the light modulation pattern may be from 2 ms to 18 ms. In some embodiments, the off cycle of the light modulation pattern may be from 2 ms to 15 ms. In some embodiments, the off cycle of the light modulation pattern may be from 2 ms to 14 ms. In some embodiments, the off cycle of the light modulation pattern may be from 2 ms to 13 ms. In some embodiments, the off cycle of the light modulation pattern may be from 2 ms to 12 ms. In some embodiments, the off cycle of the light modulation pattern may be from 2 ms to 11 ms. In some embodiments, the off cycle of the light modulation pattern may be from 2 ms to 10 ms. In some embodiments, the off cycle of the light modulation pattern may be from 2 ms to 9 ms. In some embodiments, the off cycle of the light modulation pattern may be from 2 ms to 8 ms. In some embodiments, the off cycle of the light modulation pattern may be from 2 ms to 7 ms. In some embodiments, the off cycle of the light modulation pattern may be from 2 ms to 6 ms. In some embodiments, the off cycle of the light modulation pattern may be from 2 ms to 5 ms. In some embodiments, the off cycle of the light modulation pattern may be from 2 ms to 4 ms. In some embodiments, the off cycle of the light modulation pattern may be from 2 ms to 3 ms. In some embodiments, the off cycle of the light modulation pattern may be from 3 ms to 20 ms. In some embodiments, the off cycle of the light modulation pattern may be from 4 ms to 20 ms. In some embodiments, the off cycle of the light modulation pattern may be from 5 ms to 20 ms. In some embodiments, the off cycle of the light modulation pattern may be from 6 ms to 20 ms. In some embodiments, the off cycle of the light modulation pattern may be from 7 ms to 20 ms. In some embodiments, the off cycle of the light modulation pattern may be from 8 ms to 20 ms. In some embodiments, the off cycle of the light modulation pattern may be from 9 ms to 20 ms. In some embodiments, the off cycle of the light modulation pattern may be from 10 ms to 20 ms. In some embodiments, the off cycle of the light modulation pattern may be from 11 ms to 20 ms. In some embodiments, the off cycle of the light modulation pattern may be from 12 ms to 20 ms. In some embodiments, the off cycle of the light modulation pattern may be from 13 ms to 20 ms. In some embodiments, the off cycle of the light modulation pattern may be from 14 ms to 20 ms. In some embodiments, the off cycle of the light modulation pattern may be from 15 ms to 20 ms. In some embodiments, the off cycle of the light modulation pattern may be from 16 ms to 20 ms. In some embodiments, the off cycle of the light modulation pattern may be from 17 ms to 20 ms. In some embodiments, the off cycle of the light modulation pattern may be from 18 ms to 20 ms. In some embodiments, the off cycle of the light modulation pattern may be from 19 ms to 20 ms.

Thus, in some embodiments, the on cycle of the light modulation pattern may be from 6 ms to 16.66 ms. In some embodiments, the on cycle of the light modulation pattern may be from 5 ms to 16.66 ms. In some embodiments, the on cycle of the light modulation pattern may be from 4 ms to 16.66 ms. In some embodiments, the on cycle of the light modulation pattern may be from 3 ms to 16.66 ms. In some embodiments, the on cycle of the light modulation pattern may be from 2 ms to 16.66 ms. In some embodiments, the on cycle of the light modulation pattern may be from 6 ms to 16 ms. In some embodiments, the on cycle of the light modulation pattern may be from 5 ms to 16 ms. In some embodiments, the on cycle of the light modulation pattern may be from 4 ms to 16 ms. In some embodiments, the on cycle of the light modulation pattern may be from 3 ms to 16 ms. In some embodiments, the on cycle of the light modulation pattern may be from 2 ms to 16 ms. In some embodiments, the on cycle of the light modulation pattern may be from 6 ms to 17 ms. In some embodiments, the on cycle of the light modulation pattern may be from 5 ms to 17 ms. In some embodiments, the on cycle of the light modulation pattern may be from 4 ms to 17 ms. In some embodiments, the on cycle of the light modulation pattern may be from 3 ms to 17 ms. In some embodiments, the on cycle of the light modulation pattern may be from 2 ms to 17 ms. In some embodiments, the on cycle of the light modulation pattern may be from 2 ms to 20 ms. In some embodiments, the on cycle of the light modulation pattern may be from 2 ms to 19 ms. In some embodiments, the on cycle of the light modulation pattern may be from 2 ms to 18 ms. In some embodiments, the on cycle of the light modulation pattern may be from 2 ms to 15 ms. In some embodiments, the on cycle of the light modulation pattern may be from 2 ms to 14 ms. In some embodiments, the on cycle of the light modulation pattern may be from 2 ms to 13 ms. In some embodiments, the on cycle of the light modulation pattern may be from 2 ms to 12 ms. In some embodiments, the on cycle of the light modulation pattern may be from 2 ms to 11 ms. In some embodiments, the on cycle of the light modulation pattern may be from 2 ms to 10 ms. In some embodiments, the on cycle of the light modulation pattern may be from 2 ms to 9 ms. In some embodiments, the on cycle of the light modulation pattern may be from 2 ms to 8 ms. In some embodiments, the on cycle of the light modulation pattern may be from 2 ms to 7 ms. In some embodiments, the on cycle of the light modulation pattern may be from 2 ms to 6 ms. In some embodiments, the on cycle of the light modulation pattern may be from 2 ms to 5 ms. In some embodiments, the on cycle of the light modulation pattern may be from 2 ms to 4 ms. In some embodiments, the on cycle of the light modulation pattern may be from 2 ms to 3 ms. In some embodiments, the on cycle of the light modulation pattern may be from 3 ms to 20 ms. In some embodiments, the on cycle of the light modulation pattern may be from 4 ms to 20 ms. In some embodiments, the on cycle of the light modulation pattern may be from 5 ms to 20 ms. In some embodiments, the on cycle of the light modulation pattern may be from 6 ms to 20 ms. In some embodiments, the on cycle of the light modulation pattern may be from 7 ms to 20 ms. In some embodiments, the on cycle of the light modulation pattern may be from 8 ms to 20 ms. In some embodiments, the on cycle of the light modulation pattern may be from 9 ms to 20 ms. In some embodiments, the on cycle of the light modulation pattern may be from 10 ms to 20 ms. In some embodiments, the on cycle of the light modulation pattern may be from 11 ms to 20 ms. In some embodiments, the on cycle of the light modulation pattern may be from 12 ms to 20 ms. In some embodiments, the on cycle of the light modulation pattern may be from 13 ms to 20 ms. In some embodiments, the on cycle of the light modulation pattern may be from 14 ms to 20 ms. In some embodiments, the on cycle of the light modulation pattern may be from 15 ms to 20 ms. In some embodiments, the on cycle of the light modulation pattern may be from 16 ms to 20 ms. In some embodiments, the on cycle of the light modulation pattern may be from 17 ms to 20 ms. In some embodiments, the on cycle of the light modulation pattern may be from 18 ms to 20 ms. In some embodiments, the on cycle of the light modulation pattern may be from 19 ms to 20 ms.

In some embodiments, the off cycle of the light modulation pattern may be less than 21 ms. In some embodiments, the off cycle of the light modulation pattern may be less than 20 ms. In some embodiments, the off cycle of the light modulation pattern may be less than 19 ms. In some embodiments, the off cycle of the light modulation pattern may be less than 18 ms. In some embodiments, the off cycle of the light modulation pattern may be less than 17 ms. In some embodiments, the off cycle of the light modulation pattern may be less than 16 ms. In some embodiments, the off cycle of the light modulation pattern may be less than 15 ms. In some embodiments, the off cycle of the light modulation pattern may be less than 14 ms. In some embodiments, the off cycle of the light modulation pattern may be less than 13 ms. In some embodiments, the off cycle of the light modulation pattern may be less than 12 ms. In some embodiments, the off cycle of the light modulation pattern may be less than 11 ms. In some embodiments, the off cycle of the light modulation pattern may be less than 10 ms. In some embodiments, the off cycle of the light modulation pattern may be less than 9 ms. In some embodiments, the off cycle of the light modulation pattern may be less than 8 ms. In some embodiments, the off cycle of the light modulation pattern may be less than 7 ms. In some embodiments, the off cycle of the light modulation pattern may be less than 6 ms. In some embodiments, the off cycle of the light modulation pattern may be less than 5 ms. In some embodiments, the off cycle of the light modulation pattern may be less than 4 ms. In some embodiments, the off cycle of the light modulation pattern may be less than 3 ms. In some embodiments, the off cycle of the light modulation pattern may be less than 2 ms.

In some embodiments, the on cycle of the light modulation pattern may be less than 21 ms. In some embodiments, the on cycle of the light modulation pattern may be less than 20 ms. In some embodiments, the on cycle of the light modulation pattern may be less than 19 ms. In some embodiments, the on cycle of the light modulation pattern may be less than 18 ms. In some embodiments, the on cycle of the light modulation pattern may be less than 17 ms. In some embodiments, the on cycle of the light modulation pattern may be less than 16 ms. In some embodiments, the on cycle of the light modulation pattern may be less than 15 ms. In some embodiments, the on cycle of the light modulation pattern may be less than 14 ms. In some embodiments, the on cycle of the light modulation pattern may be less than 13 ms. In some embodiments, the on cycle of the light modulation pattern may be less than 12 ms. In some embodiments, the on cycle of the light modulation pattern may be less than 11 ms. In some embodiments, the on cycle of the light modulation pattern may be less than 10 ms. In some embodiments, the on cycle of the light modulation pattern may be less than 9 ms. In some embodiments, the on cycle of the light modulation pattern may be less than 8 ms. In some embodiments, the on cycle of the light modulation pattern may be less than 7 ms. In some embodiments, the on cycle of the light modulation pattern may be less than 6 ms. In some embodiments, the on cycle of the light modulation pattern may be less than 5 ms. In some embodiments, the on cycle of the light modulation pattern may be less than 4 ms. In some embodiments, the on cycle of the light modulation pattern may be less than 3 ms. In some embodiments, the on cycle of the light modulation pattern may be less than 2 ms.

In some embodiments, as described herein, the on cycle and off cycle of the light modulation pattern may have the same duration, which may include any pair of ranges or durations noted herein (e.g., 2 ms on, 2 ms off; 3 ms on, 3 ms off; 4 ms on, 4 ms off; 5 ms on, 5 ms off; Ems on, Ems off; 7 ms on, 7 ms off; 8 ms on, 8 ms off; 9 ms on, 9 ms off; 10 ms on, 10 ms off; 11 ms on, 11 ms off; 12 ms on, 12 ms off; 13 ms on, 13 ms off; 14 ms on, 14 ms off; 15 ms on, 15 ms off; 16 ms on, 16 ms off; 17 ms on, 17 ms off; 18 ms on, 18 ms off; 19 ms on, 19 ms off; 20 ms on, 20 ms off, etc.). In some embodiments, the on cycle and off cycle may have different durations in accordance with any of the ranges or durations noted herein. In some embodiments, the on cycle of the light modulation pattern may be longer than the off cycle of the light modulation pattern. In some embodiments, the off cycle of the light modulation pattern may be longer than the on cycle of the light modulation pattern.

As shown by operation 4702 of FIG. 47, the optical density instrument 1, including system 100 may include means, such as processing circuitry 110, processor 112, memory 114, communication interface 116, emitter 30 (shown in FIG. 15), and/or the like, for controlling at least one sensor to perform a dark reading while the at least one emitter (e.g., emitter 30) is off.

In some examples, the optical density instrument 1, including system 100 may be configured to control the sensors such that sensor readings begin after a predetermined time delay following tube insertion. For example, as indicated in FIG. 23, a delay (410) of 500 ms or other predetermined time may occur from the time of tube insertion to the start of sensor readings to account for the time needed for a user to insert the tube into the detection device after the apparatus detects the tube being inserted (e.g., using a physical, optical, or other type of switch).

A sensor reading may begin (412) and end (414) within a single off cycle of the illumination light 33. Once the sensor readings begin (412), sensor readings may be repeated on a continuous cycle, such as every 192 ms (416) until the tube is removed (420). The repeated sensor readings are described in further detail below with respect to operations 4712 and 4714.

In some embodiments, the sensor readings may be taken every off cycle of the illumination light 110 (e.g., an interval corresponding to any of the intervals of the off cycle of the light modulation pattern detailed herein). In some embodiments, the sensor readings may be taken after a predetermined number of off cycles of the illumination light. Said differently, the interval between readings (416) may be a multiple of the duty cycle 403 and off cycle duration 404. For example, in the embodiment depicted in FIG. 4, the interval between readings is 192 ms (416), which is a multiple (12×) of the 16 ms duty cycle (403).

In some embodiments, the interval between readings (416) may be less than 2 times the length of the duty cycle (403). In some embodiments, the interval between readings (416) may be less than 3 times the length of the duty cycle (403). In some embodiments, the interval between readings (416) may be less than 4 times the length of the duty cycle (403). In some embodiments, the interval between readings (416) may be less than 5 times the length of the duty cycle (403). In some embodiments, the interval between readings (416) may be less than 6 times the length of the duty cycle (403). In some embodiments, the interval between readings (416) may be less than 7 times the length of the duty cycle (403). In some embodiments, the interval between readings (416) may be less than 8 times the length of the duty cycle (403). In some embodiments, the interval between readings (416) may be less than 9 times the length of the duty cycle (403). In some embodiments, the interval between readings (416) may be less than 10 times the length of the duty cycle (403). In some embodiments, the interval between readings (416) may be less than 11 times the length of the duty cycle (403). In some embodiments, the interval between readings (416) may be less than 12 times the length of the duty cycle (403). In some embodiments, the interval between readings (416) may be less than 13 times the length of the duty cycle (403). In some embodiments, the interval between readings (416) may be less than 14 times the length of the duty cycle (403). In some embodiments, the interval between readings (416) may be less than 15 times the length of the duty cycle (403). In some embodiments, the interval between readings (416) may be less than 16 times the length of the duty cycle (403). In some embodiments, the interval between readings (416) may be less than 17 times the length of the duty cycle (403). In some embodiments, the interval between readings (416) may be less than 18 times the length of the duty cycle (403). In some embodiments, the interval between readings (416) may be less than 19 times the length of the duty cycle (403). In some embodiments, the interval between readings (416) may be less than 20 times the length of the duty cycle (403). In some embodiments, the interval between readings (416) may be less than 21 times the length of the duty cycle (403).

In some embodiments, the interval between readings (416) may be less than 500 ms. In some embodiments, the interval between readings (416) may be less than 300 ms. In some embodiments, the interval between readings (416) may be less than 450 ms. In some embodiments, the interval between readings (416) may be less than 400 ms. In some embodiments, the interval between readings (416) may be less than 350 ms. In some embodiments, the interval between readings (416) may be less than 300 ms. In some embodiments, the interval between readings (416) may be less than 250 ms. In some embodiments, the interval between readings (416) may be less than 200 ms. In some embodiments, the interval between readings (416) may be less than 150 ms. In some embodiments, the interval between readings (416) may be less than 100 ms. In some embodiments, the interval between readings (416) may be less than 50 ms.

In some embodiments, the interval between readings (416) may be 320 ms or less. In some embodiments, the interval between readings (416) may be 304 ms or less. In some embodiments, the interval between readings (416) may be 288 ms or less. In some embodiments, the interval between readings (416) may be 272 ms or less. In some embodiments, the interval between readings (416) may be 256 ms or less. In some embodiments, the interval between readings (416) may be 240 ms or less. In some embodiments, the interval between readings (416) may be 224 ms or less. In some embodiments, the interval between readings (416) may be 208 ms or less. In some embodiments, the interval between readings (416) may be 192 ms or less. In some embodiments, the interval between readings (416) may be 176 ms or less. In some embodiments, the interval between readings (416) may be 160 ms or less. In some embodiments, the interval between readings (416) may be 144 ms or less. In some embodiments, the interval between readings (416) may be 128 ms or less. In some embodiments, the interval between readings (416) may be 112 ms or less. In some embodiments, the interval between readings (416) may be 96 ms or less. In some embodiments, the interval between readings (416) may be 80 ms or less. In some embodiments, the interval between readings (416) may be 64 ms or less. In some embodiments, the interval between readings (416) may be 48 ms or less. In some embodiments, the interval between readings (416) may be 32 ms or less. In some embodiments, the interval between readings (416) may be 16 ms or less.

In some embodiments, the interval between readings (416) may be from 1 to 20 times the length of the duty cycle (403). In some embodiments, the interval between readings (416) may be from 2 to 20 times the length of the duty cycle (403). In some embodiments, the interval between readings (416) may be from 4 to 20 times the length of the duty cycle (403). In some embodiments, the interval between readings (416) may be from 6 to 20 times the length of the duty cycle (403). In some embodiments, the interval between readings (416) may be from 8 to 20 times the length of the duty cycle (403). In some embodiments, the interval between readings (416) may be from 10 to 20 times the length of the duty cycle (403). In some embodiments, the interval between readings (416) may be from 12 to 20 times the length of the duty cycle (403). In some embodiments, the interval between readings (416) may be from 14 to 20 times the length of the duty cycle (403). In some embodiments, the interval between readings (416) may be from 16 to 20 times the length of the duty cycle (403). In some embodiments, the interval between readings (416) may be from 18 to 20 times the length of the duty cycle (403). In some embodiments, the interval between readings (416) may be from 1 to 18 times the length of the duty cycle (403). In some embodiments, the interval between readings (416) may be from 1 to 16 times the length of the duty cycle (403). In some embodiments, the interval between readings (416) may be from 1 to 14 times the length of the duty cycle (403). In some embodiments, the interval between readings (416) may be from 1 to 12 times the length of the duty cycle (403). In some embodiments, the interval between readings (416) may be from 1 to 10 times the length of the duty cycle (403). In some embodiments, the interval between readings (416) may be from 1 to 8 times the length of the duty cycle (403). In some embodiments, the interval between readings (416) may be from 1 to 6 times the length of the duty cycle (403). In some embodiments, the interval between readings (416) may be from 1 to 4 times the length of the duty cycle (403). In some embodiments, the interval between readings (416) may be from 1 to 2 times the length of the duty cycle (403). In some embodiments, the interval between readings (416) may be from 6 to 18 times the length of the duty cycle (403). In some embodiments, the interval between readings (416) may be from 8 to 18 times the length of the duty cycle (403). In some embodiments, the interval between readings (416) may be from 10 to 18 times the length of the duty cycle (403). In some embodiments, the interval between readings (416) may be from 12 to 18 times the length of the duty cycle (403). In some embodiments, the interval between readings (416) may be from 14 to 18 times the length of the duty cycle (403). In some embodiments, the interval between readings (416) may be from 6 to 16 times the length of the duty cycle (403). In some embodiments, the interval between readings (416) may be from 6 to 14 times the length of the duty cycle (403). In some embodiments, the interval between readings (416) may be from 6 to 12 times the length of the duty cycle (403). In some embodiments, the interval between readings (416) may be from 6 to 10 times the length of the duty cycle (403). In some embodiments, the interval between readings (416) may be from 6 to 8 times the length of the duty cycle (403).

In some embodiments, the interval between readings (416) may be from 100 ms to 500 ms. In some embodiments, the interval between readings (416) may be from 150 ms to 500 ms. In some embodiments, the interval between readings (416) may be from 200 ms to 500 ms. In some embodiments, the interval between readings (416) may be from 250 ms to 500 ms. In some embodiments, the interval between readings (416) may be from 300 ms to 500 ms. In some embodiments, the interval between readings (416) may be from 350 ms to 500 ms. In some embodiments, the interval between readings (416) may be from 400 ms to 500 ms. In some embodiments, the interval between readings (416) may be from 450 ms to 500 ms. In some embodiments, the interval between readings (416) may be from 100 ms to 450 ms. In some embodiments, the interval between readings (416) may be from 100 ms to 400 ms. In some embodiments, the interval between readings (416) may be from 100 ms to 350 ms. In some embodiments, the interval between readings (416) may be from 100 ms to 300 ms. In some embodiments, the interval between readings (416) may be from 100 ms to 250 ms. In some embodiments, the interval between readings (416) may be from 100 ms to 200 ms. In some embodiments, the interval between readings (416) may be from 100 ms to 150 ms. In some embodiments, the interval between readings (416) may be from 192 ms to 256 ms. In some embodiments, the interval between readings (416) may be from 192 ms to 240 ms. In some embodiments, the interval between readings (416) may be from 192 ms to 224 ms. In some embodiments, the interval between readings (416) may be from 192 ms to 208 ms. In some embodiments, the interval between readings (416) may be from 176 ms to 192 ms. In some embodiments, the interval between readings (416) may be from 160 ms to 192 ms. In some embodiments, the interval between readings (416) may be from 144 ms to 192 ms. In some embodiments, the interval between readings (416) may be from 128 ms to 192 ms. In some embodiments, the interval between readings (416) may be from 176 ms to 256 ms. In some embodiments, the interval between readings (416) may be from 176 ms to 240 ms. In some embodiments, the interval between readings (416) may be from 176 ms to 224 ms. In some embodiments, the interval between readings (416) may be from 176 ms to 208 ms. In some embodiments, the interval between readings (416) may be from 176 ms to 192 ms. In some embodiments, the interval between readings (416) may be from 160 ms to 176 ms. In some embodiments, the interval between readings (416) may be from 144 ms to 176 ms. In some embodiments, the interval between readings (416) may be from 128 ms to 176 ms. In some embodiments, the interval between readings (416) may be from 144 ms to 256 ms. In some embodiments, the interval between readings (416) may be from 144 ms to 240 ms. In some embodiments, the interval between readings (416) may be from 144 ms to 224 ms. In some embodiments, the interval between readings (416) may be from 144 ms to 208 ms. In some embodiments, the interval between readings (416) may be from 144 ms to 192 ms. In some embodiments, the interval between readings (416) may be from 144 ms to 176 ms. In some embodiments, the interval between readings (416) may be from 144 ms to 160 ms. In some embodiments, the interval between readings (416) may be from 128 ms to 144 ms. In some embodiments, the interval between readings (416) may be from 128 ms to 256 ms. In some embodiments, the interval between readings (416) may be from 128 ms to 240 ms. In some embodiments, the interval between readings (416) may be from 128 ms to 224 ms. In some embodiments, the interval between readings (416) may be from 128 ms to 208 ms. In some embodiments, the interval between readings (416) may be from 128 ms to 192 ms. In some embodiments, the interval between readings (416) may be from 128 ms to 176 ms. In some embodiments, the interval between readings (416) may be from 128 ms to 160 ms. In some embodiments, the interval between readings (416) may be from 208 ms to 256 ms. In some embodiments, the interval between readings (416) may be from 208 ms to 240 ms. In some embodiments, the interval between readings (416) may be from 208 ms to 224 ms. In some embodiments, the interval between readings (416) may be from 192 ms to 208 ms. In some embodiments, the interval between readings (416) may be from 176 ms to 208 ms. In some embodiments, the interval between readings (416) may be from 160 ms to 208 ms. In some embodiments, the interval between readings (416) may be from 144 ms to 208 ms. In some embodiments, the interval between readings (416) may be from 128 ms to 208 ms. In some embodiments, the interval between readings (416) may be from 224 ms to 256 ms. In some embodiments, the interval between readings (416) may be from 224 ms to 240 ms. In some embodiments, the interval between readings (416) may be from 208 ms to 240 ms. In some embodiments, the interval between readings (416) may be from 192 ms to 224 ms. In some embodiments, the interval between readings (416) may be from 176 ms to 224 ms. In some embodiments, the interval between readings (416) may be from 160 ms to 224 ms. In some embodiments, the interval between readings (416) may be from 144 ms to 224 ms. In some embodiments, the interval between readings (416) may be from 128 ms to 224 ms. In some embodiments, the interval between readings (416) may be from 240 ms to 256 ms. In some embodiments, the interval between readings (416) may be from 224 ms to 240 ms. In some embodiments, the interval between readings (416) may be from 208 ms to 240 ms. In some embodiments, the interval between readings (416) may be from 192 ms to 240 ms. In some embodiments, the interval between readings (416) may be from 176 ms to 240 ms. In some embodiments, the interval between readings (416) may be from 160 ms to 240 ms. In some embodiments, the interval between readings (416) may be from 144 ms to 240 ms. In some embodiments, the interval between readings (416) may be from 128 ms to 240 ms. In some embodiments, the interval between readings (416) may be from 224 ms to 256 ms. In some embodiments, the interval between readings (416) may be from 208 ms to 256 ms. In some embodiments, the interval between readings (416) may be from 192 ms to 256 ms. In some embodiments, the interval between readings (416) may be from 176 ms to 256 ms. In some embodiments, the interval between readings (416) may be from 160 ms to 256 ms. In some embodiments, the interval between readings (416) may be from 144 ms to 256 ms. In some embodiments, the interval between readings (416) may be from 128 ms to 256 ms.

FIG. 24 is an exploded view of an 8 ms off cycle (500) of the illumination light. In some examples, processing circuitry 110 may control the emitter 30 and/or sensors such that sensor readings are performed following a predetermined time delay (510) following turnoff of the illumination light (520). For example, processing circuitry 110 may control the emitter 30 to emit a signal after 2 ms following the end of an on cycle of the light modulation pattern. In this regard, electrons may settle and the ambient light in the vicinity of the sample tube may stabilize, thereby reducing, minimizing, and/or preventing interference of the illumination light with any of the sensors.

Indicator 530 represents a dark reading(s) performed by a sensor. For example, "D" and "N" of readings 530 represent readings respectively performed by density sensor 31 and nephelometric sensor 32. The term "dark" in dark reading refers to the off status of the emitter 30 and the term dark reading is therefore not intended to be limiting. In some embodiments, the dark reading is used for calibrating any of the sensors to account for ambient light, as described in further detail below. In some embodiments, the dark readings 530 may be less than 1 ms combined. In some embodiments, the dark readings 530 may be 800 microseconds combined. In some embodiments, the dark readings 530 may be 800 microseconds or less combined. In some embodiments, the dark reading time may include an analog to digital conversion (ADC) time and a firmware (FW) execution time.

As described with respect to operation 4704 in FIG. 47, and as shown by indicator 540 in FIG. 24, the optical density instrument 1 may include means, such as processing circuitry 110, processor 112, memory 114, emitter 30, and/or the like, for during an off cycle of the light modulation pattern, controlling at least one emitter to emit a signal (e.g., source light) for detection by at least one sensor.

At operation 4706, the optical density instrument 1 may also include means, such as processing circuitry 110, processor 112, memory 114, density sensor 31, nephelometric sensor 32, any other sensor of the detection device, and/or the like, for controlling the at least one sensor to perform a light reading during the off cycle of the light modulation pattern and while the at least one emitter is on.

In this regard, following an optional predetermined time delay (550), the optical density instrument 1 may direct the sensors to perform a light reading 560. The optional predetermined time delay, such as 4 ms, may be variable, and may be configured to allow the signal or source light emitted from the emitter 540 to be detected by a sensor. Readings "D" and "N" of readings 560 represent light readings respectively performed by density sensor 31 and nephelometric sensor 32. The term "light" in light reading refers to the on or emitting status of the emitter 540 and is not intended to be limiting. For instance, it will be appreciated that the illumination light may indeed be off during a light reading, as is illustrated in FIG. 24. In some embodiments, the light readings 560 may be less than 1 ms combined. In some embodiments, the light readings 560 may be 800 microseconds combined. In some embodiments, the light readings 560 may be 800 microseconds or less combined. In some embodiments, the light reading time may include an analog to digital conversion (ADC) time and a firmware (FW) execution time.

At operation 4708, the optical density instrument 1 may include means, such as processing circuitry 110, processor 112, memory 114, and/or the like, for determining an ambient light offset by subtracting a dark reading from a light reading. In this regard, the converted and/or digitized readings from the sensors may be used to calculate a quantifiable ambient light offset.

At operation 4710, the optical density instrument 1 may include means, such as processing circuitry 110, processor 112, memory 114, communication interface 116, and/or the like, for calibrating sensor readings according to the ambient light offset. In this regard, the ambient light detected by comparing the dark reading to a light reading may be used to adjust subsequent readings such that the sensor readings account for ambient light. The ambient light offset may be a coefficient or other factor that when applied to a reading performed by a sensor, the adjusted or calibrated reading may account for ambient light such that sensor readings may be more uniformly and/or accurately provided despite ambient light conditions. In this regard, a dark reading and/or calculation of the ambient light offset may occur once following sample tube insertion or may be repeated any number of times during repeated cycle readings (for example, for each light reading, or for every predetermined number of light readings).

At operation 4712, the optical density instrument 1 may include means, such as processing circuitry 110, processor 112, memory 114, density sensor 31, nephelometric sensor 32, any other sensor of the detection device, and/or the like, for controlling the at least one sensor to perform a plurality of readings (e.g., light readings) over a plurality of off cycles in the light modulation pattern. The sensor readings may be repeated on a predetermined time interval, such as 192 ms or any other interval discussed herein. Additionally or alternatively, a sensor repeating may be repeated based on an elapsed number of on-off cycles of the illumination light (e.g., 12 cycles). In some embodiments, the optical density instrument 1 may cause a sensor reading to occur after the time interval (e.g., 192 ms) has elapsed and the illumination light has cycled off, as illustrated in FIGS. 23 (416 and 418).

At operation 4714, the optical density instrument 1 may include means, such as processing circuitry 110, processor 112, memory 114, and/or the like, for calculating a moving average sensor reading based on the plurality of readings. Example embodiments, may, for example, use a predetermined number of previous readings to calculate a moving average to provide to a user via a user interface or to another device. For example, three previous readings may be used as the predetermined number of readings to incorporate into a moving average. The moving average may serve as a smoothing mechanism for providing readings to another device and/or to a user via a user interface, for example.

In some examples, optical density instrument 1 may utilize sensor readings from various sensors and/or sensor types, process the sensor readings to calculate a property of a suspension, and provide a moving average. For example, as described in further detail below, optical density instrument 1 may use a reading from both a density sensor 31 and a nephelometric sensor 32 to determine a McFarland value. In this regard, a reading from both the density sensor 31 and nephelometric sensor 32 may be combined and manipulated to determine a McFarland value, and the readings may be repeated according to configurations of the optical density instrument 1, and may be represented as a moving average over time. Additionally or alternatively, example embodiments may calculate a moving average based on sensor readings taken from a single sensor.

The 192 ms period on which to repeat sensor readings, and the three-point moving average are provided merely as examples and it will be appreciated that any pattern of sensor readings and moving averages may be used. For example, a 192 ms period and three-point moving average may be determined as appropriate parameters by which to collect data from the density sensor 31 and/or nephelometric sensor 32 and provide resultant data to a user or other computing device based on desired user experience and/or variability in the reported data. However, in some embodiments, optical density instrument 1 may determine other periods on which to repeat readings and/or other numbers of samples to be used in a moving average depending on a variety of factors such as sensor type, sensor sensitivity, estimated variability in a measured characteristic of the suspension, and/or desired variability in resultant data.

In some embodiments, optical density instrument 1, including system 100 may advantageously utilize readings from both the density sensor 31 and nephelometric sensor 32 in determining a McFarland value. McFarland values may be used as a reference to adjust turbidity in a suspension so that the concentration of microorganisms may be a specified value or within a range of values to standardize testing.

Figure 48:
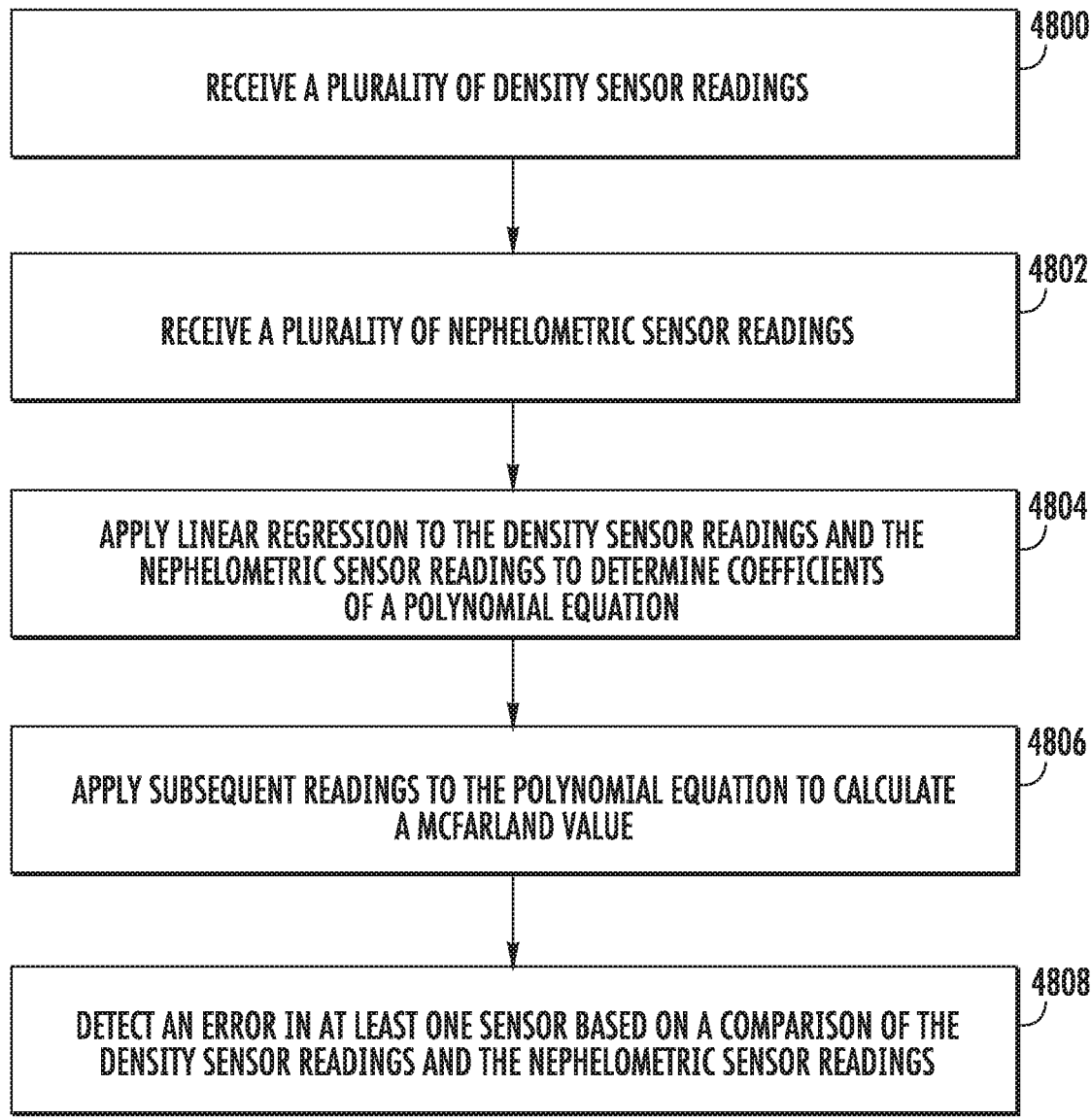
FIG. 48 is a flowchart illustrating operations according to an example embodiment.

FIG. 48 is a flowchart illustrating example operations of the optical density instrument 1, including system 100 according to some example embodiments. In operation 4800, the system 100 may include means, such as processing circuitry 110, processor 112, memory 114, communication interface 116, density sensor 31, and/or the like, for receiving a plurality of density sensor readings. In operation 4802, the optical density instrument 1, including system 100 may include means, such as processing circuitry 110, processor 112, memory 114, communication interface 116, nephelometric sensor 32, and/or the like, for receiving a plurality of nephelometric sensor readings.

Figure 49:
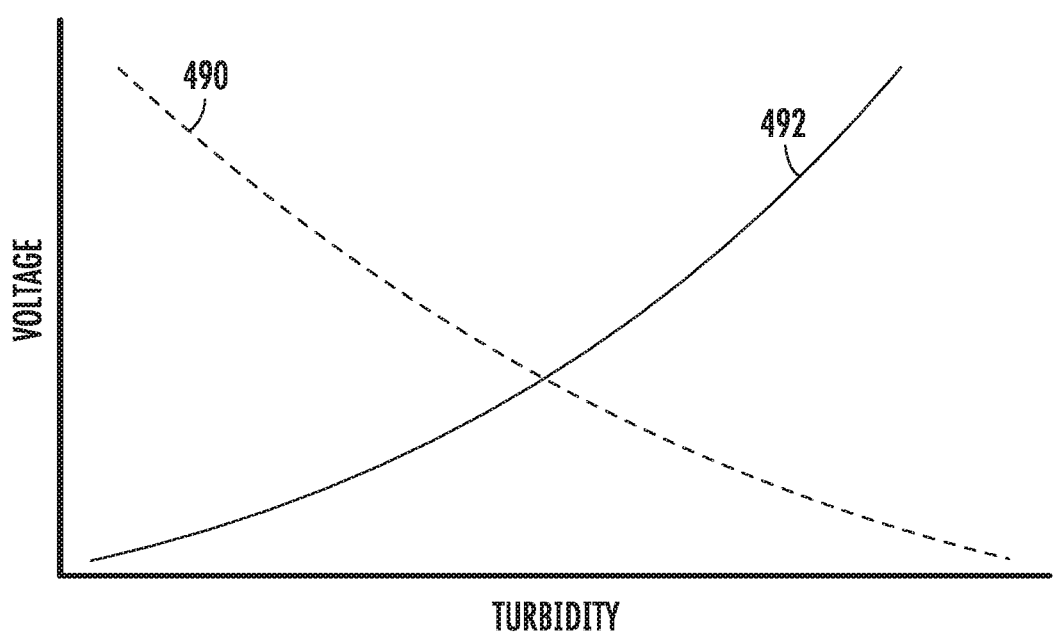
FIG. 49 is an example plot of sensor readings according to an example embodiment.

FIG. 49 is an example plot of density sensor readings 490 and nephelometric sensor readings 492 according to example embodiments. The readings are plotted as voltages relative to the turbidity of the liquid, and may be non-linear.

In some embodiments, as turbidity increases, nephelometric readings increase, and density readings decrease. In some examples, a density sensor reading may be more sensitive for lower turbidity liquids relative to the sensitivity of the nephelometric readings, whereas nephelometric readings may be more sensitive for higher turbidity liquids relative to the sensitivity of density readings. A polynomial equation may therefore account for the varying impact of the two types of data on the McFarland value.

In some embodiments, optical density instrument 1, including system 100 may determine a polynomial equation or model by applying linear regression to the two readings, the output of which provides a McFarland value of the liquid. Said differently, system 100 may calibrate the two signals to generate a McFarland value. In some embodiments, this calibration may be conducted using known samples across a wide range of McFarland values.

Accordingly, in operation 4804, the optical density instrument 1, including system 100 may include means, such as processing circuitry 110, processor 112, memory 114, communication interface 116, and/or the like, for applying linear regression to the density sensor readings and the nephelometric sensor readings to determine coefficients of a polynomial equation. And, in operation 4804, the optical density instrument 1, including system 100 may include means, such as processing circuitry 110, processor 112, memory 114, communication interface 116, and/or the like, for applying subsequent readings to the polynomial equation to calculate a McFarland value.

In some embodiments, in operation 4808, the optical density instrument 1, including system 100 may include means, such as processing circuitry 110, processor 112, memory 114, communication interface 116, and/or the like, for detecting an error in at least one sensor based on a comparison of the density sensor readings and the nephelometric sensor readings. Given previous density sensor readings and/or nephelometric sensor readings, optical density instrument 1, including system 100 may be configured to detect a change in one of the sensor readings relative to the other and/or based on the determined polynomial equation. For example, an abnormal reading(s) from one sensor relative to readings of the other sensor, in comparison to a pattern of past density sensor readings and/or nephelometric sensor readings relative to each other may indicate a dirty sensor or window positioned in between a sensor and tube.

In some embodiments, in response to detecting an error, the optical density instrument 1, including system 100 may be further configured to calculate a McFarland value based on a correctly functioning sensor(s) not subject to the detected error. Said differently, example embodiments may exclude sensor readings detected from a sensor for which an error is detected. The optical density instrument 1, including system 100 may therefore continue to provide McFarland values and/or alert a user to clean device components and/or to troubleshoot the issue.

Figure 50:
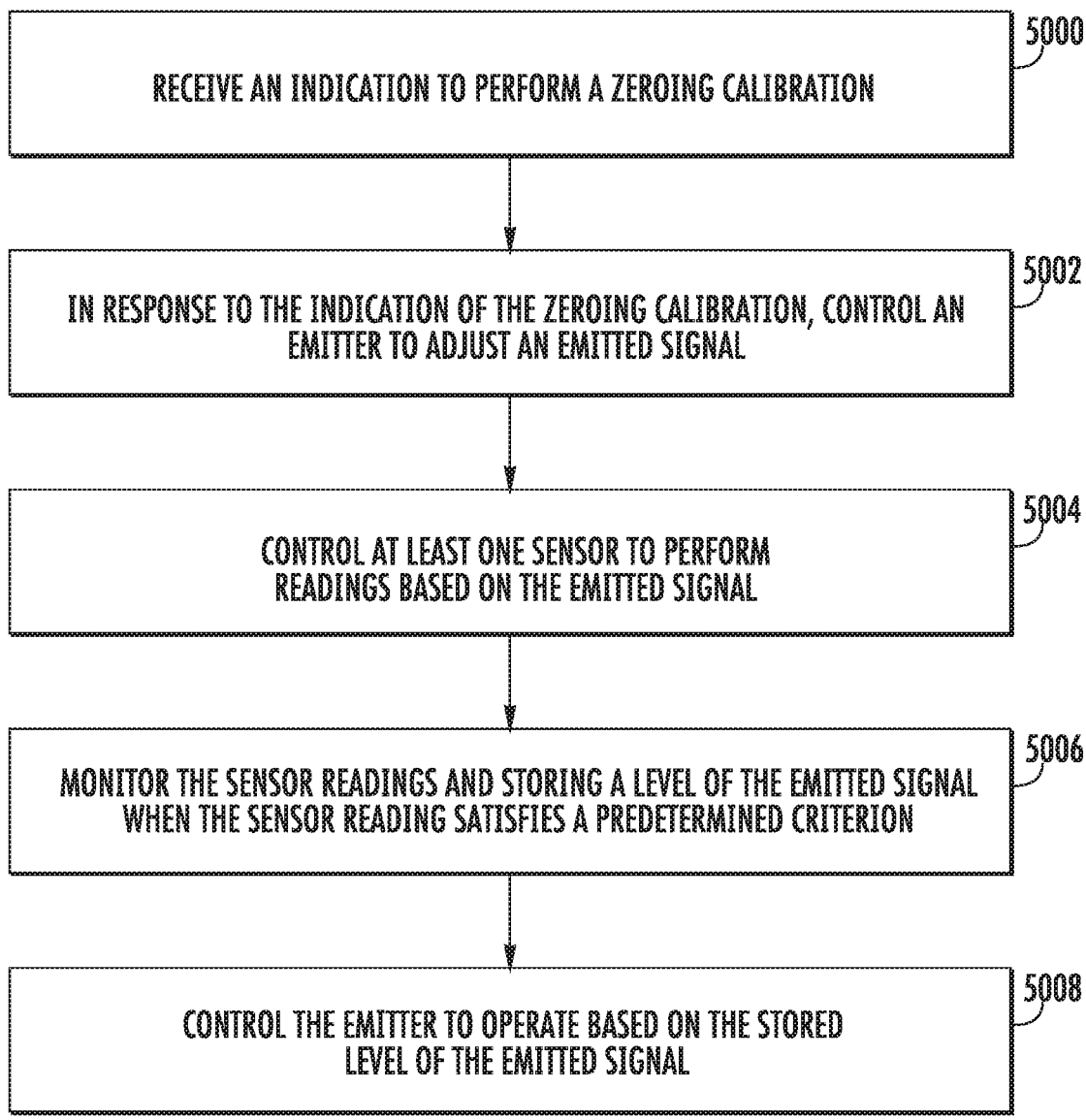
FIG. 50 is a flowchart illustrating operations according to an example embodiment.

FIG. 50 is a flowchart illustrating example operations of optical density instrument 1, including system 100 according to some example embodiments. In operation 5000, the optical density instrument 1, including system 100 may include means, such as processing circuitry 110, processor 112, memory 114, communication interface 116, user interface 130, and/or the like, for receiving an indication to perform a zeroing calibration. A user may insert a baseline tube into the detection device, and indicate via user interface 130 to zero the detection device. As another example, the indication may be generated in response to detection of a baseline tube being inserted into the detection device.

In operation 5002, the optical density instrument 1, including system 100 may include means, such as processing circuitry 110, processor 112, memory 114, communication interface 116, emitter 30, and/or the like, for in response to the indication of the zeroing calibration, controlling an emitter (e.g., emitter 30) to adjust an emitted signal. For example, when emitter 30 is embodied as an LED, optical density instrument 1, including system 100 may cause the current to be gradually stepped up. The LED may be driven by a digital-to-analog converter, such as a 12-bit converter configured to enable the LED to emit 4,096 different levels of current.

As the emitter 30 is gradually stepped up, sensor readings may be performed based on the various signals. In this regard, at operation 5004, the optical density instrument 1, including system 100 may include means, such as processing circuitry 110, processor 112, memory 114, communication interface 116, density sensor 31, nephelometric sensor 32, any other type sensors and/or the like, for controlling at least one sensor to perform readings based on the emitted signal.

In operation 5006, the optical density instrument 1, including system 100 may include means, such as processing circuitry 110, processor 112, memory 114, communication interface 116, emitter 30, and/or the like, for monitoring the sensor readings and storing a level of the emitted signal when the sensor reading satisfies a predetermined criterion. The predetermined criterion may be a predetermined target value or range of values the sensor is expected to detect based on an empty tube and/or clear saline solution. As another example, the predetermined criterion may be predetermined target value or range of values of a calculation performed based on a sensor reading, such as a McFarland value calculated based on a density sensor reading and/or nephelometric sensor reading. For example, optical density instrument 1, including system 100 may be pre-configured with an expected value or range of values for the density sensor 31 (and/or other types of sensors). Once the target value or range is reached, the level of current emitted by the emitter 30 may be recorded. The calibration may further allow the transmitted signal to normalize by tracking the sensor reading for a period of time and waiting until there is no drift. The normalization may occur before, during, or after the step up of the emitter current, or may be conducted separately therefrom.

In operation 5008, the apparatus optical density instrument 1, including system 100 may include means, such as processing circuitry 110, processor 112, memory 114, communication interface 116, emitter 30, and/or the like, for controlling the emitter to operate based on the stored level of the emitted signal. In this regard, the optical density instrument 1, including system 100 may use the calibration (e.g., stored level of emitted signal or current) until the next zeroing calibration occurs. A user may re-zero the detection device when the detection device is turned on, when beginning to use a different type of tube, and/or when ambient conditions change.

The operations described herein may therefore reduce the interference of the illumination light in sensor readings, and may therefore improve the accuracy of the sensor readings, while still providing improved visibility of liquid in the sample tube. Further details regarding the operation of the sensors, including calibration, zeroing, and data collection, may be found in U.S. Provisional Application No. 62/487,736, entitled "Method, Apparatus, and Computer Program for Controlling Components of a Detection Device," and filed Apr. 20, 2017, which application is incorporated by reference herein in its entirety.

In this regard, the method provides additional convenience, comfort, and safety over existing density measurement methods.

IV. Non-Limiting Exemplary Embodiments

In accordance with certain embodiments, the optical density instrument includes a handheld unit having a top and a bottom and a base station having at least a handheld unit receiving portion such that the handheld unit is configured to operably couple to the base station both when the handheld unit engages the handheld unit receiving portion and when the handheld unit is separated from the base station. The handheld unit further includes an optical test platform having an open top and a cavity configured to receive at least a portion of a first sample tube and a bottom portion positioned within the handheld unit such that the first sample tube extends above the top of the handheld unit when inserted in the optical test platform. Moreover, the handheld unit includes an emitter positioned within the handheld unit at the bottom portion of the optical test platform such that the emitter is configured to emit light into the cavity, and the emitter is configured to emit light into the first sample tube when the first sample tube is inserted in the optical test platform. Additionally, the handheld unit includes at least one sensor positioned in optical communication with the emitter via the cavity, such that the at least one sensor is configured to receive the emitted light from the cavity, and such that the at least one sensor is configured to receive light emitted by the emitter and passing through the first sample tube when the first sample tube is inserted in the optical test platform. In addition, the handheld unit includes an illumination light positioned at the bottom portion of the optical test platform that is configured to illuminate the first sample tube when the first sample tube is inserted in the optical test platform.

According to certain embodiments, the emitter may be configured to emit a source light through a sample disposed in the first sample tube, and the at least one sensor is configured to detect a portion of the source light that is transmitted through the sample. In some embodiments, the emitter and the illumination light may be configured to emit light according to a light modulation pattern. In further embodiments, at least one of the emitter or the illumination light may include a light emitting diode.

According to certain embodiments, the at least one sensor comprises at least two sensors including a density sensor and a nephelometric sensor. In such embodiments, the density sensor may be positioned opposite the emitter relative to the cavity to detect source light transmitted through a sample contained in at least one of the sample tubes, and the nephelometric sensor may be positioned perpendicular to an axis spanning the density sensor and the emitter to detect source light reflected by a sample in the sample tube.

According to certain embodiments, the base station may further include a display screen. In such embodiments, the display screen may be configured to present data transmitted to the base station by the handheld unit. In some embodiments, the optical density instrument may further include processing circuitry configured to control operations of at least the emitter, the illumination light, and the at least one sensor to generate raw light data, convert the raw light data into optical density data, and communicate the optical density data to a display screen in real time.

According to certain embodiments, the top of the handheld unit may be open to allow a user to visually inspect a sample contained in the first sample tube and illuminated by the illumination light. In some embodiments, the handheld unit may include a substantially hourglass shape, and the top of the handheld unit may be narrower than the bottom. In further embodiments, the bottom of the handheld unit may include a plurality of non-skid feet.

In another aspect, certain embodiments according to the invention provide a system for measuring optical density of a sample. In accordance with certain embodiments, the system includes a handheld unit having a top and a bottom, a base station having at least a handheld unit receiving portion such that the handheld unit is configured to operably couple to the base station both when the handheld unit engages the handheld unit receiving portion and when the handheld unit is separated from the base station, and a computing device having a user interface. The handheld unit further includes an optical test platform having an open top and a cavity configured to receive at least a portion of a first sample tube and a bottom portion positioned within the handheld unit such that the first sample tube extends above the top of the handheld unit when inserted in the optical test platform. Moreover, the handheld unit includes an emitter positioned within the handheld unit at the bottom portion of the optical test platform such that the emitter is configured to emit light into the cavity, and the emitter is configured to emit light into the first sample tube when the first sample tube is inserted in the optical test platform. Additionally, the handheld unit includes at least one sensor positioned in optical communication with the emitter via the cavity, such that the at least one sensor is configured to receive the emitted light from the cavity, and such that the at least one sensor is configured to receive light emitted by the emitter and passing through the first sample tube when the first sample tube is inserted in the optical test platform. In addition, the handheld unit includes an illumination light positioned at the bottom portion of the optical test platform that is configured to illuminate the first sample tube when the first sample tube is inserted in the optical test platform.

According to certain embodiments, the system may further include processing circuitry configured to control operations of at least the emitter, the illumination light, and the at least one sensor to generate raw light data, convert the raw light data into optical density data, communicate the optical density data to a display screen in real time, and communicate the optical density data to the user interface. In some embodiments, the processing circuitry may be configured to continuously communicate the optical density data to the user interface.

According to certain embodiments, the emitter may be configured to emit a source light through a sample disposed in the first sample tube, and the at least one sensor is configured to detect a portion of the source light that is transmitted through the sample. In some embodiments, the emitter and the illumination light may be configured to emit light according to a light modulation pattern. In further embodiments, at least one of the emitter or the illumination light may include a light emitting diode.

According to certain embodiments, the at least one sensor comprises at least two sensors including a density sensor and a nephelometric sensor. In such embodiments, the density sensor may be positioned opposite the emitter relative to the cavity to detect source light transmitted through a sample contained in at least one of the sample tubes, and the nephelometric sensor may be positioned perpendicular to an axis spanning the density sensor and the emitter to detect source light reflected by a sample in the sample tube.

According to certain embodiments, the base station may further include a display screen in communication with the handheld unit. In some embodiments, the display screen may be configured to present data transmitted to the base station by the handheld unit.

According to certain embodiments, the top of the handheld unit may be open to allow a user to visually inspect a sample contained in the first sample tube and illuminated by the illumination light. In some embodiments, the handheld unit may include a substantially hourglass shape, and the top of the handheld unit may be narrower than the bottom. In further embodiments, the open top of the optical test platform may be further configured to receive a second sample tube. In some embodiments, the first sample tube may be affixed to the second sample tube. In further embodiments, the bottom of the handheld unit may include a plurality of non-skid feet.

In yet another aspect, certain embodiments according to the invention provide a method for measuring optical density of sample. In accordance with certain embodiments, the method includes receiving a first sample tube containing the sample, illuminating the sample in the first sample tube for visual inspection by a user according to a light modulation pattern, emitting a source light through the sample in the first sample tube according to the light modulation pattern, detecting a portion of the source light transmitted through or reflected by the sample to generate raw light data, and converting the raw light data into optical density data.

According to certain embodiments, the method may further include communicating the optical density data to a display screen. In some embodiments, the method may further include communicating the optical density data to a user interface. In further embodiments, communicating the optical density data to the user interface may occur continuously. In certain embodiments, illuminating the sample may occur concurrently with at least emitting the source light or detecting the source light. In some embodiments, the light modulation pattern may comprise illuminating the sample and emitting the source light at different times.

V. Calibration and Operation

Figure 25:
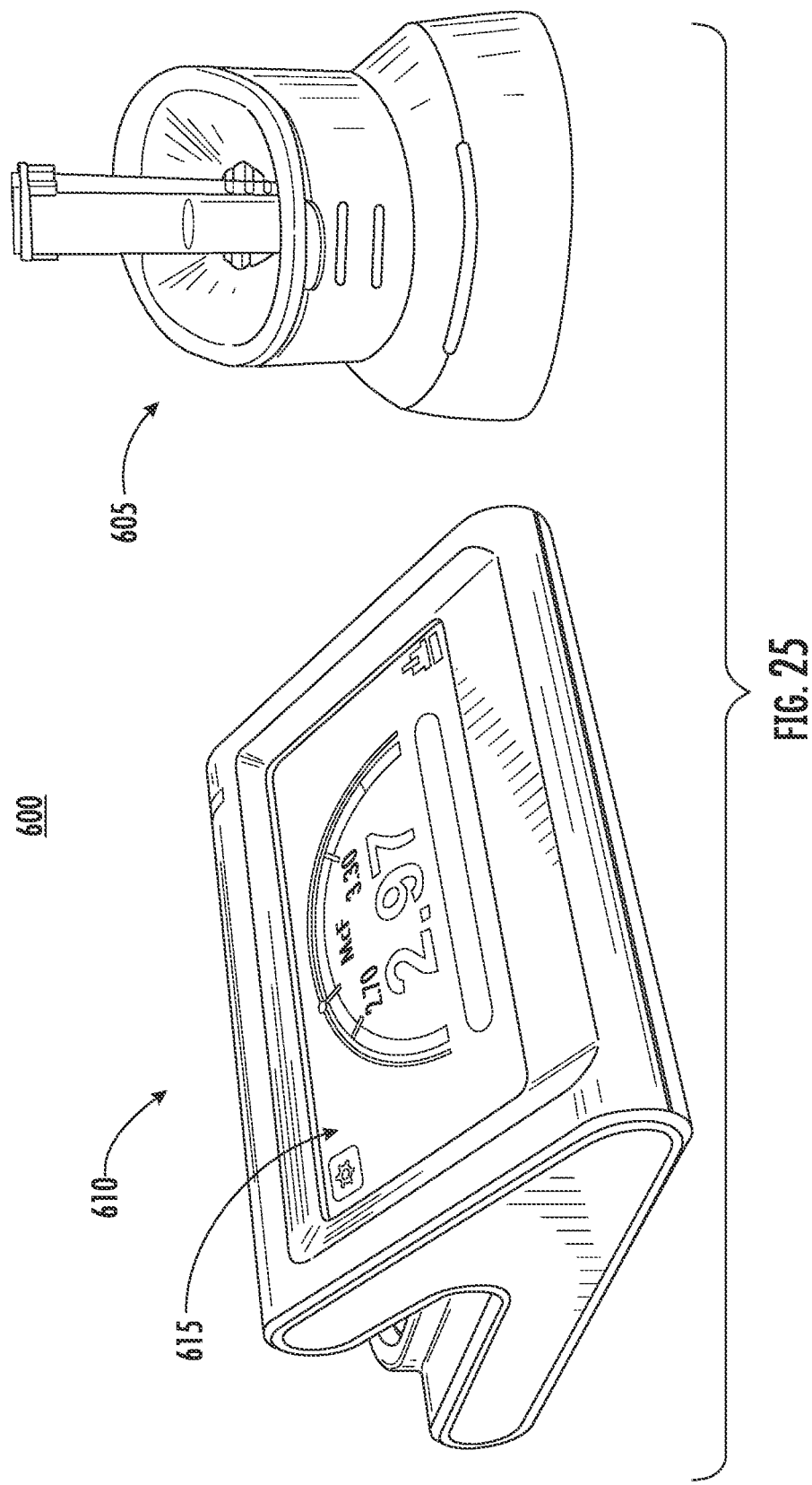
FIG. 25 is another example view of an optical density instrument in accordance with some embodiments discussed herein.
Figure 26:
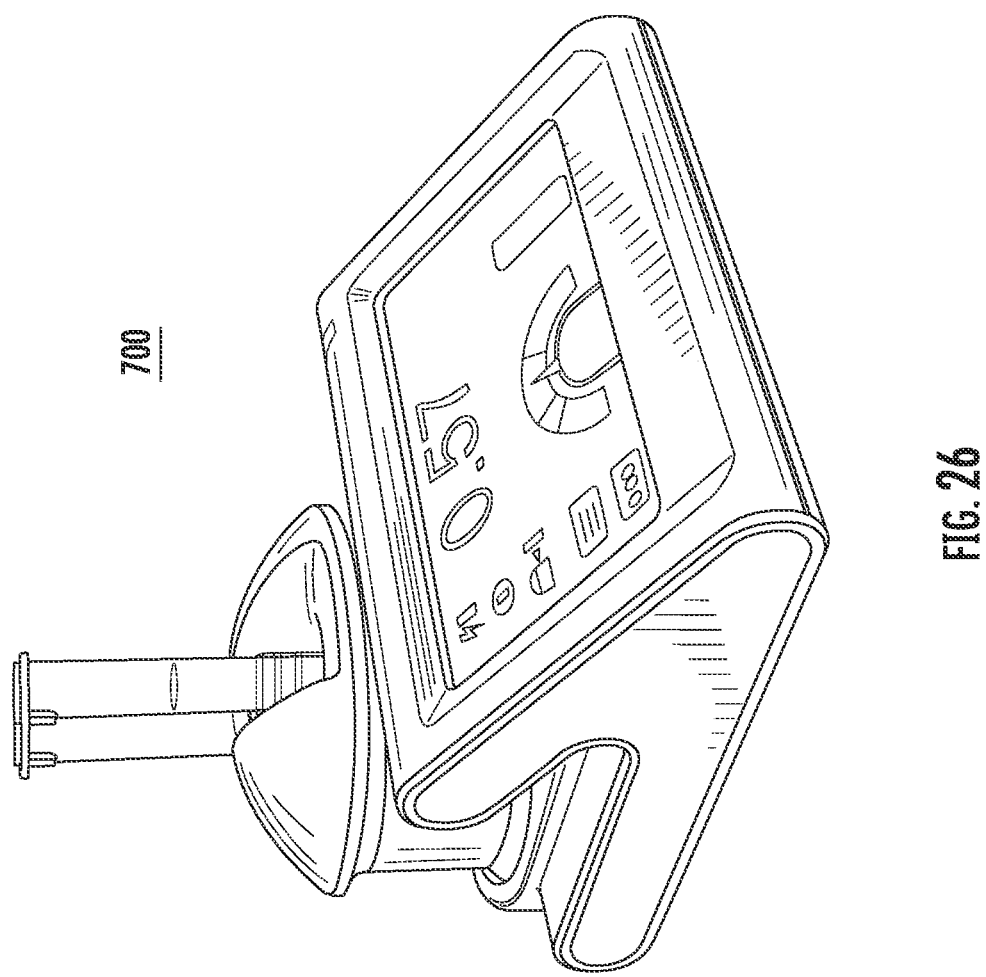
FIG. 26 is another example of an optical density instrument in accordance with some embodiments discussed herein.
Figure 32:
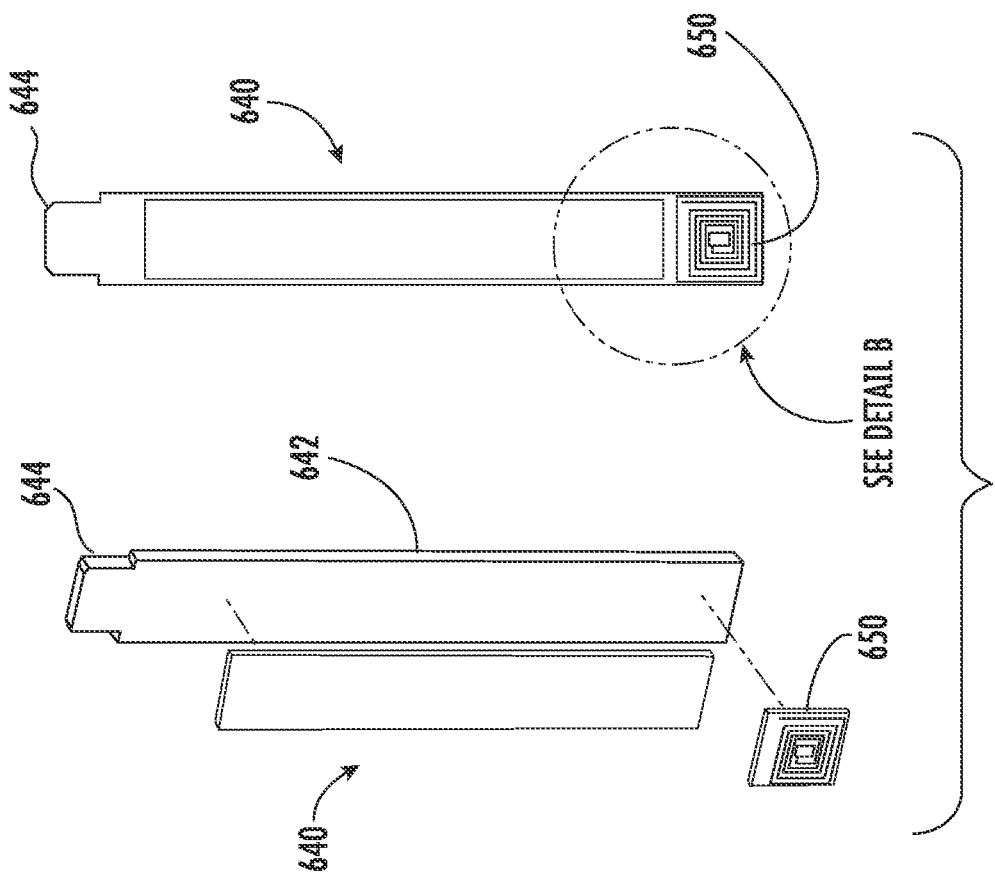
FIG. 32 shows a calibration tag in accordance with some embodiments discussed herein.
Figure 31:
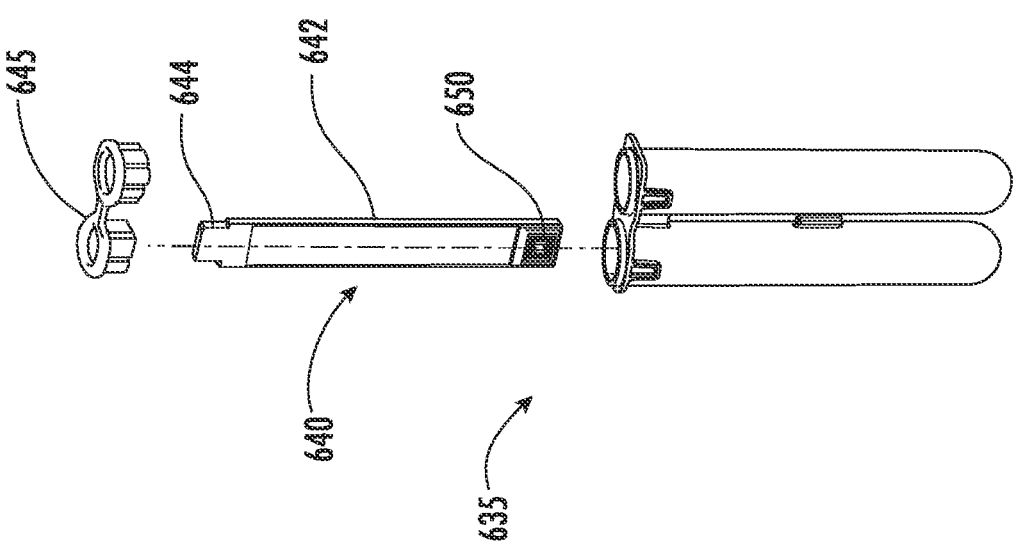
Figure 33:
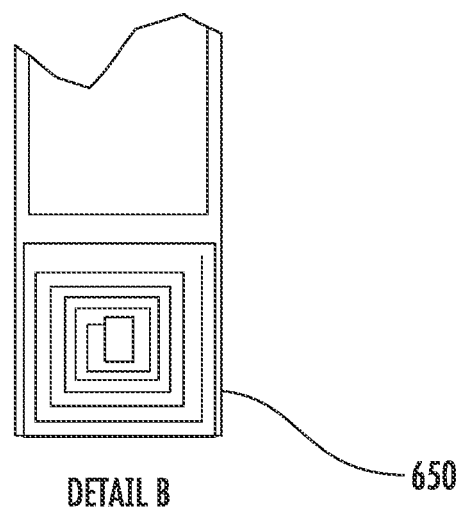
FIG. 33 shows a portion of the calibration tag of FIG. 32.

With reference to FIG. 25, an example embodiment of a handheld unit 605 and display base 610 of an optical density instrument 600 is shown having visual indicators on the display, and the features and operation of the optical density instrument 600 may be substantially the same as the other optical density instruments described herein. In some embodiments, the display 615 may be a touchscreen displaying a McFarland value. The range scale of the display may be appropriated according to the type of card (e.g., the downstream antibiotic susceptibility testing (AST) card used with the diluted sample from the sample tubes), and the screen may provide visual indicators (e.g., bars shown at 2.70 and 3.30 McFarland on the screen 615) of the optical density of the sample compared to the needed range for downstream testing. FIG. 26 also shows an example instrument 700, which may otherwise operate in accordance with any of the embodiments detailed herein.

In some embodiments, the instrument may generate real time readings using a two sensor, densitometric and nephelometric configuration described herein. In some embodiments, the optical testing instrument may operate in stand-alone mode or connected mode. In connected mode, the instrument may connect and communicate with another computing device (e.g., a VITEK2™ Flexprep™ screen). The instrument may be configured to send the measured McFarland value to a downstream testing machine (e.g., a VITEK2™ machine), and the instrument may receive a desired McFarland range and/or determine the desired McFarland range based on the card or other downstream testing apparatus.

In some embodiments, a calibration checking mode may be used with a specialized dual tube assembly. In operation, a known standard, corresponding to a known McFarland value, may be placed into the instrument to verify its calibration. With reference to FIGS. 27-33, a calibration dual sample tube 635 may be used to verify the calibration. The calibration tube 635 may contain a programmed RFID chip 650 or other transmitter or electronic identifier as part of a calibration tag 640, which chip contains the McFarland value that is expected for the calibration tubes 635. The optical density instrument 1 may, in turn, have a corresponding receiver and/or reader connected to the processing circuitry 110 for detecting the RFID tag (e.g., via passive or active RFID from the tag). The tag may include an inert body 642 with the chip 650 disposed at one end. For example, the distal end of the body 642 closest to the instrument in operation. In some embodiments, the body 642 may include a notched end 644 opposite the distal end, and the notched end 644 may engage a cap 645 on the tube. In some further embodiments, a label (shown in FIGS. 27 and 29) identifying the calibrant's McFarland value may also be placed on the tubes 635.

The instrument 1, 605 may receive the calibration value and check the calibration result as compared to the standard. In some embodiments, the calibration tubes 635 may include a tagged tube 637 (shown in FIG. 30) having a calibration tag 640 (shown in FIGS. 30-32) for communicating the McFarland value of the calibration sample to the instrument, and the tubes 635 may include a calibrant tube 639 containing a calibrant sample for verifying and/or updating the calibration of the instrument. In some embodiments, the calibrant sample may be a medium of silicone and $TiO_2$. In embodiments of the instrument that only test one of the two tubes 635, the calibrant tube 639 may be optically interrogated by the optical density components and the tagged tube 637 may be positioned in the other cavity of the handheld unit.

The tubes may be used, for example, by a customer to check the calibration of the instrument, and a plurality of tubes 635 may be used at predetermined McFarland thresholds (e.g., every half McFarland value—0.5, 1, 1.5, 2, 2.5, 3, 3.5, and 4 McFarland). The instrument may use a smaller amount of tubes 635 to verify calibration (e.g., 1, 2, 3, and 4 McFarland value tubes) and a larger amount of tubes 635 to re-calibrate the instrument (e.g., 0.5, 1, 1.5, 2, 2.5, 3, 3.5, and 4 McFarland value tubes).

VI. Conclusion

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIGS. 22, 47, 48, and 50 illustrate operations of a method, apparatus, and computer program product according to some example embodiments. It will be understood that each operation of the flowcharts or diagrams, and combinations of operations in the flowcharts or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 114) storing instructions executable by a processor in the computing device (for example, by processor 112). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, optical density instrument 1, including system 100) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer programs products may also be loaded onto a computer or other programmable apparatus (for example, optical density instrument 1, including system 100 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

Many modifications of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. For example, individual methods, portions of methods, apparatus, and portions of apparatus may be exchanged or combined between the embodiments described herein in any feasible combination. Although specific terms are employed herein, they are used in a generic and descriptive sense only and not for purposes of limitation.

The invention claimed is:

1. An optical density testing apparatus, the apparatus comprising:
   a housing configured to receive at least a portion of a sample tube;
   an emitter configured to emit light towards the sample tube;
   at least one sensor configured to receive the emitted light from the emitter and generate a signal indicative of an intensity of the received light;
   a wireless transmitter configured to wirelessly transmit optical density data to a receiving device based upon the signal indicative of the intensity of the received light, wherein the receiving device comprises a base station or a separate computing device; and
   a switch configured to detect the presence of the portion of the sample tube received by the housing, wherein the emitter is configured to emit light towards the sample tube in response to detection of the presence of the sample tube.

2. The optical density testing apparatus according to claim 1, wherein the wireless transmitter is configured to transmit the optical density data directly to the receiving device.

3. The optical density testing apparatus according to claim 1, wherein the wireless transmitter is configured to transmit the optical density data to the receiving device via a wireless communication network.

4. The optical density testing apparatus according to claim 1, wherein the wireless transmitter is configured to transmit the optical density data to the receiving device in real time.

5. The optical density testing apparatus according to claim 1, wherein the wireless transmitter is configured to wirelessly transmit the optical density data to the receiving device continuously during at least a portion of a testing operation during which the emitted light is received by the at least one sensor.

6. The optical density testing apparatus according to claim 5, wherein the continuous wireless transmission of the optical density data to the receiving device occurs in real time.

7. The optical density testing apparatus according to claim 1, wherein, in generating a signal indicative of an intensity of the received light, the at least one sensor is further configured to:
   generate raw light data based upon the emitted light received from the emitter; and
   convert the raw light data into the optical density data.

8. The optical density testing apparatus according to claim 1, wherein the housing of the optical density testing apparatus is configured to receive the receiving device attached thereto.

9. The optical density testing apparatus according to claim 1, wherein the optical density testing apparatus is handheld and configured to be carried by a user during at least a portion of a testing operation during which the emitted light is received by the at least one sensor.

10. The optical density testing apparatus according to claim 1, wherein the housing defines an opening and a cavity, and wherein the housing is configured to receive at least the portion of the sample tube in the cavity via the opening, the optical density testing apparatus further comprising:
    an illumination light disposed in the cavity and configured to illuminate the sample tube to allow the user to view contents of the sample tube.

11. The optical density testing apparatus according to claim 10, wherein the emitter is configured to emit light that is received by the at least one sensor in the absence of operation by the illumination light such that the optical density data is indicative of the intensity of the received light in the absence of the illumination light.

12. The optical density testing apparatus according to claim 1, wherein the receiving device comprises the separate computing device and wherein the wireless transmitter is configured to wirelessly transmit the optical density data to the separate computing device for display.

13. The optical density testing apparatus according to claim 1, wherein the receiving device comprises the base station and wherein the wireless transmitter is configured to wirelessly transmit the optical density data to the base station for display.

14. The optical density testing apparatus according to claim 13, wherein the base station is connected to the separate computing device for displaying the optical density data.

15. An optical density instrument comprising:
a receiving device; and
an optical density testing apparatus, wherein the apparatus comprises:
  a housing configured to receive at least a portion of a sample tube;
  an emitter configured to emit light towards the sample tube;
  at least one sensor configured to receive the emitted light from the emitter and generate a signal indicative of an intensity of the received light;
  a wireless transmitter configured to wirelessly transmit optical density data to the receiving device based upon the signal indicative of the intensity of the received light, wherein the receiving device comprises a base station or a separate computing device; and
  a switch configured to detect the presence of the portion of the sample tube received by the housing, wherein the emitter is configured to emit light towards the sample tube in response to detection of the presence of the sample tube.

16. The optical density instrument according to claim 15, wherein the wireless transmitter is configured to transmit the optical density data directly to the receiving device.

17. The optical density instrument according to claim 15, wherein the wireless transmitter is configured to transmit the optical density data to the receiving device via a wireless communication network.

18. The optical density instrument according to claim 15, wherein the wireless transmitter is further configured to transmit the optical density data to the receiving device in real time.

19. The optical density instrument according to claim 15, wherein the wireless transmitter is further configured to wirelessly transmit the optical density data to the receiving device continuously during at least a portion of a testing operation during which the emitted light is received by the at least one sensor.

* * * * *